United States Patent [19]

Baseman et al.

[11] Patent Number: 5,281,694

[45] Date of Patent: Jan. 25, 1994

[54] METHODS AND COMPOSITIONS FOR PRODUCTION OF MYCOPLASMAL ADHESINS

[75] Inventors: Joel B. Baseman, San Antonio, Tex.; C. J. Su, West Orange, N.J.; S. F. Dallo, San Antonio, Tex.

[73] Assignee: The University of Texas Board of Regents, Austin, Tex.

[21] Appl. No.: 665,792

[22] Filed: Mar. 5, 1991

Related U.S. Application Data

[62] Division of Ser. No. 118,967, Nov. 10, 1987, Pat. No. 5,026,636.

[51] Int. Cl.$^5$ .................... C07K 7/08; C07K 7/00; C07K 13/00
[52] U.S. Cl. .................... 530/324; 530/300; 530/327; 530/350; 530/395; 530/825; 530/808
[58] Field of Search ............... 530/300, 324, 327, 395, 530/350

[56] References Cited

PUBLICATIONS

R. A. Lerner 1984 Adv. Immunol. 36: 1-44.
E. Jacobs et al (1986) Anal. Biochem. 154: 583-589.
Plummer et al.; *Infect. Immun.* 53:398-402 (1986).
Trevino, et al.: *Infect. Immun.* 53:129-134 (1986).
Jacobs et al.; *Journal of General Microbiology* 113:2233-2236 (1987).
Plummer et al.; *Infect. Immun.* 55:49-56 (1987).
Kahane et al.; *Infect. Immun.* 49:457-458 (1985).
Henikoff; *Elsevier Science Publishers* 28:351-359 (1984).
Leith and Baseman; *Journal of Bacteriology* 157:678-680 (1984).
Baseman et al.; *Molecular Basis of Oral Microbial Adhesin,* Ed. Megenhagen, pp. 18-23 (1985).
Morrison-Plummer et al.; *Journal of Immunological methods* 64:165-178 (1983).
Krause and Baseman; *Infect. Immun.* 39:1180-1186 (1983).
Krause et al.; *Infect. Immun.* 39:830-836 (1983).
Leith et al.; *Journal of Experimental Medicine* 157:502-514 (Feb. 1983).
Krause et al.; *Infect. Immun.* 35:809-817 (1982).
Baseman et al.; *Journal of Bacteriology* 151:1514-1522 (1982).
Messing et al.; *Nucleic Acids Research* 9:309-321 (1981).
Young and Davis; *Proc. Natl. Acad. Sci. USA* 80:1194-1198 (Mar. 1983).
Young and Davis; *Science* 222:778-782 (Nov. 1983).
Maniatis et al., *Molecular Cloning, A Laboratory Manual,* Cold Spring Harbor Laboratory (1982).

*Primary Examiner*—Robert A. Wax
*Attorney, Agent, or Firm*—Arnold, White & Durkee

[57] ABSTRACT

The molecular cloning and nucleotide sequence of the complete structural gene encoding *Mycoplasma pneumoniae* P1 cytadhesin and the amino acid sequence of the protein is described. The present invention provides recombinant DNA clones encoding the complete P1 protein as well as clones expressing P1 polypeptides with cytadhesin epitopes. The substantially purified nucleic acid molecules, recombinant vectors, recombinant cells, and recombinant polypeptides of the present invention are useful as hybridization probes and immunodiagnostic reagents and may be used to prepare anti-mycoplasmal vaccines.

5 Claims, 22 Drawing Sheets

FIG.2

```
              1     2     3     4     5     6
PROTEIN   NH2-Asn - Ala - Ile - Asn   Pro - Arg m-RNA    5' AAU   GCX   AUU   AAU   CC 3' ---
               C          C     C
                                A
PROBE    3' TTA   CGX   TAA   TTG   GG 5'
               G            G     A
                                  T 7     8     9    10    11    12
PROTEIN      Leu - Thr - Pro - Trp - Thr - Tyr m-RNA    5' CUX   ACX   CCX   UGG   ACX   UAU 3'
              U                        A         C

PROBE    3' GAX   TGX   GGX   ACC   TGX   ATA 5'
              A                        T         G 13    14    15    16    17    18
           Arg - Asn - Thr - Ser - Phe - Ser
```

LEGEND:
B = Bam H I     H = Hind III    S = Sma I
E = EcoR I      K = Kpn I       SA = Sal I
EV = EcoR V     P = Pst I       SC = Sac I

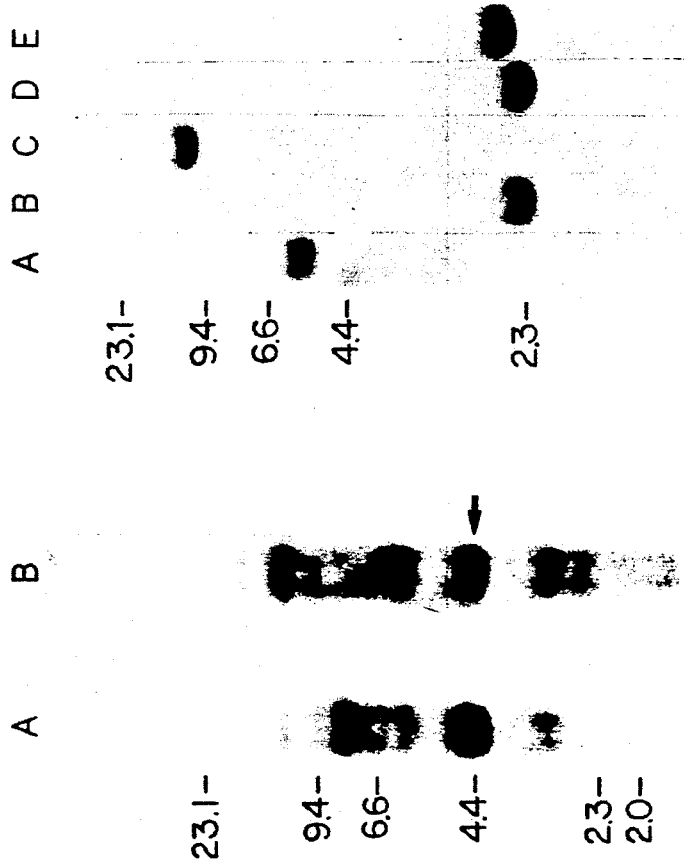

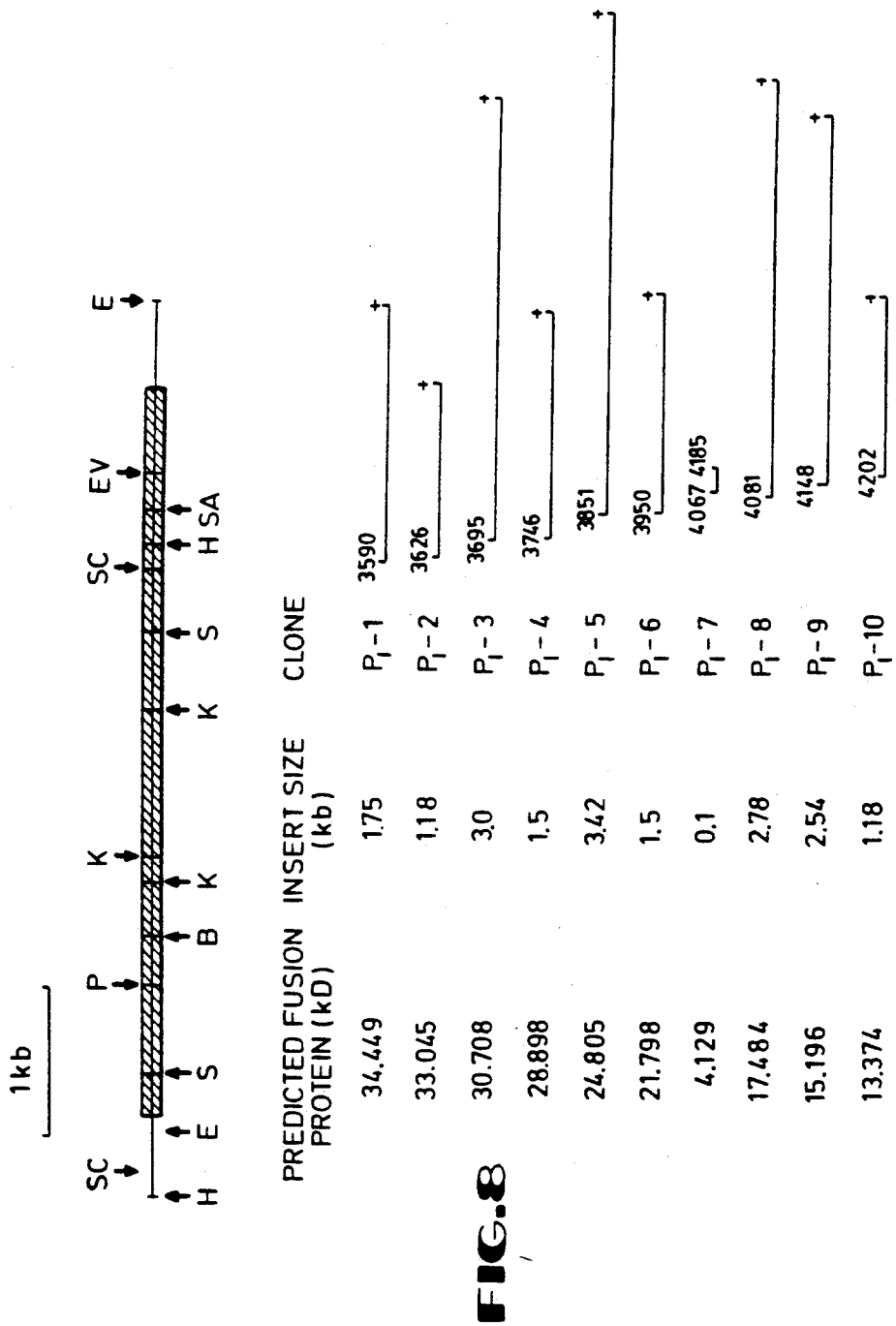

```
                                                                    3960
AAC CTC AGT GTG CTT AGT GGT GGG GGT GCT GGA GGG GGT TCT TCA GGC TCA GGT CAA
Asn Leu Ser Ser Val Leu Ser Gly Gly Gly Ala Gly Gly Gly Ser Ser Gly Ser Gly Gln 3990                                    4020
TCT GGC GTG GAT CTC TCC CCC GTT GAA AAA GTG GGG TGG CTT GTG GGG CAG TTA CCA
Ser Gly Val Asp Leu Ser Pro Val Glu Lys Val Gly Trp Leu Val Gly Gln Leu Pro

4050                                          ▼             4080
AGC ACG AGT GAC GGA AAC ACC TCC ACC AAC AAC CTC GCG CCT AAT ACT AAT ACG GGG
Ser Thr Ser Asp Gly Asn Thr Ser Thr Asn Asn Leu Ala Pro Asn Thr Asn Thr Gly 4110                                            4140
AAT GAT GTG /GTG GGG GTT GGT CGA CTT TCT GAA AGC CTG AAG ATG AAT GAC GAT
Asn Asp Val Val Gly Val Gly Arg Leu Ser Glu Ser Asn Ala Ala Lys Met Asn Asp Asp

*                                             4170                                4200
GTT GAT GGT ATT GTA CGC ACC CCA CTC GCT GAA CTG TTA GAT GGG GAA GGA CAA ACA GCT
Val Asp Gly Ile Val Arg Thr Pro Leu Ala Glu Leu Leu Asp Gly Glu Gly Gln Thr Ala
                                                                  ▲
 ▽                                  4230                                          4260
GAC ACT GGT CCA CAA AGC GTG AAG TCT CCT GAC CAA ATT GAC TTC AAC CGC TTG
Asp Thr Gly Pro Gln Ser Val Lys Ser Pro Asp Gln Ile Asp Phe Asn Arg Leu
```

FIG. 9A

```
TTT ACC CAC CCA GTC ACC GAT CTG TTT GAT CCG GTA ACT ATG TTG GTG TAT GAC CAG TAC
Phe Thr His Pro Val Thr Asp Leu Phe Asp Pro Val Thr Met Leu Val Tyr Asp Gln Tyr
                                      4290                              4320

ATA CCG CTG TTT ATT GAT ATC CCA GCA AGT GTG AAC CCT AAA ATG GTT CGT TTA AAG GTC
Ile Pro Leu Phe Ile Asp Ile Pro Ala Ser Val Asn Pro Lys Met Val Arg Leu Lys Val
              4350                                              4380

TTG AGC TTT GAC ACC AAC AAC GAA CAG AGC TTA GGT CTC CGC TTA GAG TTC TTT AAA CCT GAT
Leu Ser Phe Asp Thr Asn Asn Glu Gln Ser Leu Gly Leu Arg Leu Glu Phe Phe Lys Pro Asp
                          4410                                      4440

CAA GAT ACC CAA CCA AAC AAC AAC GTT CAG GTC AAT CCG AAT AAC GGT GAC TTC TTA CCA
Gln Asp Thr Gln Pro Asn Asn Asn Val Gln Val Asn Pro Asn Asn Gly Asp Phe Leu Pro
                    4470                                      4500

CTG TTA ACG GCC TCC AGT CAA GGT CCC CAA ACC TTG TTT AGT CCG TTT AAC CAG TGA CCT
Leu Leu Thr Ala Ser Ser Gln Gly Pro Gln Thr Leu Phe Ser Pro Phe Asn Gln Trp Pro
              4530                                      4560
```

FIG.9B

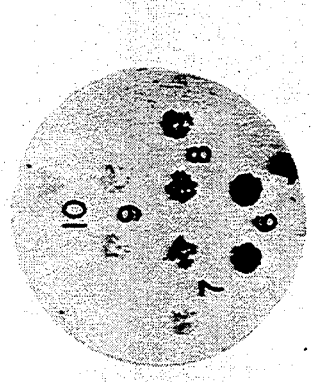 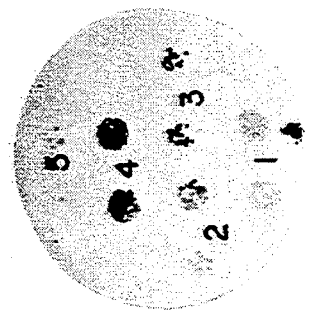
FIG.12-III
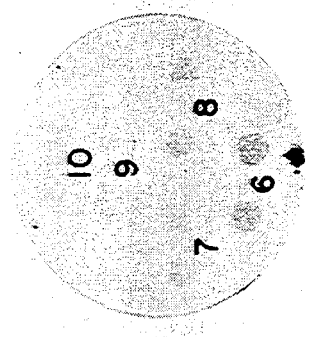 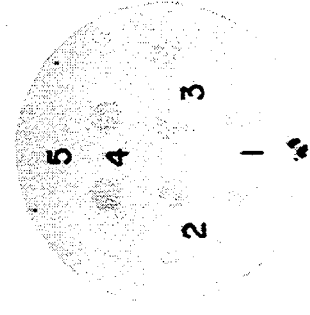
FIG.12-II
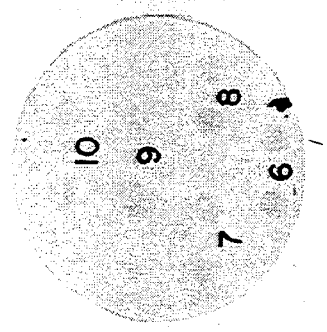 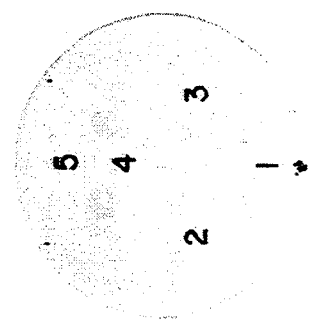
FIG.12-I

```
TTAAGGCATCATTGCCTTAATTGCATGCGCTTCATGCGAAATTTCATACCACCGCCCCCAGTATAAGTCCGTCGCCACG
AATTCCGTAGTAACGGGAATTAACGCGGAAGTAGCTTTAAAGTATGGTGCGGGGGTCATATTCAGGCCAGGGTGC

TCAAGAATTTCGTTCGCGCTGTATTAAGCACATCAAGTTCTAACGGTTTTCGTTAACGACATATTAAAATTGTGA
AGTTCTTAAAGCAAGCGCGACATAATTCGTGTAGTTCAAGATTGCCAAAAGCAAATTGCTGTATAATTTTAACAACT
                                                                           60

TAC GTG GTT TGG TTT TTT TGA CGG AAC AGG TTC AGG TGA ACC TAA GAG TAG TGG CGG
ATG CAC CAA ACC AAA AAA ACT GCC TTG TCC ACT TGG ATT CTC ATC CTC ACC GCC
Met His Gln Thr Lys Lys Thr Ala Leu Ser Thr Trp Ile Leu Ile Leu Thr Ala
                           30
                                                                           120
TGG CGG AGG GAG CGC TGC CCT GAG TGG CAT CAC CCT GTG AAG TGT TCA TGG TGC TGC
ACC GCC TCC CTC GCG ACG GGA CTC GTA GGA CAC GTG GGA CAC TTC ACA AGT ACC ACG ACG
Thr Ala Ser Leu Ala Thr Gly Leu Thr Val Val Gly His Pro Val Lys Phe Thr Thr Thr
                           90
                                                                           180
GAG TTC GCG GTC GTT AAA TCG ATG TGG GCG GGA CTG CTC CAG CGC GAC GCG GTG TGG TTA
CTC AAG CGC CAG CAA TTT AGC TAC ACC CCG TGA GAC GAG GTC GCG CTG CGC CAC ACC AAT
Leu Lys Arg Gln Gln Phe Ser Tyr Thr Arg Pro Asp Glu Val Ala Leu Arg His Thr Asn
                           150
                                                                           240
CGG TAG TTG GGC GCG AAT TGG GGC ACT TGC ATA GCA TTG TGC TCG AAA AGG AGG GAG GGG
GCC ATC AAC CCG CGG GCG TTA ACC CCG TGA ACG TAT CGT AAC ACG AGC TTT TCC CTC CCC
Ala Ile Asn Pro Arg Leu Thr Pro Trp Thr Tyr Arg Asn Thr Ser Phe Ser Leu Pro
                           210
                                                                           300
GAG TGC CCA CTT TTA GGG CCC CGC ACC CGG AAT CAC GCG CTG TTG TCG CGA TTC CCG TAG
CTC ACG GGT GAA AAT CCC GGG GCG TGG CCC TTA GTG CGC GAC AAC AGC AGC GCT AAG GGC ATC
Leu Thr Gly Glu Asn Pro Gly Ala Trp Ala Leu Val Arg Asp Asn Ser Ala Lys Gly Ile
                           270
```

FIG. 6A

```
                                              330                                                    360
TGA CGG CCG TCA GTT CCG TCA GTT TGG ATA CTA GGG TGG GCT TGG CTT CGC CGA AAC
ACT GCC GGC AGT CAA ACC GGC AGT TAT GAT CCC ACC CGA GAA GCG GCT
Thr Ala Gly Ser Gln Thr Gly Ser Tyr Asp Pro Thr Arg Thr Arg Glu Ala Ala Leu 390                                                    420
TGG CGT AGT TGG TGG AAA CGC AAT GCC ATA CTG GAG CGG CCC GGG AAT ATG CTG
ACC GCA TCA ACC ACC TTT GCG CGG TTA CGC TAT GAC CTC GCC GCC TTA TAC GAC
Thr Ala Ser Thr Thr Phe Ala Arg Leu Arg Tyr Asp Leu Ala Ala Leu Tyr Asp 450                                                    480
GAG CTA AAA AGC TTC AAT TTG GGC TGC GGG GTT CTG GTT TGG CCC GTC TAG TGG
CTC GAT TCG AAG TTA AAC CCG CCC ACG GAC CAA ACC GGG CAG ATC ACC
Leu Asp Phe Ser Lys Leu Asn Pro Gln Thr Pro Arg Asp Gln Thr Gly Gln Ile Thr 510                                                    540
AAA TTG GGG/AAA CCG CCC AAA CCA AAC TCA CCC CGA CGT GGG GTT GTC ACT TTG CTC CAG
TTT AAC CCC TTT GGC GGC TTT GGT AGT TTG GGG GCT GCA CCC CAA CAG TGA AAC GAG
Phe Asn Pro Phe Gly Gly Phe Gly Ser Leu Gly Ala Ala Pro Gly Gln Trp Asn Glu Val 570                                                    600
TTT TTC CAG GGG CAG CTC CAC CAC ATG GGG AGG TTA GGG ATG GCC AAA CGG CAA
AAA AAG GTC CCC GTC GAG GTG TAT CAA CCC AAT TCC TAC CGG TTT GCC GTT
Lys Asn Lys Val Pro Val Glu Val Tyr Gln Asp Pro Ser Asn Pro Tyr Arg Phe Ala Val 630                                                    660
AAT GAG CAC GGC GCG TCG ATA CTC GTC CGC CAC ATG GCC GTC AAC CCC AAT GGT
TTA CTC GTG CCG CGC AGC GTG TAC GAG CAG TTG CAA AGG GGG TTG GCC TTA CCA
Leu Leu Val Pro Arg Ser Val Val Tyr Glu Gln Leu Gln Arg Gly Leu Gly Leu Pro
```

FIG. 6B

```
                                                                                                 720                                     780                                     840                                     900                                     960                                    1020
GTC GCT TGG CTC TCA CCA GTT TTA TGA AGG TGG CCC CGT TAC AAA CCG AAC TTC
CAG CGA GAG AGT GGT CAA AAT        690 ACT TCC ACC GGG GCA ATG GGC TTG AAG
Gln Arg Glu Ser Gly Gln Asn              Thr Ser Thr Gly Ala Met Phe Gly Leu Lys

CAC TTC TTG CGG CTC CGC TGG CTG TCG TTA CTT TTT GAG GTC CCG CGA CTC CGG
GTG AAG AAC GCC GAG GAC GCG ACC AGC AAG GAA AAA CTC CAG GCT GAG GCC
Val Lys Asn Ala Glu Asp Ala Thr Ser Lys Glu Lys Leu Gln Ala Glu Ala Ala

TGA CCA AGA AGT TGG TGT AGA CCT AGA                                       810 CCG GTT GCA CCC CCA AGC CTG AGT CCC
ACT GGT TCT TCA ACC ACA TCT GGA TCT                                           GGC CAA TCC GGG CGT GGT TCG TCA GGG
Thr Gly Ser Ser Thr Thr Ser Gly Ser                                           Gly Gln Ser Gly Arg Gly Ser Ser Gly

CTG TGG TTT CAG TTC CGA AAT TTT TAT CTC CAC TTT TTC AGC CTG TTA
GAC ACC AAA GTC AAG GCT TTA AAA ATA GAG GTG AAA AAG CGG GAC AAT
Asp Thr Lys Val Lys Ala Leu Lys Ile Glu Val Lys Lys Arg Asp Asn
                                                                     870                                     930
CCA GTC GAC GTC AAT CTT TTT AAA CTA                                       CGG TTG CGA AAC GCT CCC ATT AAG CTC
GGT CAG CTG CAG TTA GAA AAA CTG GAT                                           GAG CTC GCC GCT ACT TCC AAG GAG
Gly Gln Leu Gln Leu Glu Lys Asp Leu                                           Glu Leu Ala Pro Ile Lys Arg Glu
                                                                                                        930                                     990
AGC CCA GTC AGG CAG GTT GAG TTC CGC CTG CTA AAA CCA TGA CGG GAA CCT
TCG GGT CAG TCC CAA CTC AAG GAC GAT GCG CTT GGT ACT GCC CTT TCC GGA
Ser Gly Gln Ser Val Gln Leu Lys Asp Asp Ala Leu Gly Thr Ala Leu Ser Gly
```

FIG. 6C

```
                                          1050                                    1080
AGT CCG TTG AGG TTA GGG CCA AGG GGG ACT TCC GGC TGG GGG TGG ACC GAA CGC TGA CTC
TCA GGC AAC TCC AAT CCC GGT TCC CCC TGA AGG CCG ACC CCC ACC TGG CTT GCG ACT GAG
Ser Pro Leu Arg Leu Gly Pro Arg Gly Thr Ser Gly Trp Gly Trp Thr Glu Arg Leu Glu 1110                                    1140
GTT TAA GTG TTC CTG GAG GGG TTT ACT AGG CGG AGC TAG GAC ATG CTA CGC GGA
CAA ATT CAC AAG GAC CTC CCC AAA TGA TCC GCC TCG ATC CTG TAC GAT GCG CCT
Gln Ile His Lys Asp Leu Pro Lys Leu Pro Ser Ala Ser Ile Leu Tyr Asp Ala Pro 1170                                    1200
ATA CGC GCG TTG GCA TGG CGG TAA CTG GCG CAA CTA GTG AAC CTA GGG TTC TAC TGG
TAT GCG CGC AAC CGT ACC GCC ATT GAC CGC GTT GAT CAC TTG GAT CCC AAG ATG ACC
Tyr Ala Arg Asn Arg Thr Ala Ile Asp Arg Val Asp His Leu Asp Pro Lys Met Thr 1230                                    1260
CGC TTG ATA GGC GGG TCA ACT TCT TGC GGG TTG GTG CCA AAC ACC CTG ACT
GCG AAC TAT CCG CCC AGT TGA AGA ACG CCC AAC CAC GGT TTG TGG GAC TGA
Ala Asn Tyr Pro Pro Ser Trp Arg Thr Pro Asn His His Gly Leu Trp Asp Trp 1290                                    1320
TTC CGC GCG CTA CAA AAC GAG GTT TGG TGG CCC AAG AAG TTG GGC GCG GTG CTC
AAG GCG CGC GAT GTT TTG CTC CAA ACC ACC GGG TTC TTC AAC CCG CGC CAC GAG
Lys Ala Arg Asp Val Leu Leu Gln Thr Thr Gly Phe Phe Asn Pro Arg His Pro Glu 1350                                    1380
ACC AAA CTA CCG CCC GTC TGC CAG CGC CTA TTG CTT TTC TGG CCC AAA CTA CAC TTG
TGG TTT GAT GGC GGG CAG ACG GTC GCG GAT AAC GAA AAG ACC GGG TTT GAT GTG AAC
Trp Phe Asp Gly Gly Gln Thr Val Ala Asp Asn Gly Lys Thr Gly Phe Asp Val Asn
```

FIG. 6D

```
                                                            1440
AGA CTT TGG TTC GTC CCG AAA GTT CTT CGA CTG AGG CTG TTC AGC CGG GGC TAG
TCT GAA AAC ACC AAG CAG GGC TTT CAA GAA GCT GAC TCC GAC AAG TCG GCC ATC
Ser Glu Asn Thr Lys Gln Gly Phe Gln Lys Glu Ala Asp Ser Asp Lys Ser Ala Pro Ile
                                                            1500
CGG GAG GGC AAA CTT CGC ATG AAG CGG TTG TAA CCG TTG GAG TGG ACC AAG CCC GTT CGC
GCC CTC CCG TTT GAA GCG TAC TTC GCC AAC ATT GGC AAC CTC TGG TTC GGG CAA GCG
Ala Leu Pro Phe Glu Ala Tyr Phe Ala Asn Ile Gly Asn Leu Thr Trp Phe Gly Gln Ala
                                                            1560
GAA AAC CAC AAA CCA CCG TTA CCG GTA CAA TGG TTC AGC CGG GTG TGG CGC GGA AAC TCA
CTT TTG GTG TTT GGT GGC AAT GGC CAT GTT ACC AAG TCG GCC CAC ACC GCG CCT TTG AGT
Leu Leu Val Phe Gly Gly Asn Gly His Val Thr Lys Ser Ala His Thr Ala Pro Leu Ser
                                                            1620
TAT CCA CAG AAA TCC CAC GCG ATA TTA CGT TGA CCT TGG TCA CGA TGA CAT TGA CCA ACT
ATA GGT GTC TTT AGG GTG CGC TAT AAT GCA ACT GGT ACC AGT GCT ACT GTA ACT GGT TGA
Ile Gly Val Phe Arg Val Arg Tyr Asn Ala Thr Gly Thr Ser Ala Thr Val Thr Gly Trp
                                                            1680
GGT ATA CGG AAT GAC AAG AGT CCG TAC CAG TTT GTT TGA CTG CCC AAT TTC CTA GAT
CCA TAT GCC TTA CTG TTC TCA GGC ATG GTC AAA CAA ACT GAC GGG TTA AAG GAT CTA
Pro Tyr Ala Leu Leu Phe Ser Gly Met Val Asn Lys Gln Thr Asp Gly Leu Lys Asp Leu
                                                            1740
GGG AAA TTA TTG GCG ACC AAA CTT ATA CAT GGT GCC TAC CGT CAA CGA CCG CGA TTC
CCC TTT AAC AAT AAC CGC TGG TTT GAA TAT GTA CGG ATG CCA GTT GCA GGC GCT AAG
Pro Phe Asn Asn Arg Trp Phe Glu Tyr Val Pro Arg Met Ala Val Ala Gly Ala Lys

FIG. 6E
```

```
AAG CAA CCA TCC CTT GAG CAA AAT CGC CCA TGG TAA TGG TAC CCA CTA TGG CGA TGG CAT
TTC GTT GGT AGG GAA CTC GTT TTA GCG GGT ACC ATT ACC ATG GAT GGT ACC GCT ACC GTA
Phe Val Gly Arg Glu Leu Val Leu Ala Gly Thr Ile Thr Met Gly Asp Gly Ala Thr Val
                    1770                                        1800

GGA GCG AAT GAC ATG CTA CTT GAA CTT TCG TTG GAC TTG AAT CAT CGC GTT CCG GTT CCA
CCT CGC TTA CTG TAC GAT GAA CTT GAA AGC AAC CTG GTA TTA GTA GCG CAA GGC CAA GGT
Pro Arg Leu Tyr Asp Leu Glu Leu Glu Ser Asn Leu Asn Leu Val Ala Gln Gly Gln Gly
                    1830                                        1860

GAA AAT GCG CTT CTG AAC GTT CAA TGT GAG AAG TGT GGG ATG CCT ACT CGG TTA GCA GGC CTA AAT
CTT TTA CGC GAA GAC TTG CAA CTC ACA TCG CTC TTC ACA TAC CCC TGA GCC AAT CGT CCG GAT TTA
Leu Leu Arg Ala Glu Asp Leu Gln Leu Phe Thr Pro Tyr Gly Trp Ala Asn Arg Pro Asp Leu
                    1890                                        1920

GGT TAG CCC CGA ACT TCA TCA TCA GTG TTG CGT GGG ATG ATG AAG GTG
CCA ATC GGG GCT TGA AGT AGT AGT CAC GCA ACA TAC TAC TTC CAC
Pro Ile Gly Ala Trp Ser Ser Ser His Asn Ala Pro Tyr Tyr Phe His
                    1950                                        1980

TTA TTG GGG CTA ACT GTT CTG GCA GGT TAG GTT TTA CAC CAA CTA CGG AAA TAA TTC GGG
AAT AAC CCC GAT TGA CAA GAC CGT CCA ATC CAA AAT GTG GTT GAT GCC TTT ATT AAG CCC
Asn Asn Pro Asp Trp Gln Asp Arg Pro Ile Gln Asn Val Val Asp Ala Phe Ile Lys Pro
                    2010                                        2040

ACT CTC CTG TTC TTG CCA TTT ATG TAG ATG GGA ATG GCA ATG TCA CCG
TGA GAG GAT AAG AAC GGT AAA TAC ATC TAC CCT TAC CGT TAC AGT GGC
Trp Glu Asp Lys Asn Gly Lys Tyr Ile Tyr Pro Tyr Arg Tyr Ser Gly
                    2070                                        2100
```

FIG. 6F

```
                                                              2130                              2160
TAC ACT CGA ACT GTC CAT ATG TTG ACC AGG TTA TTC GAG TGA CTG GTT AAT TCA CGA
ATG TGA GCT TGA CAG GTA TAC AAC TGG TCC AAT AAG CTC ACT GAC CAA CCA TTA AGT GCT
Met Trp Ala Trp Gln Val Tyr Asn Trp Ser Asn Lys Leu Thr Asp Gln Pro Leu Ser Ala 2190                              2220
CTG AAA CAG TTA CTC TTA CGA ATG GTT GGT TTG AGG AAC AAA CGA TAA GAG TTA GGC
GAC TTT GTC AAT GAG AAT GCT TAC CAA CCA TCC TTG AAC TTT GCT ATT CTC AAT CCG
Asp Phe Val Asn Glu Asn Ala Tyr Gln Pro Ser Asn Phe Ala Ile Leu Asn Pro 2250                              2280
CTT AAC AAT CGT CGA GAA GGG CTG TTC CAA TTT ATG CCA TTC CTC AAA CGA CGA
GAA TTG TTA GCA GCT CTT CCC GAC AAG GTT AAA TAC GGT AAG GAG TTT GCT GCT
Glu Leu Leu Ala Ala Leu Pro Asp Lys Val Lys Tyr Gly Lys Glu Phe Ala Ala 2310                              2340
TTG CTC ATG CTC GCG AAA TTG GTC TTC AAT TGC CAT CGA GGA TGG GTT CCT TGT TTG ACT
AAC GAG TAC GAG CGC TTT AAC CAG AAG TTA ACG TTA GCT ACC CCT ACC CAA GGA ACA AAC TGA
Asn Glu Tyr Glu Arg Phe Asn Gln Lys Leu Thr Ala Pro Thr Gln Gly Thr Asn Trp 2370                              2400
AGG GTG AAG AGG TGC GAA AGG GCA AAG AGG TGG CCC AAG TTG GAA CAC CCC AGC CAC
TCC CAC TTC TCC ACG CTT CGT TCC TTC CGT ACC GGG TTC AAC CTT GTG GGG TCG GTG
Ser His Phe Ser Pro Thr Leu Ser Arg Phe Ser Thr Gly Phe Asn Leu Val Gly Ser Val 2430                              2460
GAG CTG GTC CAC AAC CTA ATA CAC GGG ACC TAA CCC ATG TCC ATA CCG TTA TTG
CTC GAC CAG GTG TTG GAT TAT GTG CCC TGG ATT GGG CCC TAC AGG TAT GGC AAT AAC
Leu Asp Gln Gln Val Leu Asp Tyr Val Pro Trp Ile Gly Asn Gly Tyr Arg Tyr Gly Val Asn Asn
```

FIG. 6G

```
GTG GCC CCG CAC CTA TAT TGG CGC CCC AGC AGG TCG CCT TAA
CAC CGG GGC GTG GAT ATA ACC AGC GGG TCG AGC GGA ATT
His Arg Gly Val Asp Ile Thr Ser Ala Gly Ser Ser Gly Ile
                    2490                              2520

TCA TGC TTG TGT TCA CCA AGC GCA AGG AAA GAG GGC TTG TAG CCG CAG CCG
AGT ACG AAC ACA AGT GGT TCG CGT TCC TTT CTC CCG TCC AAC ATC GGC GTC GGC
Ser Thr Asn Thr Ser Arg Ser Phe Leu Pro Thr Phe Ser Asn Ile Gly Val Gly
                    2550                              2580

GAG TTT CGC TTA CAG GTT CGG TGG GAG CCC TCA GTC TGC TAC TAA TGT CCG CCA AGC
CTC AAA GCG AAT GTC CAA GCC ACC CTC GGG AGT CAG ATG ATT ACA GGC GGT TCG
Leu Lys Ala Asn Val Gln Ala Thr Leu Gly Ser Phe Gln Thr Met Ile Thr Gly Ser
                    2610                              2640

GGA GCT TCT TGG GAG CTG GTT CGG GAG ACT TGC CCC CGC CCC ACT TCC TTA
CCT CGA AGA ACC CTC GAC CAA GCC CTC TGA ACG GGG GCG GGG TGA AGG AAT
Pro Arg Arg Thr Leu Asp Gln Ala Leu Trp Thr Ala Gly Trp Arg Asn
                    2670                              2700

CTA TTC CGA AGT TCA CCT GTT AGT TCA CTG CTT TTG GTG TTC AAG TGC TCG CGA TGC CCC
GAT AAG GCT TCA AGT GGA CAA TCA GAC GAA AAC CAC ACC AAG TTC ACG AGC GCT ACG
Asp Lys Ala Ser Ser Gly Gln Ser Asp Glu Asn His Thr Lys Phe Thr Ser Ala Thr Gly
                    2730                              2760

TAC CTG GTC CCT GTT AGT CCA TGG AGG CGC CCC TTA GGG CTG AGC AAT TTC GTC CTA
ATG GAC CAG CAG GGA TCA GGT ACC TCC GCG GGG AAT CCC TCG TTA AAG CAG GAT
Met Asp Gln Gln Gly Ser Gly Thr Ser Ala Gly Asn Pro Ser Leu Lys Gln Asp
                    2790                              2820
```

```
                                                                    2880
TTA TAA TCA TTC TCA CCC CTA TCA AAT TGG TGC GTC CTG CCG TTA CGC TAG CTA GTT GTT
AAT ATT AAG AGT AGT GAT GGG GAT AGT ACG CAG GAC GGC AAT GCG ATC GAT CAA CAA
Asn Ile Ser Lys Ser Gly Asp Ser Leu Thr Gln Asp Gly Asn Ala Ile Asp Gln Gln
            2850

2940
CTC CGG TTG ATG TGG TTG GAG GGG TTG CGA CTA ACT GGC TTG
GAG GCC ACC AAC TAC ACC CTC CCC AAC CTC ACC GCT TGA CCG AAC
Glu Ala Thr Asn Tyr Thr Pro Asn Leu Thr Pro Ala Asp Trp Pro Asn
            2910

3000
CGC GAC AGT AAG TGG TTC TTG TTG CGC GTC GAG AAG GAG GCG CCG AAG
GCG CTG TCA TTC ACC AAG AAC GCG CAG CGC CTC CGC GGC TTG
Ala Leu Ser Phe Thr Asn Lys Asn Ala Arg Ala Gln Leu Phe Leu Arg Gly Leu
            2970

3060
AAC CCG TCG TAG GGC CAC AAC CAC TTA GCT TCA CCC AGG TTG TTT AAG GTT CGG
TTG GGC AGC ATC CCG GTG TCG AAT CGA AGT TCC GAT AAC TTC AAA TTC CAA GCC
Leu Gly Ser Ile Pro Val Leu Val Asn Arg Ser Asp Ser Asn Lys Phe Gln Ala
            3030

3120
TGG CTG GTT TTT ACC AGG ATG TGG CTG AAT GTA AGC CTG GTT TGG TTT GAC GAG GGG
ACC GAC CAA AAA TGG TCC TAC ACC TCG GAC CAA ACC CAA ACC CTG AAC CTC CCC
Thr Asp Gln Lys Trp Ser Tyr Thr Asp Leu His Ser Asp Gln Thr Lys Asn Leu Pro
            3090

3180
CGA ATG CCA CTC CAC TTA CCC AAC AAC TTA GGC CGC AAC CAC CTT TGG ATA AAA CCC TTG
GCT TAC GGT GAG GTG AAT GGG TTG TTG AAT CCG GCG TTG GTG GAA ACC TAT TTT GGG AAC
Ala Tyr Gly Glu Val Asn Gly Leu Leu Asn Pro Ala Leu Val Glu Thr Tyr Phe Gly Asn
            3150
```

```
                                                            3240
TGC GCT CGC CCA CCA AGC CCC AGG TTG TGC TGG TCA AGT GGG CCA AAA TTT TAA
ACG CGA GCG GGT GGT TCG GGG TCC AAC ACG ACC AGT TCA CCC GGT ATC GGT ATT
Thr Arg Ala Gly Gly Ser Gly Ser Asn Thr Thr Ser Ser Pro Gly Ile Gly Phe Lys Ile
                                                            3300
GGG CTT GTT TTA CTA AGG TTT CGG TAG TGG GGG CCC AAC CGA ACT TGC GGG
CCC GAA CAA AAT GAT TCC AAA GCC ATC ACC CCC GGG TTG GCT TGA ACG CCC
Pro Glu Gln Asn Asn Asp Ser Lys Ala Thr Ile Thr Pro Gly Leu Ala Trp Thr Pro
                                                            3360
GTC CTG CAG CCA TTG GAG CAA CAG TCA CCG TGG TGC CAG TCG AAG GTC GAG CCG CCC ACC
CAG GAC GTC GGT AAC CTC GTT GTC AGT GGC ACG TTC AGC GTC AGC CTC GGC GGG TGG
Gln Asp Val Gly Asn Leu Val Val Ser Gly Thr Thr Val Ser Phe Gln Leu Gly Gly Trp
                                                            3420
GAC CAG TGG AAG TGC CTG AAA CAG TTT GGG GCG CCA ATG GAG CCA GAG GTC AAT TGC
CTG GTC ACC TTC ACG GAC CTC GTC AAA CCC GGT GGT TAC CTC GGT CTC CAG TTA ACG
Leu Val Thr Phe Thr Asp Phe Lys Pro Arg Ala Gly Tyr Leu Gly Leu Gln Leu Thr
                                                            3480
CCG AAC CTA CGT TCA CTA CGC TGC GTC CGC GAG TAA ACC CGG GGG ACT CGC
GGC TTG GAT GCA AGT GAT GCG ACG CAG CGC CTC ATT TGG GCC CGG CCC TGA GCG
Gly Leu Asp Ala Ser Asp Ala Thr Gln Arg Ala Leu Ile Trp Ala Pro Arg Trp Ala
                                                            3540
CGG AAA GCA CCG TCA ACC CAG TTG GCC AAC CCG GGC CAC CTC TCA CAC ACC TTC
GCC TTT CGT GGC AGT TGG GTC AAC CGG TTG GCC CCG CGC GTG GAG AGT GTG TGG AAG
Ala Phe Arg Gly Ser Trp Val Asn Arg Leu Gly Arg Val Glu Ser Val Trp Asp Leu Lys
```

FIG.6J

```
CCC CAC CGC CTA GTT CGA GTC CAG AGC GTT CCT AGA TGG CGT TGT TCC
GGG GTG GCG GAT CAA GCT CAG TCC GAA TCT ACC GCA AGG
Gly Val Trp Ala Asp Ser Gln Gly Ser Thr Thr Ala Arg
                                                              3600

3570
TTG CGG AAT GGC CTC GTG GGC TTA CGA AAC CGG AAA GTC CAC CAC CTT
AAC GCC TTA CCG CAC CCG AAT GCT TTG GCC TTT CAG GTG GTG GAA GCG
Asn Ala Leu Pro Glu His Pro Asn Ala Leu Ala Phe Gln Val Val Glu Ala Ser
                                                              3660

3630
CGA ATG TTC GGT TTG TGC TCG AGG CCG GTT TGG CCG GTT AGG TGA ATG
GCT TAC AAG CCA AAC ACG AGC TCC CAA GCC TCC CAA TCC ACT TCC CCC
Ala Tyr Lys Pro Asn Thr Ser Ser Gln Ala Phe Gln Ser Thr Asn Ser Ser Pro Tyr Leu
                                                              3720

3690
GTG AAC CAC TTC GGA TTC TTT CAA AGG CTG GTT AGG CTG CTA GAA TTT TTG
CAC TTG GTG AAG CCT AAG AAA GTT ACC CAA TCC GAC GAT CTT AAA AAC
His Leu Val Lys Pro Lys Val Thr Gln Ser Asp Lys Leu Asp Asp Lys Leu Lys Asn
                                                              3780

3750
GAC AAC CTG GGG TTG GTC CAA GCG TTC GAC TGG CCA TGT CTG GTA AGG
CTG TTG GAC CCC AAC CAG CGC AGC CTG ACA GAC CAT TCC
Leu Leu Asp Pro Asn Gln Val Arg Ser Phe Gly Thr Asp His Ser
                                                              3840

3810
TGG GTC GGG GTT AGC GAG TTT TGT TGC CAT AAA CCC TGC TCA TCA CCA
ACC CAG CCC CAA TCG CTC AAA ACA ACG CCG GTA ACG AGT GGT
Thr Gln Pro Gln Ser Leu Lys Thr Thr Pro Val Phe Gly Thr Ser Ser Gly
                                                              3900

```
TTG GAG TCA CAC GAA TCA CCA CCC CCA CGA CCT GGA GGT CCA AGA AGT CCG AGT CCA GTT
AAC CTC AGT GTG CTT AGT GTT GGT GGG GCT GCT CCT GGG GGT TCT TCA GGC TCA GGT CAA
Asn Leu Ser Val Leu Ser Val Gly Gly Ala Ala Pro Gly Gly Ser Ser Gly Ser Gly Gln
                                  3930                                  3960

AGA CCG CAC CTA GAG AGG GGG CAA CTT TTT CAC CTT GAA ACC GAA CAC CCC GTC CCC AAT GGT
TCT GGC GTG GAT CTC TCC CCC GTT GAA AAA GTG GAA CTT TGG CTT GTG GGG CAG GGG TTA CCA
Ser Gly Val Asp Leu Ser Pro Val Glu Lys Val   Leu Trp Leu Val Gly Gln Leu Pro
                                  3990                                  4020

TCG TGC TCA CTG CCT TTG TGG AGG AGG CAA TGG TTG GAG CGC GGA TTA TGA TTA TGC CCC
AGC ACG AGT GAC GGA AAC ACC TCC TCC GTT ACC AAC CTC GCG CCT AAT ACT AAT ACG GGG
Ser Thr Ser Asp Gly Asn Thr Ser Ser Val Thr Asn Leu Ala Pro Asn Thr Asn Thr Gly
                                  4050                                  4080

TTA CTA CAC CCC CAA GCT GAA AGA CTT TCG TTG CGG CGT TTC TAC TTA CTG CGA
AAT GAT GTG GGG GTT CGA CTT TCT GAA AGC GCA AAG ATG AAT GAC
Asn Asp Val Gly Val Arg Leu Ser Glu Ser Asn Ala Ala Lys Met Asn Asp Asp
                                  4110                                  4140

CAA CTA CCA TAA CAT GCG TGG GGT CGA GAG CTT GAC AAT CTA CCC CTT TGT CGA
GTT GAT GGT ATT GTA CGC ACC CCA GCT CTC GAA CTG TTA GAT GGG GAA ACA GCT
Val Asp Gly Ile Val Arg Thr Pro Ala Leu Glu Leu Asp Gly Glu Thr Ala
                                  4170                                  4200

CTG TGA CCA GGT GTT TCG CAC TTC AAG AGA GGA CTG GTT TAA CTG GTT TGA AAC TTG
GAC ACT GGT CCA CAA AGC GTG AAG TTC TCT CCT GAC CAA ATT GAC TTC AAC CGC
Asp Thr Gly Pro Gln Ser Val Lys Phe Lys Ser Pro Asp Gln Ile Asp Phe Asn Arg Leu
                                  4230                                  4260
```

FIG. 6M

```
                                                4290
AAA TGG GTG GGT CAG TGG CTA GAC AAA CTA GGC CAT TGA TAC AAC CAC ATA CTG GTC ATG
TTT ACC CAC CCA GTC ACC GAT CTG TTT GAT CCG GTA ACT ATG GTG TAT GAC CAG TAC
Phe Thr His Pro Val Thr Asp Leu Phe Asp Pro Val Thr Met Leu Val Tyr Asp Gln Tyr
                                                                            4320

4350
TAT GGC GAC AAA TAA CTA TAG GGT CGT TCA CAC TTG GGA TTT TAC CAA GCT AAT TTC CAG
ATA CCG CTG TTT ATT GAT ATC CCA GCA AGT GTG AAC CCT AAA ATG GTT CGT TTA AAG GTC
Ile Pro Leu Phe Ile Asp Ile Pro Ala Ser Val Asn Pro Lys Met Val Arg Leu Lys Val
                                                                            4380

4410
AAC TCG AAA CTG TGG CTT GTC TCG AAT CCA GAG GCG AAT CTC AAG AAA TTT GGA CTA
TTG AGC TTT GAC ACC TTA CAG AGC TTA GGT CTC CGC TTA GAG TTC AAA CCT GAT
Leu Ser Phe Asp Thr Asn Glu Gln Ser Leu Arg Leu Gly Phe Glu Lys Phe Phe Pro Asp
                                                                            4440

4470
GTT CTA TGG GTT GGT TTG CAA GTC CAG TTA GGC TTA CCA CTG AAG AAT GGT
CAA GAT ACC CAA CCA AAC GTT CAG GTC AAT CCG GAC TTC TTA CCA
Gln Asp Thr Gln Pro Asn Asn Val Gln Val Asn Pro Asp Phe Leu Pro
                                                                            4500

4530
GAC AAT TGC CGG AGG TCA GTT CCA GGG AAC AAA TCA GGC AAA TTG GTC ACT GGA
CTG TTA ACG GCC TCC CAA GGT CCC TTG ACC AGT CCG TTT AAC CAG TGA CCT
Leu Leu Thr Ala Ser Ser Gln Pro Gly Thr Leu Phe Ser Pro Asn Gln Trp Pro
                                                                            4560

4590
CTA ATG CAC AAC GGC AAT CGC TAG TGA CAT GGA TAA CAA CAC TAA CAA TGG
GAT TAC GTG TTG CCG TTA GCG ATC GTA ACT GTA CCT ATT GTT CTC AGT GTT ACC
Asp Tyr Val Leu Pro Leu Ala Ile Thr Val Pro Ile Val Leu Ser Val Thr
                                                                            4620
```

```
                                                                    4650                                                                4680
AAT CCT GAA CGG TAA CCT TAG GGT TAC GTG TTC TTG TTT GTC CGG AAC TTC CGA CCC AAA
TTA GGA CTT GCC ATT GGA ATC CCA ATG CAC AAG AAC AAA CAG AAG CCT TTG AAG GCT GGG TTT
Leu Gly Leu Ala Ile Gly Ile Pro Met His Lys Asn Lys Gln Ala Leu Lys Ala Gly Phe 4710                                                                4740
CGC GAT AGT TTG GTT TTC CAA CTA CAC AAC TGG TTT CGC CAA CCA TCA CAG AAA TTC CTT
GCG CTA TCA AAC CAA AAG GTT GAT GTG TTG ACC AAA GCG GTT GGT AGT GTC TTT AAG GAA
Ala Leu Ser Asn Gln Lys Val Asp Val Leu Thr Lys Ala Val Gly Ser Val Phe Lys Glu 4770                                                                4800
TAG TAA TTG GCG TGT CCA TAG TCA GTT CGA CGC TTT GCG AAG TTT GTT TGG TCA CGC CGA
ATC ATT AAC CGC ACA GGT ATC AGT CAA GCT CGA AAA GCG CGC TTG AAA CAA ACC AGT GCG GCT
Ile Ile Asn Arg Thr Gly Ile Ser Gln Ala Pro Lys Arg Leu Lys Gln Thr Ser Ala Ala 4830                                                                4860
TTT GGT CCT CGT GGG GCA GGT GGT CAT GTA CGA GGA TTC GGT CCC CGA GGA TTC GGT GGT CAC
AAA CCA GGA GCA CCC CGT CCA CCA GTA CAT GCT CCT AAG CCA GGG GCT CCT AAG CCA CCA GTG
Lys Pro Gly Ala Pro Arg Pro Pro Val His Ala Pro Lys Pro Gly Ala Pro Lys Pro Pro Val

GTT GGT GGA TTT TTT GGG CGA ATCATAAATACTTTAGCTTCGATTTCAATTTTGCAATAATGACAAAATG
CAA CCA CCT AAA AAA CCC GCT TAGTATTTATGAAATCGAAGCTAAAGTTAAACGTTATTACTGTTTTTAC
Gln Pro Pro Lys Lys Pro Ala End            *        **      **       *       **        **    *

GTGAAAATGGCGATCCTGCAACAGTGATCGGTTGTGGATGGAGGAGGAGGTTCTGGTGTTGTGGAGTGGGGATGTGCGGG
CACTTTTACCGCTAGGACGTTGTCACTAGCCAACACCTACCTCCTCCAAGACCACAACACCTCACCCCCTACACGCCCC
```

FIG.6N ns
METHODS AND COMPOSITIONS FOR PRODUCTION OF MYCOPLASMAL ADHESINS

The Government may own certain rights in this invention pursuant to National Institute of Health, Grant Number AI 18540, awarded by the Department of Health & Human Sciences.

This application is a divisional of U.S. Ser. No. 07/118,967, filed Nov. 10, 1987 now U.S. Pat. No. 5,026,636.

This application is related to co-pending U.S. application Ser. No. 07/004/767, which is incorporated herein by reference.

BACKGROUND OF THE INVENTION

1. FIELD OF THE INVENTION

This invention relates to the molecular cloning of the gene encoding *Mycoplasma pneumonias* P1 cytadhesin protein. This protein mediates mycoplasmal colonization of host respiratory epithelium and is a critical virulence determinant. By the present invention, a complete DNA sequence of the complete P1 gene as well as a deduced amino acid sequence of the P1 cytadhesin protein is presented for the first time. In addition, clones expressing *M. pneumonias* peptides are provided. Those peptides contain the functional cytadhesin epitopes and have been used to localize the cytadhesin binding domain of P1.

2. DESCRIPTION OF THE RELATED ART

*M. pneumonias* is a non-invasive pathogen that colonizes the mucosal surface of the respiratory tract and causes a primary, atypical pneumonia. Although this disease appears to occur most frequently in young adults and children, its incidence in the general population may be underestimated because the symptoms are often relatively mild and diagnostic procedures are suboptimal.

*M. pneumonias* initiates infection by colonizing cells of the respiratory epithelium. This colonization is mediated by a specialized tip-like organnelle containing clusters of a surface-localized, trypsin sensitive protein designated P1. Numerous studies show P1 to be a critical virulence determinant. For example, mutants of *M. pneumonlae* that lack P1 or are unable to mobilize and anchor P1 at the tip are avirulent. In addition, treatment of virulent *M. pneumonias* with trypsin abrogates adherence to the respiratory epithelium. Finally, monoclonal antibodies to P1 have been shown to block *M. pneumoniae* cytadherence. Plummer, et al., *Infect. Immun.*, 53:398–403 (1986).

Unfortunately, despite the critical importance of P1 as a mycoplasmal virulence determinant, efforts to provide a cloned gene encoding the P1 cytadhesin have been generally unsatisfactory. For example, Trevino, et al., *Infect. Immun.*, 53:129-134 (1986), describe an attempt to clone *M. pneumonias* antigens by constructing an *M. pneumonias* genomic library using lambda phage EMBL3 as the vector and immunoscreening the library with adsorbed anti-*M. pneumonias* serum. Although this procedure produced several clones exhibiting antigenic cross-reactivity with *M. pneumonias* P1, none of the clones reacted with monoclonal antibodies specific for critical antigenic determinants of P1 shown by the present inventors to mediate cytadherence. Moreover, the largest immunoreactive protein identified had a molecular weight of only 140 kDa. In contrast, native P1 has a molecular weight of approximately 165 kDa. Therefore, it could not be definitely established whether or not the 140 kDa protein was a product of the structural P1 gene. The approach was then abandoned.

Since the P1 cytadhesin is probably the most important mediator of mycoplasma cytadsorption, further elucidation of the structure of this molecule is likely to provide information essential for a complete understanding of the role of cytadherence in pathogenesis of mycoplasmal disease. This goal can be achieved most readily by cloning and sequencing the structural gene encoding P1. Furthermore, recent studies have shown that adherence of mycoplasma to respiratory epithelium can be inhibited by certain antibodies directed against cytadhesin epitopes of P1. Therefore, vaccines comprising recombinant P1 protein or selected cytadhesin polypeptides derived from recombinant P1 are likely to prove effective in preventing mycoplasmal infection. In addition, the availability of the complete gene sequence and deduced amino acid sequence for *M. pneumonias* P1 will allow one to map critical antigenic epitopes and produce selected synthetic peptides useful as diagnostic probes or vaccines.

SUMMARY OF THE INVENTION

By the present invention, the cloning and DNA sequencing of the complete P1 gene is described for the first time. In addition, the complete amino sequence of the P1 protein is provided. The invention also provides recombinant P1 polypeptides, including polypeptides expressed as fusion proteins comprising cytadhesin epitopes. Accordingly, in a general and overall scope, the present invention comprises recombinant clones encoding P1, recombinant DNA sequences suitable for use as hybridization probes to assist cloning of genes encoding P1 and other mycoplasmal cytadhesins, methods for isolating such genes, and recombinant P1 polypeptides.

More particularly, the invention relates to substantially purified nucleic acid molecules comprising a nucleotide sequence encoding the P1 protein or portion of the C-terminal portion thereof. Of course, absolute purification of the nucleic acid molecule is not necessary. Rather, the term "substantially purified" is intended to distinguish the claimed species from species found in nature. Moreover, it will be appreciated that there is no requirement that the nucleic acid encode a complete P1 protein. All that is required is that the molecule encode at least a portion of the C-terminal portion of the P1 protein. For the purposes of the present invention, a C-terminal portion of P1 is defined as the portion of P1 encoded by nucleotides downstream from nucleotide 2440.

In a further embodiment, the substantially purified nucleic acid molecule encodes a P1 protein having molecular weight of about 165-170 kDa. In yet still a further embodiment, the invention relates to a nucleic acid molecule wherein the nucleotide sequence is defined as a nucleotide sequence encoding the amino acid sequence of FIGS. 6A–6N (SEQ ID NO. 9 or SEQ ID NO. 10). Although the term nucleic acid is meant to include both ribonucleic acid (RNA) and deoxyribonucleic acid (DNA), DNA is preferred for the purposes of the present invention. Accordingly, in one embodiment, the nucleic acid is described as DNA.

In addition, the invention provides a substantially purified nucleic acid molecule comprising a nucleotide sequence encoding an *M. pneumonias* P1 polypeptide having a cytadhesin epitope. For purposes of the present invention, a polypeptide is defined as a peptide of more than one amino acid, and a P1 cytadhesin epitope is considered to be any P1 polypeptide which binds to an antibody capable of inhibiting P1 mediated cytadherence or is itself capable of competitively inhibiting P1 mediated cytadherence. For example, a more specific embodiment relates to a nucleic acid molecule wherein the cytadhesin epitope encoded is capable of reacting immunologically with monoclonal antibody 5B8, produced by ATCC#HB 9586.

Similarly, an additional embodiment is directed toward a nucleic acid molecule where the cytadhesin peptide is capable of reacting immunologically with monoclonal antibody 6E7, produced by ATCC#HB 8420. Further embodiments of the invention relate to nucleic acid molecules comprising DNA sequences encoding *M. pneumonias* P1 polypeptides of at least thirteen amino acids in length. More specifically, the invention provides for nucleic acid molecules wherein the P1 polypeptide comprises at least the particular amino acid sequence of the thirteen amino acid cytadhesin epitope described by the present inventors, or the amino acid sequences corresponding to those expressed by phage clones P1-7, P1-9, and P1-10. These amino acid sequences are described by claims 8, 9, 10, and 11, respectively.

Of course, as those of skill in the art will appreciate, the DNA sequences claimed are not required to be actively expressing mycoplasmal P1 polypeptides or in a proper expression vector or expression frame to express the polypeptide. In addition, due to the redundancy of the genetic code, a number of nucleotide sequences may encode the indicated amino acid sequences. Any such nucleotide sequence is considered to be within the scope of the present invention. Moreover, those of skill in the art will appreciate that, in some cases, conservative amino acid substitutions may allow the production of a polypeptide which has a slightly different amino acid sequence than any of those recited in the claims, but has essentially identical function. Such polypeptides are considered to be functional equivalents of the polypeptides described herein and nucleotide sequences encoding such polypeptides are considered to be within the scope of the present claims.

Additional embodiments of the invention are directed towards DNA vectors comprising any one of the DNA molecules described above as well as toward bacterial strains comprising such recombinant vectors. In a more particular embodiment, the bacterial strain is defined as *E.coli.*

A further embodiment of the invention is directed towards DNA molecules comprising a DNA sequence which includes at least a tetradecameric portion of the DNA sequence of FIGS. 6A-6N. These DNA molecules are believed to possess a number of utilities. First, they may be used as hybridization probes to assist in cloning the P1 gene from *M. pneumonias.* In addition, it is contemplated that they may be used to detect homologous nucleotide sequences in other mycoplasmal species, and thus aid in cloning of cytadhesin genes from such species, *M. genitalium,* for example. Of course, in some cases they may also be used to direct synthesis of the polypeptides encoded.

In more specific embodiments of this aspect of the invention, particular nucleotides sequences are claimed. For example, embodiments directed to DNA molecules wherein the DNA sequence comprises nucleotides 178 to 192 or 196 to 213 of FIG. 6A are essentially directed to the 14-mer and 18-mer probes encoding the amino acids shown in FIG. 2A or 2B, respectively. A further embodiment, directed towards the DNA sequence comprising nucleotides −70 to 258 of the DNA sequence of FIG. 6A is essentially directed towards the nucleotide sequence of the Hae III restriction fragment described herein. A still further embodiment is directed to the ECORI/Pst I restriction fragment (nucleotides −204 to 911) used by the present inventors to isolate the P1 gene. Of course, yet another embodiment is directed to the DNA fragment containing the complete structural gene itself. Additional embodiments are directed to the DNA molecule encoding the thirteen amino acid cytadhesin epitope (nucleotides 4148-4185) and to DNA sequence comprising the DNA inserts of phage clones P1-7 (nucleotides 4067-4185), P1-9 (nucleotides 4148-4881), and P1-10 (nucleotides 4202-4881), respectively. Yet still a further embodiment is directed to a DNA sequence comprising at least the transcribed portion of the DNA sequence of FIGS. 6A-6N. Yet still a further embodiment is directed to the DNA sequence of FIGS. 6A-6N.

It will be readily apparent to those skilled in the art that FIGS. 6A-6N depicts both the coding and noncoding strand of the P1 DNA. It should be expressly pointed out that the claims of the present invention are not limited to double stranded DNA molecules, but are intended to encompass both double stranded and single stranded molecules, since, in many systems, either strand may be used as a nucleotide probe and one strand may easily be produced from its complementary strand. The only requirement is that the DNA molecule include the specified nucleotide sequence.

In addition, although certain embodiments refer only to DNA molecules, those of skill in the art will also appreciate that the DNA sequences of the present invention can easily be transcribed into a corresponding RNA molecule. Therefore, RNA molecules corresponding to the DNA sequences of the present invention are considered to be functional equivalents of such DNA molecules and are intended to be encompassed by the present claims.

Additional embodiments of the invention relate to DNA molecules capable of hybridizing to the recombinant insert of the 6 kbp EcoRI fragment designated plasmid pMPM P1 under selected hybridization conditions, said molecules suitable for use as hybridization probes. For example, one embodiment is directed toward a DNA molecule capable of hybridizing to the recombinant insert of plasmid pMPM P1, obtainable from ATCC#67560 under moderately stringent hybridization conditions while another embodiment is directed toward a DNA molecule capable of hybridizing to the recombinant insert of plasmid pMPM P1, obtainable from ATCC#67560 under stringent hybridization conditions. For the purposes of the present invention, such conditions are described as moderately stringent in that they allow detection of a nucleotide sequence at least 14 nucleotides in length having at least approximately 75% homology with the sequence of the nucleotide probe used. Stringent hybridization conditions are defined as conditions wherein the probe detects nucleotide sequences at least 14 nucleotides in length having a homology greater than about 90%. The conditions necessary for hybridization of a particular probe to a particular nucleotide sequence having a specified degree of homology may be determined by referring to *Nucleic Acid Hybridization, A Practical Approach,* Hames and Higgins, eds., IRL Press, Oxford and Washington, 1985, or Wood, et al., PNAS, 82:1585-1588 (1985), both incorporated herein by reference.

In addition, claims are directed toward recombinant DNA vectors comprising the claimed DNA molecules as well as bacterial cells comprising such recombinant vectors. In a more particular embodiment, the bacterial cells are defined as *E.coli*.

The invention also includes polypeptide fragments of *M. pneumonias* having *M. pneumonias* P1 cytadhesin epitopes. More specific embodiments are directed toward polypeptides further defined as being capable of immunospecifically binding to monoclonal antibody 6E7, ATCC#HB 8420. Similarly, an additional specific embodiment is directed towards polypeptides defined as capable of immunospecifically binding to monoclonal antibody 5B8, ATCC# accession number HB 9586, deposited under the Budapest Treaty with the American Type Culture Collection, Rockville, Maryland. Of course, where the recombinant polypeptide is encoded by a DNA sequence inserted in a particular type of expression vector, the polypeptide will be expressed as a fusion protein. For example, when lambda gt11 is used as an expression vector, the *M. pneumonias* polypeptide will be expressed in the form of a beta-galactosidase fusion protein. Although such fusion proteins are considered to be polypeptides and, thus, intended to be encompassed by the claims of the present, invention, one embodiment is specifically directed to fusion proteins.

Additional claims are directed towards polypeptides comprising specific sequences as outlined in the claims. of course, recombinant polypeptides are included within the scope of the present invention. Moreover, synthetic polypeptides can be prepared from known amino acid sequences. The present invention is also meant to encompass any synthetic polypeptide comprising the claimed amino acid sequences or polypeptides having conservative amino acid substitutions and essentially identical function. Additional embodiments of the invention relate to vaccines comprising such polypeptides and methods for inducing resistance to *M. pneumonias* infection. Still further embodiments relate to diagnostic kits comprising polypeptides having cytadhesin epitopes.

More specifically, the invention provides for a cytadhesin polypeptide corresponding biologically to that produced by clones P1-7, P1-9 or P1-10, ATCC#40836, 40385 or 40384, respectively. For the purposes of the present invention, a cytadhesin polypeptide corresponding biologically to a polypeptide encoded by an identified recombinant vector is considered to be any polypeptide having similar or identical function to that encoded by the specified recombinant vector. Such peptides may include synthetic peptides, including synthetic peptides having a slightly different amino acid sequence but essentially similar function. In a more specific embodiment, the polypeptides are further defined as *M. pneumonias* P1 polypeptides.

With even more particularity, the invention provides for a number of DNA molecules comprising a recombinant DNA vector which includes the recombinant inserts of phages P1-7, P1-9, P1-10, ATCC#40586, ATCC#40385, ATCC#40384, respectively. The invention also includes a recombinant DNA vector which includes a recombinant insert of plasmid pMPM P1, ATCC#67590 (pending). Bacterial strains comprising recombinant vectors which include such inserts are also included.

Finally, yet another feature of the present invention relates to a method for screening mycoplasmal DNA for DNA sequences that correspond to those of *M. pneumonias* P1, using the novel nucleotide sequences of the present invention. This method essentially comprises fractionating mycoplasmal DNA to produce DNA fragments; separating the DNA fragments according to their sizes or molecular weights; hybridizing the DNA fragments with DNA molecules provided by the present invention; and identifying at least one fragment which hybridizes to said DNA molecules by means of a label.

Of course, the method will prove useful for isolation of *M. pneumonias* DNA sequences. However, it may also be useful for screening other Mycoplasmal species for homologous genes encoding *M. pneumonias* P1. For example, the present inventors have observed that portions of the *M. pneumonias* P1 gene are homologous to a gene from *M. genitalium.* Therefore, one embodiment of the present invention relates to screening of *M. genitalium.* The specificity of the novel nucleotides probes will depend, in part, on the hybridization conditions used. For example, where one desires to isolate nucleotide sequences encoding proteins homologous but not identical to *M. pneumonias* P1, less stringent hybridization conditions should be used.

Methods which have proved particularly useful in fragmenting the DNA utilize restriction enzyme digestion or mechanical shearing. However, restriction enzyme digestion was utilized for the practice of the present invention. More particularly, the invention provides for digestion of the mycoplasmal DNA with the restriction enzyme EcoRI.

The fragmented DNA can be separated into recognizable patterns using various methods, the most useful of which take advantage of the varying sizes of discrete DNA fragments. For example, DNA fragments can be separated according to molecular weight by velocity sedimentation through a density gradient or, by molecular size exclusion chromatography. However, for purposes of the present invention, the preferred technique is to separate the DNA fragments by electrophoresis through an agarose or polyacrylamide gel matrix.

The P1 hybridization probe can be conveniently labeled with radioactive nucleotides which allow for ready visualization of the hybridized DNA by autoradiography. Of course, other labeling techniques, including heavy isotopes or biotinylation, may also be used.

It should also be appreciated there is also no absolute requirement that the hybridization probes be derived from cloned *M. pneumonias* P1 DNA. Since the present invention provides the complete gene sequence of *M. pneumonias* P1, various oligonucleotide probes can be synthetically prepared on the basis of the disclosed sequence.

The substantially purified DNA molecules, recombinant DNA cloning vectors, recombinant cells, and recombinant proteins of the present invention may be used to prepare *M. pneumonias* P1 polypeptide fragments or fusion proteins suitable for use as vaccines or reagents for use in diagnostic kits. Furthermore, the substantially purified DNA sequences of the present invention are likely to prove useful as hybridization probes for selectively isolating mycoplasmal cytadhesin genes. Modification of the products of the present invention so as to facilitate their utility in these or other areas is considered to be well within its scope.

CHARACTERISTICS OF DEPOSITED MICROORGANISMS

Recombinant lambda gt11 vectors P1-7, P1-9, and P1-10 comprising clones P1-7, P1-9, and P1-10, respectively. These clones comprise lambda gt11 bacteriophages having a mycoplasmal DNA sequence ligated into the EcoRI site within the beta-galactosidase gene.

*E.coli* HB101 comprising a recombinant pUC 19 plasmid vector having a mycoplasmal DNA insert approximately 6 kbp in length ligated into the EcoRI site (plasmid pMPM P1) has been deposited under the Budapest Treaty with the American Type Culture Collection, Rockville, Maryland, and assigned ATCC accession # 67560.

BRIEF DESCRIPTION OF THE DRAWINGS

FIG. 1 (A) total protein extract from *M. pneumonias*. Arrow indicates the position of P1;

FIG. 1 (B) same sample from FIG. 1 (A) after a single passage through the anti-P1 affinity column;

FIG. 1 (C) protein eluted from the anti-P1 affinity column; and

FIG. 1 (D) P1 after preparative gel electrophoresis and electroelution. Proteins were separated by 7.5% polyacrylamide gel electrophoresis and stained with Coomassie blue.

FIG. 2—The N-terminal 18 amino acid sequence of protein P1 and the 14-mer and 18-mer oligonucleotide probes designed to hybridize to the P1 gene. The 14-mer covers amino acids 1 to 5 and the 18-mer covers amino acids 7 to 12. X=ACGT.

FIG. 3 (A) standard;
FIG. 3 (B) EcoRI;
FIG. 3 (C) Hae III;
FIG. 3 (D) Pst I;
FIG. 3 (E) Hind III;
FIG. 3 (F) BamHI;
FIG. 3 (G) Kpn I; and
FIG. 3 (H) Sal I.

FIG. 4—Southern blot analysis of *M. pneumonias* genome. *M. pneumonias* DNA was digested with Hind III, separated by 0.7% agarose electrophoresis and transferred to nitrocellulose paper according to the method of Southern (Mizusawa, et al., *Nucleic Acids Res.*, 14:1319-1324 (1986)). The nitrocellulose strip was then hybridized to the 14-mer (A) and 18-mer (B) probes labeled with $^{32}P$. A single band (4.3kb) hybridizes to both probes (arrow).

FIGS. 6A-6N—Complete nucleotide sequence and deduced amino acid sequence of the P1 gene. Both the coding and non-coding strand is shown. The presumed starting codon of P1 (ATG) is numbered as 1. In the 5' flanking region, the possible promoter elements (−10 and −35) are underlined. The 18 amino acids which match those determined by protein sequencing of P1 are boxed (nucleotides 178-231). In the 3' flanking region, a sequence with dyad symmetry, which may be a termination signal, is indicated by the arrows and the "*" indicates mismatched sequences in this sequence. The complete P1 gene contains 4881 nucleotides coding for a protein of a calculated 176,288 daltons which includes an apparent leader peptide (see text).

FIG. 8—Location of the ten lambda gt11 clones within the P1 structural gene. The predicted fusion protein size and DNA insert size of each clone are given. Molecular weight values of the *M. pneumonias* fusion proteins were calculated by subtracting the value of the beta-galactosidase protein (116 kD).⊔ indicates the location and dimension of the insert size. The numbers indicate nucleotides encompassed by each clone. A "t" indicates that the clone extends through the end of the P1 gene. As indicated in text, a TGA stop codon exists just downstream from the EV site.

FIGS. 9A-9B—Gene sequence and deduced protein sequence of epitopes involved in cytadherence by *M. pneumonias*. The 13 amino acids within which one epitope is located are underlined. Symbols corresponds to the following: ●, start of clone P1-7; ▌, end of clone P1-7; *, start of clone P1-9; and ∇, start of clone P1-10. The stop codon is indicated by the box.

FIG. 10—Hybridization of $^{32}P$-labeled *M. pneumonias* insert DNA from clone P1-7 to *M. pneumonias* genomic DNA digested with EcoRI (lane A), Hind III (lane B), Pst I (lane C), Sac I (land E), and Sma I (lane E). Molecular weights in kb are shown at the left.

FIG. 11—Immunoblot of cytadhesin fusion proteins using anti-P1 MAbs. Lane A represents total *M. pneumonias* proteins reacted with a pool of the two MAbs designated 5B8 and 6E7 (see text). Lane B is the beta-galactosidase protein reacted with a monoclonal Ab to beta-galactosidase (Promega Biolab, Madison, Wis.). Lanes C and D are clones P1-7 and P1-9, respectively, reacted with MAb6E7. Lane E is clone P1-10 reacted with MAb5B8.

FIGS. 12-I, 12-II, 12-III—Immunophage blot of the ten different clones reacted with acute (I) and convalescent (II,III) gsera of patients infected with *M. pneumonias*. Numbers 7, 9, and 10 indicate clones P1-7, P1-9, and P1-10, respectively.

DETAILED DESCRIPTION OF THE PREFERRED EMBODIMENTS

Figure 3:
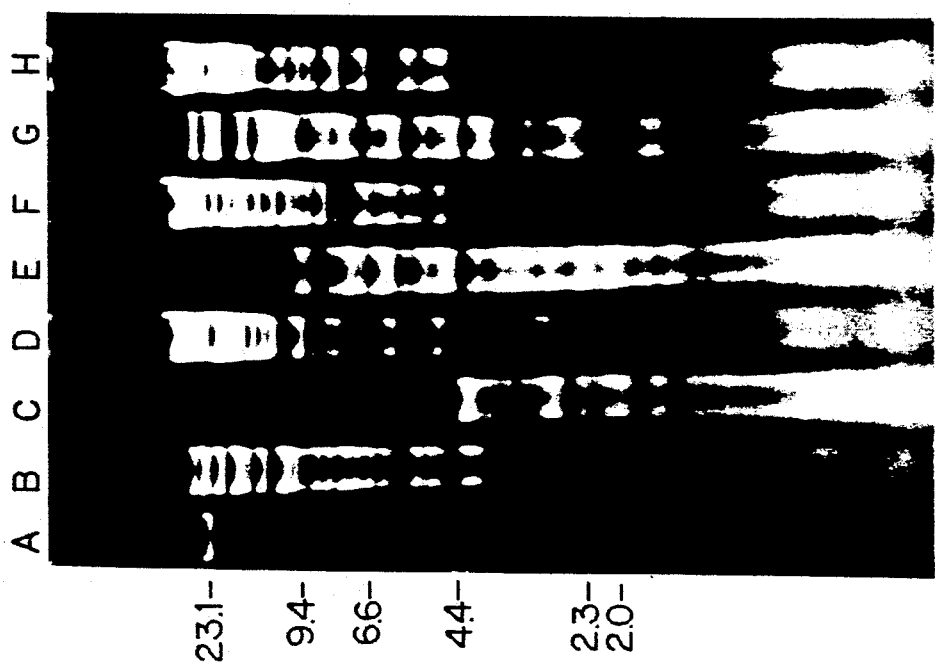
FIG. 3—*M. pneumonias* DNA (12 ug/lane) digested with different restriction enzymes and separated by 0.7% agarose gel electrophoresis.
Figure 1:
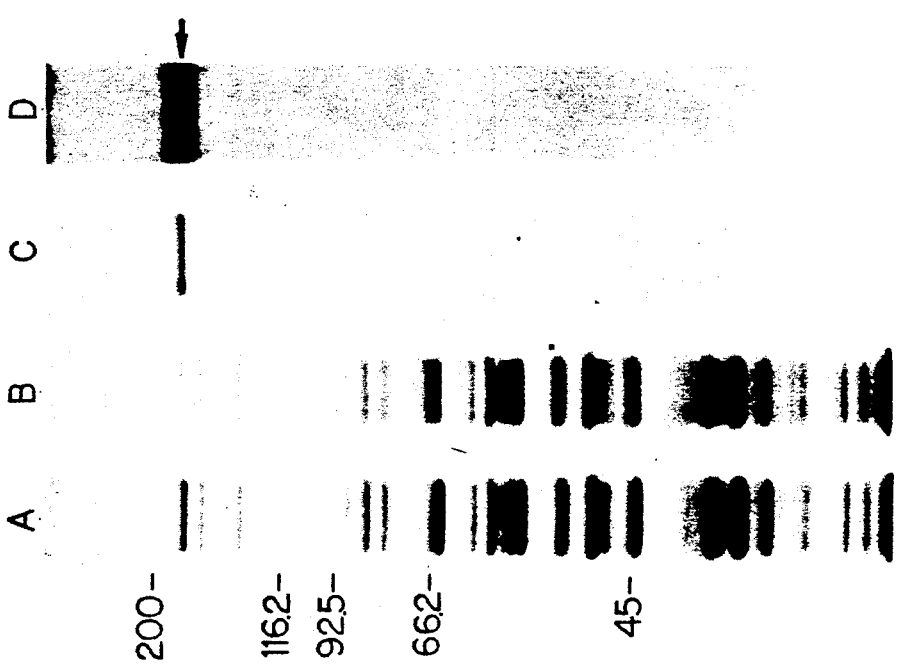
FIG. 1—SDS-polyacrylamide gel electrophoresis analysis of protein samples during the purification of P1.

The present invention describes the isolation and nucleic acid sequence of the gene encoding the P1 cytadhesin protein from *M. pneumonias*, the amino acid sequence of P1, and production of highly antigenic P1 polypeptides, including fusion proteins.

The present invention is disclosed in terms of two general approaches employed by the inventors to isolate clones and identify nucleic acid sequences encoding *M. pneumonias* P1 protein, or highly antigenic *M. pneumonias* polypeptides. The first general approach is primarily directed toward isolating, cloning, and sequencing the complete *M. pneumonias* P1 gene, while the primary goal of the second approach is to identify particular nucleotide sequences encoding the functional cytadhesin domains of P1 and to produce antigenic cytadhesin polypeptides suitable for use as diagnostic reagents or vaccines.

As indicated earlier, past attempts to clone the P1 gene were found to be generally unsatisfactory. This failure was due, at least in part, to lack of a suitable method for unequivocally demonstrating that a particular cloned DNA sequence actually represented the P1 gene. Fortunately, the present inventors have now discovered a technique allowing the complete structural P1 gene to be isolated and cloned. The P1 gene has now been completely sequenced and the nucleotide sequence unequivocally established as the structural P1 gene. In addition, the amino acid sequence of the complete P1 protein has been deduced from the nucleotide sequence.

Accordingly, the general approach described below represents a particularly preferred approach for obtaining recombinant DNA clones containing the complete P1 gene. However, as illustrated below, the method has also been successfully used for cloning partially complete P1 genes.

The technique described below, disclosed for the first time by the present application, is one preferred method for obtaining recombinant DNA molecules and clones of the present invention. of course, variations of this method may also allow the gene to be cloned successfully. It is also possible that other techniques could be successfully used to clone $M.$ pneumonias P1. Any $M.$ pneumonias P1 gene cloned by such procedures is considered to be within the scope of the present invention, unless the claims provide otherwise.

In general, recombinant clones produced in accordance with the present invention are made by first isolating mycoplasmal DNA. Any mycoplasma encoding the P1 protein, may be used as a source of DNA. However, virulent strains of *M. pneumonias* are preferred. These strains include, but are not limited to, *M. pneumonias* isolated from infected humans or animals, as well as defined strains maintained as laboratory cultures. The strain *M. pneumonias* M129 is particularly preferred.

A number of methods for extracting DNA from prokaryotic organisms are known which may, with possible routine modifications within ordinary skill in the art, be used to extract mycoplasmal DNA. A preferred method generally comprises lysing the organisms in a lysing buffer, for example, sodium dodecyl sulfate in phosphate-buffered saline, extracting the DNA from the lysed cell mixture with a suitable organic solvent such as phenol, n-butanol or chloroform and reprecipitating the DNA with a suitable reagent such as ethanol, ethanol-acetate or isopropanol.

The extracted DNA is then fragmented. Any of a number of techniques suitable for producing DNA fragments, such as mechanical shearing or partial or complete restriction enzyme digestion, may be used. However, where a complete clone of the structural gene is desired, it is important to fragment the DNA so as to produce fragments at least about 4.75–5.0 kb.

In general, digestion with restriction enzymes is a preferred method of fragmenting the mycoplasmal DNA. Although any of a number of restriction enzymes may be used (for example, see those listed in *MOLECULAR CLONING*, Maniatis, et al., Cold Spring Harbor Laboratory, Cold Spring Harbor, N.Y., pp. 93–103) under properly selected digestion conditions, the present inventors have discovered that the *M. pneumonias* genome contains an EcoRI site on either side of the P1 structural gene, but not within the gene itself. Therefore, when EcoRI is used as a restriction enzyme, complete digestion of *M. pneumonias* DNA will produce a single DNA fragment containing the entire structural gene. For this reason, it is especially preferred that the *M. pneumonias* DNA be digested to completion with ECORI in cases where a full length structural gene is desired.

Conversely, if one desires to obtain a fragment containing only a portion of the P1 structural gene, complete digestion with Sal I, Pst, BamHI, Kpn I, Sma I, Sac I, Hind III, or Eco RV may be used since the P1 structural gene is now shown to contain restriction sites for these enzymes. Of course, it may be also possible to use these enzymes in partial digestion procedures in cases where a full length P1 gene is desired.

The fragmented DNA can be separated into a recognizable pattern using various methods, the most useful of which take advantage of the varying sizes of the discrete DNA fragments. For example, DNA fragments can be separated according to molecular weight by velocity sedimentation through a density gradient, or by molecular size by gel exclusion chromatography. However, according to a technique preferred for the purposes of the present invention, DNA fragments are separated by electrophoresis through an agarose gel matrix and then transferred to a nitrocellulose sheet so that an exact replica of the DNA fragments in the gel is transferred to the nitrocellulose sheet.

A specific labelled probe is then applied to the nitrocellulose sheet under selected hybridization conditions so as to hybridize with complementary DNA fragments localized on the sheet. Although various labels known to those of skill in the art may be employed, a radioactive probe is preferred. The sheet may then be analyzed by autoradiography to locate particular fragments which hybridize to the probe.

Various hybridization probes may be used to detect the P1 structural gene. For example, in experiments performed in conjunction with development of the present invention, the N-terminal amino acid sequence of the P1 protein was determined and two oligonucleotides based on this sequence (the 14-mer and 18-mer probes described in Example I) were utilized. In subsequent experiments, an EcoRI/Pst I restriction fragment digested from an incomplete P1 clone (62A) was used as a hybridization probe. However, as those of skill in the art will appreciate, any number of suitable hybridization probes can now be prepared, based on secluences contained within the complete P1 gene sequence provided for the first time by the present invention. All that is required is that the DNA fragments to be used as probes be of sufficient length to form a stable duplex or hybrid with the P1 DNA. Such fragments are said to be "hybridizable" in that they are capable of stable duplex formation. Generally, a DNA fragment of at least fourteen nucleotides in length (a tetradecamer) is capable of forming a stable duplex. of course, in practice, it may be sometimes preferable to use a probe containing more nucleotides or alternatively, to use a battery of individual probes to detect a single fragment that hybridizes to each probe in the battery.

In any event, after DNA of the size range containing the desired restriction fragments is identified by the procedure generally described above, the fragment may be removed from the gel by a variety of techniques known to those of ordinary skill in the art (e.g., electroelution, dialysis, etc.) and cloned into an appropriate vector. Although it is likely that the restriction fragment containing the P1 gene could successfully be cloned into several types of vectors, (e.g., cosmids or phage), it is generally preferred to use a plasmid cloning vector, particularly where the desired restriction fragment is smaller than 15 kbp.

After construction of recombinant vectors, the vectors are used to transform an appropriate host. In a preferred embodiment, the host is an *E.coli* cell of a type which is compatible with the selected vector type. However, although the present invention is disclosed in terms of *E.coli* host/vector systems, other host/vector systems are known in the art and may be employed where desired. For example, see those described in *DNA Cloning* (Vol. II), P. M. Glover, ed., IRL Press, Oxford, Washington, D.C. (1985).

Transformation of host cells by the recombined vector is achieved using standard procedures known in the art. For example, where plasmid vectors are employed, transformation is typically achieved by permeabilizing competent cells with calcium and contacting the permeabilized cells with the recombinant vector DNA. Where bacteriophage vectors are employed, one may additionally choose to package the recombinant phage with phage coat proteins, which affords direct transformation capability through cell infection with a resultant increase in transformation efficiency.

Once the cells are successfully transformed with the recombinant vector DNA, they are culture plated to provide individual recombinant clonal colonies or plaques, a portion of which may express proteins or peptides encoded by the *M. pneumonias* P1 genome. In addition, clones may be used as a source of *M. pneumonias* DNA suitable for subcloning, sequencing studies or use as hybridization probes.

The second general approach utilized by the present inventors relates to cloning and expression of *M. pneumonias* DNA encoding polypeptides having a cytadhesin epitope. The polypeptides so produced may be used as diagnostic reagents or vaccines.

The focus of this approach differs somewhat from that described above in that it is generally directed toward, isolation and expression of *M. pneumonias* DNA that encodes a particular functional domain of the P1 protein, the domain responsible for cytadherence. In general then, this second approach involves fragmenting *M. pneumonias* DNA by procedures similar to those described above and using the fragmented DNA to construct an *M. pneumonias* DNA library or clone bank which is then screened with a reagent specific for clones encoding cytadhesin epitopes.

The DNA libraries may generally be constructed in either plasmids or bacteriophage, however, where expression of the cloned gene sequence is desired, it is preferred that the library be constructed in an expression vector. The lambda gt11 expression vector is particularly preferred where expression of the cloned gene is desired because use of lambda gt11 has been found to ameliorate several problems generally associated with production of foreign proteins in *E.coli*. (See Huynh, et al., In DNA Cloning (Vol. I), E. M. Glover, ed., IRL Press, Oxford, Washington, D.C. (1985) and incorporated herein by reference.) Of course, it is contemplated that a number of other vectors could also be used to generate and/or express the *M. pneumonias* DNA library.

The library may be screened for clones containing DNA sequences encoding the cytadhesin domain of P1 by various procedures so long as the screening reagents used allow isolation of a recombinant DNA clone encoding at least a portion of the cytadhesin domain. For example, the present inventors used monoclonal antibodies previously shown to recognize the cytadhesin binding domain of *M. pneumonias* P1 (See Morrison-Plummer, et al., *Infect. Immun.*, 55:49-56 (1987)). Notably, those antibodies do not react with the DNA clones described by Trevino, et al.

Of course, since the present disclosure describes the nucleic acid sequence of the critical regions of the P1 gene, nucleic acid hybridization probes that selectively hybridize to these regions of the P1 genome may also be used for screening. (For examples of a nucleic acid screening procedure, see Huynh, et al., In DNA Cloning (Vol. I), E. M. Glover, ed., IRL Press, Oxford, Washington, D.C. (1985)). However, where one desires to screen with specific nucleic acid probes, lambda gt10 may be a preferred vector.

Once clones containing the *M. pneumonias* cytadhesin epitopes are isolated, they may then be expanded and used as a source of *M. pneumonias* DNA for sequencing studies. The sequence of the DNA inserts of the selected clones can then be compared with the complete DNA sequence of the P1 gene provided for the first time by the present invention. In this manner, the cloned inserts can be unequivocally identified as encoding all or part of the P1 protein.

DNA or deduced amino acid sequences from a battery of clones may then be correlated with the antigenic phenotype of the polypeptides produced by such clones to precisely map the location of nucleotide sequences encoding particular antigenic epitopes. Moreover, certain monoclonal antibodies specific for the P1 protein have been shown to inhibit cytadherence of *M. pneumonias* and, therefore, are specific for the functional domain of P1 that mediates cytadherence. When these monoclonal antibodies are used for screening, the epitopes involved in mediating cytadherence can be mapped as well.

The recombinant DNA clones encoding all or part of the functional domain responsible for cytadherence are particularly valuable. First, the peptides expressed by such clones may be used as immunodiagnostic reagents to detect *M. pneumonias* infection. More importantly, the peptides may be incorporated into an antimycoplasmal vaccine. In addition, antigenic peptides comprising the cytadhesin specific epitopes can be synthesized, on the basis of the amino acid sequences deduced from the mapped nucleotide sequence and used as vaccines or antigens for immunodiagnostic tests.

Finally, it should be pointed out that, for practical reasons, it may often be easier to demonstrate the P1 cytadhesin epitopes using a monoclonal antibody since polyclonal antiserum will usually contain antibody molecules specific for regions of the P1 protein not associated with the cytadhesin domain as well as antibody molecules specific for cytadhesin epitopes. However, polyclonal antiserum capable of inhibiting P1 mediated cytadherence may also be used to demonstrate presence of the cytadhesin epitopes by a number of techniques generally known to those of skill in the art. For example, selected P1 polypeptides may be used to extensively adsorb the polyclonal antiserum and adsorbed and nonadsorbed antiserum compared for the ability to inhibit cytadherence. By this procedure, specific polypeptides capable of significantly reducing the antibody mediated inhibition of P1 mediated cytadherence may be considered to express cytadhesin epitopes. In addition, cytadhesin epitopes may be demonstrated directly by their ability to competitively inhibit P1 mediated cytadherence in any of a number of experimental systems commonly used to measure cytadherence, described by Morrison-Plummer, et al., *Infect. Immun.*, 53:398 (1986), or Krause and Baseman, *Infect. Immun.*, 39:1180-1186 (1983).

Although the methodology described herein contains sufficient detail to enable one skilled in the art to practice the present invention, a commercially available technical manual entitled *MOLECULAR CLONING* (Maniatis, et al., Cold Spring Harbor Laboratory, Cold Spring Harbor, New York) may provide additional details useful to assist practice of some aspects of the invention. Accordingly, this manual is incorporated herein by reference.

The following examples are designed to illustrate certain aspects of the present invention. However, they should not be construed as limiting the claims thereof.

EXAMPLE I

Isolation of a Recombinant Clone That Contains a DNA Sequence Encoding *M. pneumoniae* P1

This example is designed to illustrate the actual steps followed by the inventors in obtaining a specific recombinint clone that contained a DNA sequence encoding the mycoplasma P1 protein. However, this example is not meant to represent the only procedure for cloning the P1 gene.

A. Culture of Mycoplasma And *E. Coli*

Virulent hemadsorbing *Mycoplasma pneumonias* strain M129 in the sixteenth broth passage was grown at 37° C. in 32 ounce glass prescription bottles containing 70 ml of Edward medium (Edward, *J. Gen. Microbial.*, 1:238–243 (1947)). Glass adherent mycoplasmas were washed four times with phosphate buffered saline (PBS; pH 7.2) and collected by centrifugation (9,500×g 20 min.). Cells were harvested 72 hours after inoculation and stored at −70° C.

*Escherichia coli* strain HB101, DH5 alpha, and JM 107 were purchased from commercial sources and grown in LB broth (10 g/l Bacto-tryptone, 5 g/l Bacto-yeast extract, 10 g/l NaCl, pH 7.5).

B. Purification of P1 Protein by Affinity Chromatography

The P1 protein was purified by antibody affinity chromatography according to the method described by Leith and Baseman, *J. Bacteriol.*, 157:678–680 (1984). Briefly, this method was as follows.

Four anti-P1 monoclonal antibodies secreted by hybridomas (Morrison-Plummer, et al., *Infect. Immun.*, 55:49–56 (1987); Morrison-Plummer, et al., *Infect. Immun.*, 53:398–403 (1986)) were combined and purified by protein A-Sephadex column chromatography. Anti-P1 affinity columns were prepared by coupling 50 mg of purified anti-P1 antibody to 15 ml of cyanogen bromide activated Sephadex gel (Pharmacia, P1 Piscataway, N.J.).

Pellets from 100 bottles of *M. pneumonias* were suspended in 50 ml of 20 mM Tris-HCl (pH 8.0), 0.2% sodium deoxycholate (Fisher Scientific), 0.1% sodium dodecyl sulfate (BDH Chemicals, Poole, England), 10 mM EDTA, and 0.2% Triton-X-100 containing 1 mM phenylmethylsulfonyl fluoride. Solubilization of proteins was assisted by passing the cell suspension through successively smaller gauge needles (22 to 27 gauge). Insoluble material was removed by centrifugation at 100,000×g for 30 minutes.

Solubilized proteins were applied to the affinity column at 4° C. and washed with 5 column volumes of the same buffer minus sodium deoxycholate. Bound protein was eluted with 0.1M acetic acid (pH 3) containing 0.15M NaCl and 0.1% SDS. The eluted protein was immediately neutralized with 1.0M Tris and concentrated in a pressure ultrafiltration concentrator (Amicon, Denvers, Mass.).

As shown in FIG. 1 (panel's A–C), this procedure selectively enriched for the *Mycoplasma pneumonias* cytadhesin protein P1 (165 kilodaltons). Approximately 400 ug of P1 protein was recovered after the immunoaffinity step from an initial *M. pneumonias* extract containing 300 mg total protein.

As an additional purification step, the affinity column-purified P1 was further processed by preparative gel electrophoresis through a 5% polyacrylamide-SDS gel. The gel was stained with Coomassie blue and the P1 protein band was cut out of the gel and electroeluted according to the procedure of Hunkapiller, et al. (In Methods in Enzymology, C. H. W. Hirs and S. N. Timasheff (eds.) pp. 227–236 (1983)). About 60% recovery was achieved after 24 hours of elution at room temperature in 50 MM ammonium carbonate containing 0.1% SDS. The eluted protein was then precipitated in 80% methanol to remove SDS. SDS-PAGE analysis of the recovered P1 revealed that the sample contained intact P1 protein (FIG. 1D), and the gel was deliberately overloaded to show the purity of the sample. Finally, the purified protein was shown to be P1 since it reacted with anti-P1 monoclonal antibodies in Western blot analyses (data not shown).

C. Determination of the N-Terminal Amino Acid Sequence of P1 Protein and Preparation of Specific Oligonucleotide Probes The purified P1 protein was sequenced from the amino terminus with a gas phase protein sequencer. Approximately 50 ug of purified P1 was used (300 pmole) for each sequence analysis. Three separate determinations yielded the sequence shown in FIG. 2.

The N-terminal amino sequence was used to deduce sequences for oligonucleotide probes. Two oligonucleotide probes complementary to all the possible mRNA combinations encoding different portions of the protein were synthesized, a 14-mer corresponding to amino acids 1–5 and a 18-mer corresponding to amino acids 7–12 (FIG. 2). The present inventors used both C and T in the third position of the trypotophan codon of the 18 bp oligonucleotide in order to ensure hybridization with the probe in the event that *M. pneumonias* uses TGA (a stop codon in bacterial and eukaryotic systems) rather than TGG to encode tryptophan. The oligonucleotides were synthesized in the Department of Biochemistry, Baylor College of Medicine according to a procedure similar to that described by Alvarado-Urbina, et al., *Science*, 214:270–274 (1981), incorporated herein by reference, and purified by electrophoresis in 20% polyacrylamide gel containing 8M urea (Berent, et al., *Biotech.*, 3:208–220 (1985)). For use as hybridization probes, the oligonucleotides were labeled at the 51′ end with Y-$P^{32}$-ATP by the T4-polynucleotide kinase reaction (Maniatis, ei al., *MOLECULAR CLONING*, Cold Spring Harbor Laboratory, Cold Spring Harbor, N.Y. (1982), pp. 122–127).

D. Southern Blot Analysis of *M. pneumonias* DNA

*M. pneumonias* DNA was prepared from exponentially growing cells according to the following procedure. Pellets of *M. pneumonias* were suspended in 2.7 ml of PBS, lysed by the addition of 0.3 ml of 10% sodium dodecyl sulfate (SDS) and incubated with 10 ug of RNase for 30 minutes at 37° C. Preparations were extracted three times with an equal volume of redistilled phenol (equilibrated with 100 mM Tris [pH 8.0] −10 mM EDTA [TE]) followed by dialysis overnight at 4° C. against a total of 6 liters of sterile TE. Twelve ug of DNA was digested to completion with EcoRI, Hae III, Pst I, Hind III, BamHI, Kpn I or Sal I prior to electrophoretic separation on 0.7% agarose gels. Gels were stained with ethidium bromide and photographed under UV illumination (FIG. 3).

The gels were then analyzed according to the procedure of Southern, *J. Mol. Biol.*, 98:503–519 (1975), incorporated herein by reference. Briefly, DNA was transferred to nitrocellulose filter paper with 20×SSC (0.3M sodium citrate, pH 7.0, 3M NaCl), rinsed once with 6×SSC, then baked at 80° C. for 2 hours under vacuum. Filters were prehybridized overnight at 37° C. in 20 ml of prehybridization solution containing 6×SSC, 60 mM sodium phosphate (pH 7.0), 5×Denhardt's solution (bovine serum albumin, polyvinylpyrolidone, Ficoll at 1 mg/ml) and 0.1 mg/ml of denatured herring sperm DNA.

Hybridizations with the 14 base pair [bp] and 18 base pair [bp] oligonucleotide probes were carried out for 12 hours in 10 ml of prehybridization solution plus 10% dextran sulfate and $^{32}P$ labeled oligonucleotide probes ($3\times10^8$ cpm) at 25° C. (14 bp, 14-mer) or 37° C. (18 bp, 18-mer). After incubation, filters were rinsed twice with 6×SSC at 4° C. (30 min. each), then washed twice in wash solution (3M tetramethylammonium chloride, 50 mM Tris-HCl, pH 8.0, 2 mM EDTA, 0.1% SDS) at the appropriate temperature (14-mer at 37° C. and 18-mer at 45° C.) for 20 min. according to the procedure of Wood, et al., *Proc. Nat. Acad. Sci., U.S.A.*, 82:1585–1588 (1985). After washing, filters were rinsed in 6×SSC at 4° C., dried and exposed to X-ray film using an intensifying screen.

Both probes hybridized to several DNA bands in each digestion, possibly because the probes were comprised of a mixture of oligonucleotides formulated to react with all possible nucleotide sequences that could encode the 12 N-terminal amino acids. A 4.3 kb Hind III fragment hybridized most intensely to both the 14-mer and 18-mer (FIG. 4) strongly implicating this DNA fragment as containing the N-terminal sequence of P1.

E. Cloning DNA Fragments Encoding *M. pneumonias* P1 Protein

To clone the DNA fragment described above, *M. pneumonias* DNA was digested with Hind III, separated by agarose gel electrophoresis, and stained briefly with ethidium bromide. DNA in the 4.3 kb size range was eluted from the gel by electrophoresis onto DE-81 paper, eluted from the paper with 20 mM Tris-HCl, pH 8.0, and 1.5M NaCl, then precipitated with ethanol and redissolved in TE buffer.

The DNA was then ligated into the Hind III site of pUC 9. For this procedure, the plasmid was digested with an appropriate restriction enzyme (Hind III) and the 51' end phosphate removed by calf intestinal alkaline phosphatase according to the procedure described on page 133 of Maniatis, et al., *MOLECULAR CLONING*, Cold Spring Harbor Laboratory, Cold Spring Harbor, N.Y. (1982). Mycoplasma DNA and vector were mixed at 1:1 molar ratio and ligated at room temperature for 4 hours with T4 DNA ligase. After incubation, the reaction was stopped by adding EDTA to 10 mM, diluted 5-fold with distilled $H_2O$.

The ligated plasmid DNA was then used to transform competent HB101 or DH5 alpha *E.coli* cells according to the manufacturer's instructions (BRL, Bethesda, Md.). Transformants were selected on LB agar plates containing 50 ug/ml of ampicillin. About 5,000 transformants were obtained, of which 200 individual colonies were picked and grown overnight in 5 ml of LB broth containing 50 ug/ml of ampicillin. Plasmid DNA was isolated from overnight cultures by the alkaline lysis method (Ish-Horowicz and Burke, *Nucleic Acid Res.*, 9:2989–2998 (1981)) and analyzed on agarose gels.

Figure 5:
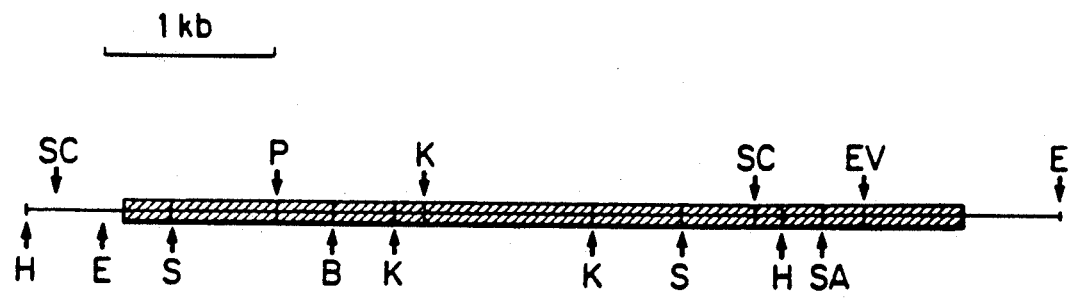
FIG. 5—Restriction enzyme map of the P1 gene. The first clone (62A) contains the 4.3 kb Hind III piece, and the second clone contains the 6 kb EcoRI piece. Both the 14-mer and 18-mer probes hybridize to the DNA at a site very close to the first Sma I site. The crosshatched box represents the P1 structural gene.

To determine which insert-containing plasmids carried the P1 gene, DNAs from about 40 plasmids with inserts in the 4–5 kb range were blotted onto nitrocellulose filters. The filters were then hybridized to the $^{32}P$ labeled 14-mer and 18-mer oligonucleotide probes, washed and exposed to film as described above. Three clones hybridized strongly to both probes. By restriction endonuclease analysis the three clones contained the same insert designated 62A (FIG. 5).

The DNA sequence which hybridized to both probes was narrowed to a 350 bp Hae III restriction fragment by digesting the 62A plasmid with the Hae III, separating the DNA on a 5% polyacrylamide gel, and transferring the DNA from the gel onto nitrocellulose paper for hybridization with each individual probe (data not shown). The 350 bp Hae III piece was subcloned into M13mpl8 and its sequence determined. It contains both the 14-mer and 18-mer sequences, and most importantly the DNA has an open reading frame which codes for the 18 amino acids found by sequencing the amino terminus of the P1 protein (FIGS. 6A–6N). Thus, clone 62A was shown to contain at least a part of the structural gene encoding P1.

However, based upon the location of the sequenced Hae III fragment in the 62A clone, the 4.3 kb Hind III DNA fragment was not large enough to encode the entire 165 kDa P1 protein. Therefore, an EcoRI/Pst I restriction fragment from 62A was used to clone a larger DNA fragment. This procedure was performed as follows:

Plasmid 62A was isolated from overnight cultures by the alkaline lysis method (Ish-Horowicz and Burke, *Nucleic Acids Res.*, 9:2989–2998 (1981)) and digested to completion with a mixture containing 500 units EcoRI and 500 units Pst I. The resulting restriction fragment was purified by agarose gel electrophoresis, labeled by nick translation (Maniatis, et al., *MOLECULAR CLONING*, Cold Spring Harbor Laboratory, Cold Spring Harbor, N.Y. (1982), pp. 109–112) and used to probe Southern blots of *M. pneumonias* DNA digested to completion with EcoRI. This procedure was performed essentially as described above, except that the hybridization conditions were more stringent including a higher temperature of hybridization and wash (65° C.).

By this procedure, an *M. pneumonias* DNA fragment approximately 6 kbp was detected. Accordingly, DNA in this size range was eluted from an agarose gel of the EcoRI-digested DNA by electrophoresis onto DE-81 paper, eluted from the paper with 20 mM Tris-HCl, pH 8.0, and 1.5M NaCl, then precipitated with ethanol and redissolved in TE buffer.

The DNA was then ligated into the EcoRI site of pUC 19, essentially as described above and used to transform E.coli, as described above. Restriction enzyme analysis of the cloned insert indicated that the 6 kbp insert overlapped clone 62A and was sufficiently large to encode the entire P1 protein. The restriction enzyme map depicting both the 4.3 kbp Hind III fragment and the 6 kbp EcoRI fragment is shown in FIG. 5.

EXAMPLE II

Determination of the Complete DNA Sequence of the Gene Encoding Mycoplasma pneumoniae P1 Amino Acid Sequence of the P1 Protein

A. Sequencing of the P1 Gene

DNA sequences were determined by the dideoxy-chain-termination method of Sanger, et al., *Proc. Natl. Acad. Sci., U.S.A.,* 74:5463-5467 (1977). M13 sequencing kits were purchased from BRL and the reactions were performed according to the manufacturer's instructions except deoxy-7-deaza GTP (Boehringer Mannheim, Indianapolis, Ind.) was used in sequencing reactions in place of dGTP (Messing, et al., *Nuc. Acid Res.,* 9:309-321 (1981)). Some DNA fragments were sequenced by subcloning appropriate restriction enzyme fragments into an M13 phage vector (Messing, et al., *Nuc. Acids Res.,* 9:309-321 (1981)) and the single strand DNA purified for use as a sequencing template. To sequence the rest of the P1 gene, a large piece of DNA from the Pst I to the Sal I (see FIG. 5) was subcloned into an M13 vector and a series of deletions from the 3' end were generated by treating the double strand DNA with exonuclease III according to the method of Heinkoff, *Gene,* 28:351-359 (1981). Subclones with progressive deletions were selected for use as sequencing templates. Both strands of the entire P1 gene were sequenced. Nucleic acid and protein computer analyses were performed using the Microgenie program (Beckman, Palo Alto, Caif.). Comparisons of the P1 DNA and deduced protein sequences were to the most recent releases of the NIH Genbank DNA sequence database and the National Biomedical Research Foundation protein sequence database, respectively.

B. Analysis of the P1 Nucleotide Sequence

The nucleotide sequence of the P1 gene is shown in FIGS. 6A-6N. There is an open reading frame of 4881 nucleotides and at the end of the gene is a TAG stop codon followed by 2 in-frame TAA stop codons 21 and 27 bp downstream. This sequence could encode a protein of 1627 amino acids with a calculated molecular weight of 176,288.

The nucleotide sequence includes a possible in frame translation initiation site, ATG, 177 nucleotides from the P1 N-terminal sequence. There are conventional transcription initiation sites at −35 and −10 upstream with a distance of 14 nucleotides between these two consensus sequences (Reznikoff, et al., *Ann. Rev. Genet.,* 19:355-387 (1985)), but no ribosomal binding site is observed between −10 and the initiation codon. This predicts a protein with an extension of 59 amino acids from the N-terminus. Another possible translation initiation codon is the GTG (Gold, et al., *Ann. Rev. Microbiol.,* 35:365-403 (1981)) at position 91. Use of this initiation site would predict a 28 amino acid precursor.

The open reading frame contains the 18 amino acids identified by gas phase sequencing (FIGS. 6A-6N, Box). Comparison of the gas phase sequence with the nucleotide sequence demonstrates that the inventors' hunch that *M. pneumonias* might use this codon to encode tryptophan was correct.

Moreover, it was observed that the 18 amino acids are found at position 60-77 of the deduced protein instead of at the amino terminus of the open reading frame. The reason for this apparent discrepancy could well be that P1, like many outer membrane proteins, is initially synthesized as a precursor (Oliver, *Ann. Rev. Microbial.,* 39:615-648 (1985)). Consistent with this hypothesis is the observation that the extra 59 amino acids found at the amino terminus of the deduced protein appear like a signal peptide; they include positively charged amino acids followed by a stretch of hydrophobic amino acids (Oliver, *Ann. Rev. Microbial.,* 39:615-648 (1985)). If protein P1 is indeed synthesized as a precursor and processed into a mature protein, then the molecular weight of the mature protein would be 169,758 which is very close to the 165 kDa reported earlier [Baseman, et al., *J. Bacteriol.,* 151:1514-1522 (1982); Krause, et al., *Infect. Immun.,* 35:809-817 (1982); Leith and Baseman, *J. Bacteriol.,* 157:678-680 (1984); and Morrison-Plummer, et al., *Infect. Immun.,* 55:49-56 (1987)] and almost identical to the value (168 kDa) determined by Jacobs, et al., *J. Clin. Microbiol.,* 23:517-522 (1986) on SDS-PAGE.

Other relevant features of the sequence include a typical enbacterial promoter (Reznikoff, et al., *Ann. Rev. Genet.,* 19:355-387 (1985)) for RNA polymerase which is upstream of the first ATG codon, at approximately −35 and −10. Also, a not-so-perfect invert repeat sequence is detected 19 base pairs downstream from the TAG stop codon. The inverted repeat sequence is a common feature of an RNA terminator (Rosenberg and Court, *Ann. Rev. Genet.,* 13:319-353 (1979)). However, no typical ribosomal binding site is observed between −10 and the initiation codon.

C. Determination of the Amino Acid Sequence of the P1 Protein

The complete amino acid sequence of the *M. pneumonias* (FIGS. 6A-6N) P1 protein was predicted from the DNA sequence, also shown in FIGS. 6A-6N. The predicted amino acid sequence is consistent with available information about protein P1; the predicted molecular weight of P1 approximates the reported values; and the predicted N-terminal amino acid sequence fits exactly with the gas phase sequence analysis of purified P1 protein. The predicted P1 sequence contains more basic amino acids (Arg+Lys+His=169) than acidic (Asp=Glu=143) (isoelectric focusing data shows that P1 has an isoelectric point at a basic pH). The predicted P1 contains no cysteine and thus has no intramolecular disulfide bonding, a finding which correlates with the previous observation that the P1 position in polyacrylamide gels is not changed after exposure to sample buffer containing reducing agents.

By referring again to FIGS. 6A-6N, it can be seen that the predicted P1 protein has several other interesting features: a) it contains high percentages of hydroxy amino acids (17.7% are serine and threonine); and the high proline content (13 of 26 amino acids) at the carboxy terminus is unusual and may place structural restraints on the protein and assist in regulating the topological organization of the cytadhesin in the membrane [Baseman, et al., *J. Bacteriol.,* 151:1514-1522 (1982); Baseman, et al., In Molecular Basis of Oral Microbial Adhesion, S. E. Mergenhagen and B. Rosan (eds.), (1985); Kahane, et al., *Infect. Immun.*, 49:457-458 (1985); and Krause, et al., *Infect. Immun.*, 35:809-817 (1982)].

It should be noted that FIGS. 6A-6N displays the actual nucleotide sequence determined by sequence analysis of the 6 kbp EcoRI fragment (plasmid pMPM P1) insert obtainable from ATCC#67560. As those of skill in the art will appreciate, due to the redundancy of the genetic code, numerous other nucleotide sequences may be constructed which code for the same amino acid sequence. Therefore, any nucleic acid sequence encoding for the *M. pneumonias* P1 protein as depicted in FIGS. 6A-6N is meant to be included within the scope of the present invention. This includes nucleotide sequences containing either the mycoplasmal (TGA) or traditional (TGG) tryptophan codons.

D. Homology between *M. pneumonias* and Other Proteins Having Known Amino Acid Sequences The deduced amino acid sequence for the P1 protein was compared to known amino acid sequences listed in the National Biomedical Research Foundation protein sequence database. This analysis revealed that the predicted P1 sequence is homologous to coat protein A of bacteriophage Ike (protein P1 amino acid numbers 1308 through 1322 compared to bacteriophage amino acid numbers 240 through 254, 73.3% homology; 257-290 vs. 231-264, 41.2% homology), protein 3A of Brome Mosaic virus (956-979 vs. 133-159, 52% homology), coat protein vp2 and vp3 of mouse polyomavirus (733-746 vs. 24-38, 66.7% homology), and coat protein A precursor of bacteriophage fd, M-13 and F1 (1296-1330 vs. 245-280, 51.3% homology). The 1290-1350 region of P1 also shares extensive homology with cytoskeletal keratin of mammalian species. In addition, two regions of P1 share extensive homology with human fibrinogen alpha chain precursor (337-352 vs. 338-354, 70.6% homology; 822-852 vs. 544-565, 59.1% homology). It is fascinating that parts of the P1 sequence are homologous to specific viral coat proteins, mammalian cytoskeletal keratin and to human fibrinogen alpha chain precursor. These findings may help explain observations of autoimmune-like mechanisms of physiopathology associated with mycoplasma disease (Biberfeld, S., *Clin. Exp. Immunol.*, 8:319-333 (1971); Wise and Watson, *Infect. Immun.*, 48:587-591 (1985)).

E. Analysis of Individual Antigenic Determinants Within the P1 Molecule by Hydrophillicity Plotting Cytadhesin P1 is strongly immunogenic and the appearance of anti-P1 antibodies correlates with resolution of the atypical pneumonias induced by *M. pneumonias*. Therefore, the recombinant P1 protein or selected peptides derived from the P1 protein provide attractive vaccine candidates. The present inventors have performed experiments directed towards mapping individual antigenic sites within the protein. one approach is used to map the antigenic sites and is described below.

Figure 7:
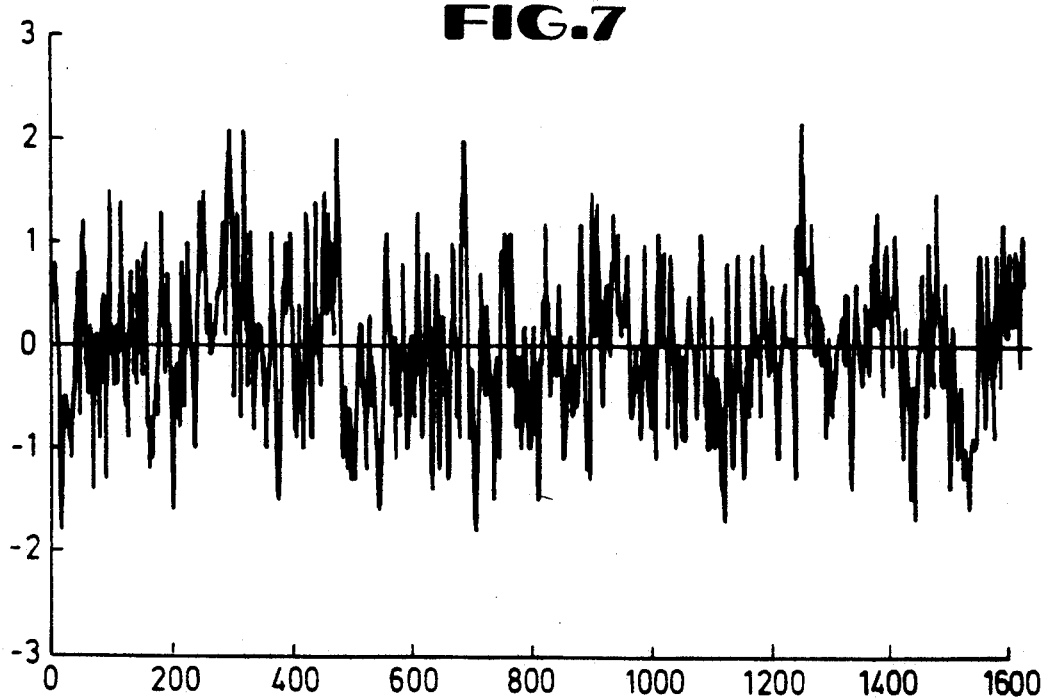
FIG. 7—Plot of hydrophilicity value versus sequence position of P1 according to the method of Hopp and Woods, *Proc. Natl. Acad. Sci., U.S.A.*, 78:3824–3828 (1981). Hydrophilicity values are averaged over six amino acids through the length of P1; highest positive values represent charged hydrophilic regions.

In general, antigenic sites are usually hydrophilic. Therefore, where the amino acid sequence of a protein is known, hydrophilicity plots may be constructed which allow one to predict the location of antigenic determinants (Hopp and Woods, *Proc. Natl. Acad. Sci., U.S.A.*, 78:3824-3828 (1981)). Hydrophilicity plotting of the predicted *M. pneumonias* P1 sequence was performed using the Microgenie program obtained from Beckman (Palo Alto, Calif.). This analysis revealed potential antigenic sites (FIG. 7) at positions 240-260, 280-304, 314-333, 450-479, 680-690, 746-767, 898-913, 1244-1260, and 1476-1485.

EXAMPLE III

Expression of the Complete Recombinant P1 Protein

The following prophetic example is intended to describe methods by which the P1 gene could be expressed to provide a complete P1 protein.

The P1 protein could be expressed by ligating the piece of DNA that includes the first Hind III site through the second EcoRI site (see FIG. 5) to a mycoplasma compatible vector, such as *E.coli* plasmid pAM120, then transforming fast growing mycoplasma species (such as Acholeplasma) for production of large quantities of P1. (See Dybvig, K., et al., *Science*, 235:1392 (1987), which is incorporated herein by reference.)

The P1 gene could also be modified to express whole P1 in *E.coli*. All the UGA codons in the structural gene of P2 could be changed into UGG by site specific mutagenesis. See Shortle, D., et al., *Meth. in Enzymol.*, 100:457 (1983), which is incorporated herein by reference. Then a powerful *E.coli* promoter such as the lac promoter could be ligated to the P1 gene to overproduce P1. Alternatively, an *E.coli* strain with UGA suppressor phenotype (Raftery, L., et al., *J. Bacteriol.*, 158:849 (1984), which is incorporated herein by reference) could be used as host to express the unmodified P1 gene.

Also, the P1 gene promoter is a unique mycoplasma promoter which can be used for the expression of other proteins in mycoplasma species.

EXAMPLE IV

Cloning, Sequecing, and Expression of Nucleotide Sequences Encoding the Functional Cytadhesin Binding Domain of *M. pneumoniae*

This example describes the construction of the lambda gt11 recombinant DNA expression library of *M. pneumonias* used to characterize the P1 domain involved in cytadherence. In general, clones expressing P1 epitopes were identified by screening the library with two anti-P1 monoclonal antibodies known to block *M. pneumonias* attachment to erythrocytes (RBCS) and respiratory epithelium.

A. Construction of the Lambda gt11 Library

1. Bacteria, Vector, and Restriction Enzymes

*M. pneumonias* strain M129-B16 was cultured as described in Example I. *E.coli* Y1088 (American Type Culture Collection (ATCC#37195), Y1089 (ATCC#37196), and Y1090 (ATCC#37197) were cultured in LB medium. These cell lines are available through the American Type Culture Collection or from Clontech Laboratories (Palo Alto, Calif.).

Lambda gt11 DNA arms and phage extracts were purchased from Promega Biotech (Madison, Wis.). Enzymes used for constructing the genomic library were from New England Biolabs (Beverly, MS); restriction enzymes were from BRL (Gaitherburg, Md.).

2. Construction of the *M. pneumoniae* Genomic Library in Lambda gt11

*M. pneumonias* strain M129-B16 genomic DNA library was constructed in the expression vector lambda gt11 according to general procedures described by Young and Davis, *Proc. Natl. Acad. Sci.*, 80:1194–1198 (1983) and *Science*, 222:778–782 (1983) incorporated herein by reference.

More specifically, mycoplasmal DNA was extracted and fragmented as described in Example I, but using mechanical shearing in place of restriction endonucleases.

The sheared DNA was then ligated to EcoRI linkers, and these DNA fragments were ligated into the EcoRI site in lambda gt11 arms essentially as described by Young and Davis, *Proc. Natl. Acad. Sci.*, 80:1194 (1983) and *Science*, 22:778 (1983). Briefly, this procedure comprises incubating the vector DNA and the *M. pneumonias* DNA fragments at high vector/insert ratio of 2:1 in ligation buffer (0.066 M Tris-HCl, pH 7.5; 5 mM MgCl$_2$; 5 mM DTT; 1 mM ATP) with 1U T4 DNA ligase at 12° C. for 2–16 hours.

Recombinant DNA was packaged to provide viable phage according to instructions provided by the commercial supplier of the phage arms and phage extracts (Promega Biotech, Madison, Wis.). Alternatively, packaging extracts may be prepared and packaging reactions carried out according to protocols described on pages 256–268 of *MOLECULAR CLONING*.

The phage may then be titered by plating a small number of phage from the packaging mix (about 100) on *E. coli* Y1088 at 42° C., using 2.5 ml LB soft agar (pH 7.5) containing 40 ul of 40 mg/ml×gal and 40 ul of 1MPTG for a 90 mm Petri dish. Plaques produced by the parental lambda gt11 phage are blue, while plaques produced by the recombinant phage are colorless. (In a few cases, particular recombinant phage plaques will produce a slight amount of blue color.)

The library may then be amplified by plating out the library at a density of 10$^6$ p.f.u. per 150 mm Petri dish, using 600 ul of Y1088 plating cells per dish and fresh LB plates and incubating at 42° C. Plate stocks may be prepared as described by Davis, et al., *Bacterial Genetics*, Cold Spring Harbor Laboratory, Cold Spring Harbor, N.Y. (1980).

Alternatively, it is possible to screen the lambda gt11 library without amplification. For this procedure, 0.1 ml Y1088 plating cells are infected with $\leq$10 plaque forming units at 37° C. for 15 minutes. Then 0.5 ml of Y1090 plating cells and 7.5 ml LB soft agar are added. The mixture is poured into a two-day old 150 mm LB plate (pH 7.5).

B. Screening Lambda gt11 *M. pneumonias* DNA Libraries with Monoclonal Antibody Probes The *M. pneumonias* DNA phage library was screened with a pool of two anti-P1 monoclonal antibodies directed against unique *M. pneumonias* epitopes involved in cytadherence. The screening procedure was generally performed as follows.

*E. coli* Y1090 was grown to saturation in LB (pH 7.5) at 37° C. and 0.6 ml of the Y1090 culture was mixed with up to $10^5$ p.f.u. in lambda diluent for each plate. The phage were absorbed to the cells at 37° C. for 15 minutes. Then 7.5 ml of LB soft agar (pH 7.5) was added to the culture and the mixture was poured onto an LB plate (pH 7.5). The plates were incubated at 42° C. for 3–4 hours and then placed at 37° C. Each plate was then overlayed with a dry nitrocellulose filter disk which had been saturated in 10 mM IPTG in water. The plates were then incubated for an additional 2–3 hours at 37° C. and removed to room temperature. The filters were then removed from the plate and the following steps were performed.

First, the filters were rinsed briefly in TBS (50 mM Tris-HCl, pH 8.0, 150 mM NaCl) and incubated in TBS plus 20% fetal calf serum for 15–30 minutes. The filters were then incubated in TBS plus 20% fetal calf serum plus a mixture containing 1 ug/ml MAb6E7 and 2 ug/ml MAb5B8 for one hour. Preparation of these antibodies is described in Plummer, et al., *Infect. Immun.*, 53:398–403 (1986), incorporated herein by reference.

The filters were then washed in TBS for 5–10 minutes, washed again in TBS plus 0.1% NP-40 for 5–10 minutes, rewashed in TBS alone for 5–10 minutes, rinsed briefly in TBS plus 20% fetal calf serum, and transferred to TBS plus 20% fetal calf serum containing horseradish peroxidase-conjugated to goat anti-mouse immunoglobulin. The filters were then washed again in TBS, TBS plus 0.1% NP-40, and TBS. The filters were dried and 4-chloro-1-naphthol was used as substrate to develop the immunoblots.

When the lambda gt11 *M. pneumonias* genomic library was screened with the two monoclonal antibodies, ten independent clones that produced strong signals were isolated. Eight of the clones reacted with both monoclonal antibodies, one clone (P1-7) reacted only with MAb6E7 and another clone (P1-10) reacted only with MAb5B8. The nucleotides encompassed by each of these clones is indicated by FIG. 8.

C. Analysis of the Recombinant Phage Clones

The following experiments were performed in order to further characterize the mycoplasmal proteins produced by the recombinant phage. Positive signal-producing phage were grown in *E. coli* Y1090 as described in *MOLECULAR CLONING,* pp. 64–65. DNA was extracted by a rapid small-scale plate lysate method using 2 units of EcoRI to excise the *M. pneumonias* DNA inserts essentially as described in *MOLECULAR CLONING,* pp. 371–372.

1. Sequencing of the *M. pneumonias* DNA Inserts

DNA sequences of the recombinant phage inserts were determined essentially as described in Example II. The results of this analysis are shown in FIGS. 8 and 9A–9B. By comparing the sequences of these clones to the complete P1 gene sequence (FIGS. 6A–6N), the cytadhesin binding domain of the *M. pneumonias* P1 protein was mapped to the C-terminal region of the P1 gene. The sequences of three clones were of particular utility in further mapping antigenic epitopes of P1. These clones were P1–7, P1–9, and P-10. As shown in FIG. 9A, clone P1–7 starts at position 4067 and ends at position 4185; clone P1–9 starts at position 4148 and extends beyond the end of the P1 gene. These two clones both contain nucleotides 4148–4185. These nucleotides code for a P1 polypeptide thirteen amino acids in length, the thirteen amino acids that contain the epitope reactive with the cytadherence-blocking MAb6E7. Clone P1–10 starts at position 4202 and extends beyond the P1 gene. This clone is nonreactive with MAb6E7, yet shares a stretch of nucleotides that overlap with clone P1–9; further demarcating the thirteen amino acid cytadherence related epitope.

Therefore, a key domain of adhesin P1 that mediates the cytadherence of virulent *M. pneumonias* to respiratory epithelium has been mapped to a thirteen amino acid region located in the C-terminal end of the P1 molecule. In addition, the present studies have established that a second cytadhesin epitope, recognized by MAb5B8, is C-terminal to position 4202. Therefore, the C-terminal end of the P1 protein appears to be the primary effector region of the P1 molecule. It is interesting that the carboxy terminus of the P1 protein is proline rich (13 of the last 26 amino acids are proline). This hydrophobic domain may function to anchor the carboxy terminal end of the P1 molecule in the *M. pneumonias* membrane.

2. The Thirteen Amino Acid Cytadhesin Epitope is Unique to *M. pneumonias* P1

By comparing the sequence of the P1-7 probe to the known DNA sequence of the complete P1 gene, it was determined that thd P1 molecule contained only one copy of the thirteen amino acid epitope described above. However, it was of interest to determine whether or not this epitope was unique to *M. pneumonias*. Therefore, the following experiment was performed.

Mycoplasma DNA was digested with different restriction enzymes (BamHI, EcoRI, Hind III, Pst I, Sac I, Sma I) and fractionated by agarose gel electrophoresis, essentially as described in Example ID above. However, the DNA insert from clone P1-7 was used as a hybridization probe. Hybridization was carried out at 68° C. overnight according to Maniatis, et al., *MOLECULAR CLONING*, Cold Spring Harbor Laboratory, Cold Spring Harbor, N.Y. (1982), pp. 382-289. The results of this procedure, shown in FIG. 10, clearly demonstrate that the cytadherence related epitope of clone P1-7 occurs only once in the *M. pneumonias* genome.

D. Analysis of *M. pneumonias* P1 Cytadhesin Peptides

The following studies were undertaken to further characterize the cytadhesin polypeptides produced by the recombinant lambda gt11 bacteriophage.

It will be appreciated by those familiar with the lambda gt11 fusion system, that the site used for insertion of foreign DNA is a unique EcoRI cleavage site located within the lacZ gene, 53 base pairs upstream from the beta-galactosidase translation termination codon. Because the site of insertion for foreign DNA in lambda gt11 is within the structural gene for beta-galactosidase, foreign DNA sequences in this vector have the potential to be expressed as fusion proteins with beta-galactosidase. The position within the beta-galactosidase gene chosen for fusion with foreign DNA sequences, corresponds to a region near the carboxy terminus of the beta-galactosidase protein.

Fusion proteins expressed by the recombinant clones of the present invention were analyzed by Western blotting. This procedure was performed essentially as follows. *M. pneumonias* protein (2 mg) was suspended in 0.3 ml of PBS, and an equal volume of 100 mM Tris (pH 6.8) —2% S.D.S. —20% glycerol —2% 2-mercaptoethanol-0.02% bromophenol blue buffer (SP buffer) was added. Samples were boiled for 5 minutes. Recombinant fusion proteins were harvested from plate lysates of individual clones by scraping soft agarose overlays from the plates, passing them through a 22 gauge needle into a Corex tube and eluding with 4 m of SM buffer for two hours at 4° C. The agarose was pelleted by centrifugation at 10,000×g for 15 minutes at 4° C. prior to trichloracetic acid precipitation of the supernatant by the addition of cold trichloracetic acid, for a final concentration of 10%. Samples were incubated at 4° C. overnight prior to centrifugation at 10,000×g for 20 minutes at 4° C. Supernatants were discarded, and pellets were washed twice with 1 ml of PBS, suspended in 200 ul of SP buffer, and neutralized with 1 ul of 5N NAOH. Samples were boiled for 5 minutes and solubilized proteins were electrophoresed on a 5.0% polyacrylamide gel prior to electrophoretic transfer to nitrocellulose paper (Towbin, et al., *Proc. Natl. Acad. Sci., U.S.A.*, 76:4350–4354 (1979)).

After protein transfer, the nitrocellulose was cut into strips and reacted with a pool of the two MAbs (monoclonal antibodies) designated 5B8 and 6E7. For this procedure, nitrocellulose blots were blocked in 1.5% bovine serum albumin (BSA) — 1.5% gelatin in TBS for 3-4 hours prior to incubation with the pooled monoclonal antibodies. The final concentration of the antibodies in the reaction mixture was 2 ug/ml 5B8 and 1 ug/ml 6E7 in a buffer comprising TBS plus 20% FCS. Blots were incubated with the diluted antibody preparation overnight at room temperature with shaking, following by three ten minute washes with TBS. Horseradish peroxidase-conjugated goat anti-mouse IgG diluted 1:2000 in TBS containing 0.75% BSA 0.75% gelatin was added to the blots and incubated with shaking for 3-4 hours at room temperature. Blots were washed three times for ten minute periods with TBS prior to substrate development.

The results of this procedure, shown in FIG. 11, show the representative clones produced fusion proteins larger than the control lambda gt11 beta-galactosidase protein. However, except for clone P1-7, the size of each fusion protein was much smaller than that predicted from the size of the corresponding recombinant DNA insert. This finding may be explained as resulting from early termination of the cytadhesin peptide due to the presence of the TGA codon at position 4556. The present inventors have discovered that *M. pneumonias* utilizes this codon for tryptophan, while *E. coli* reads UGA as stop signal. Therefore, when *E. coli* is used as a host for a vector containing the recombinant Pneumonias insert, a prematurely truncated polypeptide may be produced.

E. Cytadhesin Peptides Can Be Used for Serodiagnosis of *M. pneumonias* Infection Studies have shown that adhesin P1 is highly immunogenic (Hu, et al., Science, 216:313-315 (1982)) and patients infected with *M. pneumonias* exhibit neutralizing antibodies to the P1 adhesin (Leith, et al., *J. Exp. Med.*, 157:502-516 (1983)). Since the isolated clones express P1 cytadhesin peptides, these clones were analyzed for reactivity with sera of patients with early and late stages of *M. pneumonias* infection. Normal human sera was used as a control. These experiments were performed by the immunophage blot method. Briefly, this procedure was performed as follows. Individual recombinant phages were dotted on a lawn of *E. coli* Y1090. The plates were incubated at 42° C. for 3-5 hours. Then a nitrocellulose filter (HAHY, M) previously saturated with 10 mM IPTG was overlayed on individual plates and incubation continued at 37° C. overnight. Filters were removed and reacted with sera from *M. neumoniae* infected patients or normal human controls essentially as described in FIGS. 12-I, 12-II, 12-III using horseradish peroxidase-conjugated goat anti-human immunogloblin, and 4-chloro-1-naphthol to develop the immunoblots.

The results of this procedure, shown in FIG. 12, indicated that fusion proteins produced by all ten anti-P1 MAb reactive clones also reacted with acute and convalescent sera of *M. pneumonias* infected patients but did not react with normal human serum. Therefore, the cytadherence related P1 peptides or fusion proteins described herein may be used for serodiagnosis of patients infected with *M. pneumonias*.

F. Preparation of Recombinant Antigens from the Lambda gt11 Recombinant Clones

It is often useful to have preparative amounts of polypeptides specified by a cloned piece of DNA. For some purposes, for instance, radioimmunoassays, it is sufficient to have a crude *E. coli* lysate containing an antigen specified by the cloned DNA of interest. This prophetic example illustrates how a crude lysate containing a cytadhesin peptide fusion protein can be prepared by expressing a lambda gt11 recombinant as a lysogen in *E. coli* 1089 (*E. coli* Delta lac U169 proA+Delta lon ara D139 strA hsl A150 (chr::Tn10] (p MC9)). The recombinant fusion protein would be produced by lysogenizing Y1089 with the lambda gt11 clone of interest. The lysogen would be grown to high cell density, lacZ-directed fusion protein production induced by the addition of IPTG to the medium, and the cells harvested and lysed.

More specifically, the Y1089 cells would be grown to saturation in LB medium (pH 7.5/0.2% maltose) at 37° C. and then infected with the selected lambda gt11 recombinant phage (preferably P1-7) at a multiplicity of approximately 5 for 20 minutes at 32° C. in LB medium (pH 7.5) supplemented with 10 mm MgCl$_2$. The cells would then be plated on LB plate at a density of approximately 200/plate and incubated at 32° C. At this temperature, the temperature sensitive phage repressor is functional. Single colonies would be tested for temperature sensitivity at 42° C. by spotting cells from single colonies using sterile toothpicks onto two LB plates. The first plate would be incubated at 42° C. and the second at 32° C. Clones growing at 32° C. but not at 42° C. are assumed to be lysogens. Lysogens should arise at a frequency between 10% and 70%.

The crude lysate would then be prepared from the lambda gill recombinant lysogen by incubating 100 ml of LB medium with a single colony of the Y1089 recombinant lysogen at 32° C. with aeration. When the culture has grown to an optical density of 0.5 measured at 600 mm, the temperature of the culture would be increased to 42°-54° C. as rapidly as possible and the culture incubated at the elevated temperature for 20 minutes with good aeration. IPTG would be added to 10 mM and the culture is incubated at 37°-38° C. for approximately one hour. At this stage, the Y1089 lysogen will sometimes lyse, even though the Y1089 does not suppress the mutation, causing defective lyses (S100) in lambda gt11. The reason for this is that the S100 amber mutation is leaky and foreign proteins accumulating in *E. coli* often render it susceptible to lysis. Therefore, the longest incubation time achievable at 37°-38° C. without lysis occurring should be determined for each individual recombinant lysogen. After incubation, the cells would be harvested in a Beckman J. A.-ten rotor at 5,000 r.p.m. for 5 minutes 27°-37° C. The cells would then be rapidly resuspended in 1/20 to 1/50 of the original culture volume in a buffer suitable for protein and the resuspended cells are rapidly frozen in liquid nitrogen. When the frozen cells are thawed, essentially complete lysis of the induced lysogen results.

If crude antigen is required, the crude lysate described above could be used. However, if pure antigen is needed, the beta-galactosidase fusion protein would be purified by any of a number of methods known to those of skill in the art. The most rapid method of purification takes advantage of the size of the beta-galactosidase fusion protein (approximately 114 kDa). Since only a few proteins in *E. coli* are larger than beta-galactosidase, the fusion protein is often resolved from other proteins on SDS-polyacrylamide gels. Preparative gels could be used to isolate large quantities of denatured protein. If pure antigen in native form is required, then the fusion protein could be prepared by classical column chromatography.

G. Synthesis of a Synthetic Peptide Containing the Amino Acid Cytadhesin Epitopes The following prophetic example describes methods for preparing synthetic polypeptides containing cytadhesin epitopes. *M. pneumonias* P1 polypeptides could be prepared by any of a number of methods known to those of skill in the art. These methods include but are not limited to solid and liquid phase chemical synthesis and biological in vitro synthesis. For example, see Marglin and Merrifield, *Annu. Red. Biochem.*, 39:841–866 (1970); Merrifield, et al., *Biochemistry*, 21:5020–5031 (1982); Pelham and Jackson, *Eru. J. Biochem.*, 67:247–256 (1976); and Shinnick, et al., *Ann. Rev. Microbiol.*, 37:425–446 (1983), all incorporated herein by reference. Of course, where an MRNA translation system is used, e.g., reticulocyte lysate system, it is important to prepare mRNA from the DNA clones of the present invention. Techniques for preparing the MRNA from DNA clones are known in the art. For example, see those described in Chapter 2, 1987 Promega Biological Research Products Catalogue, obtainable from Promega Biolabs, 2800 South Fish Hatchery Road, Madison, Wis. 53711-5305 and incorporated herein by reference. A preferred method for preparing a synthetic peptide may be found in U.S. Pat. No. 4,493,795 issued to Nestor, Jr., et al., and incorporated herein by reference. A second method is found in U.S. Pat. No. 4,474,757, issued to Arman, et al., and also incorporated herein by reference.

H. Preparation of *M. pneumonias* Compositions For Use As *M. pneumonias* Vaccines Of course, it is also likely that the cytadhesin peptides may be effectively used as vaccines to prevent atypical pneumonias caused by *M. pneumonias*. The preparation of vaccines which contain peptide sequences as active ingredients is generally well understood in the art, as exemplified by U.S. Pat. Nos. 4,474,757; 4,493,795; 4,608,251; 4,601,903; 4,599,231; 4,599,230; 4,596,792; and 4,578,770, all incorporated herein by reference.

This prophetic example describes preparation and administration of such vaccines. In general, immunogenic compositions suitable for administration as vaccines could be formulated to include one or more of the antigenic epitopes produced by the recombinant cells of the present invention or synthetically prepared. The antigens could be included in optimal amounts, for example, approximately equimolar or equi-antigenic amounts. Typically, such vaccines are prepared as injectables: either as liquid solutions or suspensions, solid forms suitable for solution in, or suspension in, liquid prior to injection may also be prepared. The preparation could also be emulsified. The reactive immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine could contain minor amounts of auxiliary substances such as wetting or emulsifying agents, pH buffering agents, or adjuvants which enhance the effectiveness of the vaccine.

In addition, immunogenicity of cytadhesin peptides could be increased by conjugation of a carrier molecule, for example, dipalmityl lysine. (See Hopp, *Mol. Immunol.*, 21:13–16 (1984) incorporated herein by reference.)

The proteins or polypeptides could be formulated into the vaccine as neutral or salt forms and administered in a manner compatible with the dosage formulation, and in such amount as will be therapeutically effective and immunogenic. The vaccines could be conventionally administered parenterally, by injection, for example, either subcutaneously or intramuscularly. Additional formulations which are suitable for other modes of administration might include oral or intranasal formulations. The quantity to be administered will depend on the subject to be treated, capacity of the immune system to synthesize antibodies, and the degree of protection desired. Precise amounts of active ingredient required to be administered will depend on the judgment of the practitioner and may be peculiar to each individual. However, suitable dosage ranges will be on the order of 1 to 100 ug active ingredient per individual. Suitable regimes for initial administration and booster shots will also be variable, but may be typified by an initial administration followed by subsequent inoculations or other administrations.

In many instances, it may be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1–5 years, usually three years, will be desirable to maintain protective levels of the antibodies. The course of the immunization may be followed by assays for antibodies for the antigens as described below.

I. Immunoassay For *M. pneumonias* Antibodies

As demonstrated by Example IV E., certain of the P1 polypeptides are known to react with antisera from patients infected with *M. pneumonias.* Accordingly, these polypeptides may be used as antigens in immunoassay procedures. These assays are well known to those of skill in the art. For examples of such assays, see Nisonoff, *Introduction to Molecular Immunology,* 2nd Ed., Sinaues Associates, Inc., Sunderland, Mass. (1984) and U.S. Pat. No. 4,376,110, both incorporated herein by reference.

The following prophetic example is designed to illustrate such procedures. Generally, for detection of antibody in aqueous samples, the antigen, or antigen composition, is preferably adsorbed, or otherwise attached, to an appropriate adsorption matrix, for example, the inside surface of a microtiter dish well, and an aqueous suspected antibody-containing composition contacted therewith to cause immunocomplex formation. The matrix is then washed to remove non-specifically bound material and the amount of material which is specifically immunocomplexed thereto determined, typically through the use of an appropriate labeled ligand.

The cytadhesin polypeptides provided by the present invention may also be incorporated into a diagnostic kit. Such kits are widely used in clinical settings because they often offer greater convenience and simplicity than other assays. A number of kits might be utilized in the practice of the present invention, for example, a kit comprising a carrier compartmentalized to receive at least one, at least two, or at least three or more containers and to maintain said containers enclosed confinement.

A first container might include one or more of the *M. pneumonias* antigens, or antigen-containing compositions. Alternatively, or in addition, the kits will include antibody compositions having specificity for one or more of the antigens. Both antibody and antigen preparations should preferably be provided in a suitable titrated form, with antigen concentrations and/or antibody titers given for easy reference in quantitative applications.

The kits will also typically include an immunodetection reagent or label for the detection of specific immunoreaction between the provided antigen and/or antibody, as the case may be, and the diagnostic sample. Suitable detection reagents are well known in the art as exemplified by radioactive, enzymatic or otherwise chromogenic ligands, which are typically employed in association with the antigen and/or antibody, or in association with a second antibody having specificity for the antigen or first antibody. Thus, the reaction is detected or quantified by means of detecting or quantifying the label. Immunodetection reagents and processes suitable for application in connection with the novel compositions of the present invention are generally well known in the art.

The foregoing description has been directed to particular embodiments of the invention in accordance with the requirements of the Patent Statutes for the purposes of illustration and explanation. It will be apparent, however, to those skilled in this art, that many modifications and changes in the apparatus and procedure set forth will be possible without departing from the scope and spirit of the invention. It is intended that the following claims be interpreted to embrace all such modifications and changes.

SEQUENCE LISTING ( 1 ) GENERAL INFORMATION:

( i i i ) NUMBER OF SEQUENCES: 10

( 2 ) INFORMATION FOR SEQ ID NO:1:

```
        ( i ) SEQUENCE CHARACTERISTICS:
                ( A ) LENGTH: 13 Amino Acids
                ( B ) TYPE: Amino Acid
                ( C ) STRANDEDNESS: Single
                ( D ) TOPOLOGY: Linear ( i i ) MOLECULE TYPE: Genomic DNA
                ( A ) DESCRIPTION: Deduced amino acid sequence of
                        polypeptide fragment no. 1

( i i i ) HYPOTHETICAL: No ( v ) FRAGMENT TYPE: internal fragment ( v i ) ORIGINAL SOURCE:
                ( A ) ORGANISM: Mycoplasma pneumoniae
                ( B ) STRAIN: M129-B16

( v i i ) IMMEDIATE SOURCE:
                ( B ) CLONE: Gene cloned in lambda gt11 phage in E.
                        coli Y1090

( i x ) FEATURE:
                ( A ) NAME/KEY: Deduced amino acid sequence of
                        polypeptide fragment no. 1
                ( B ) LOCATION: Amino Acids: 1383 to 1395
                ( D ) OTHER INFORMATION: Phenotype Conferred:
                        cytadhering and virulent; Biological Activity:
                        cytadherence; Functional Class: cytadhesin;
                        Binding Macromolecules: receptors unknown;
                        Subcellular Location: membrane ( x i ) SEQUENCE DESCRIPTION: SEQ ID NO:1:

Gly Ile Val Arg Thr Pro Leu Ala Glu Leu Leu Asp Gly
1               5                   10
```

( 2 ) INFORMATION FOR SEQ ID NO:2:

```
        ( i ) SEQUENCE CHARACTERISTICS:
                ( A ) LENGTH: 39 Nucleotides
                ( B ) TYPE: Nucleic Acid
                ( C ) STRANDEDNESS: Single
                ( D ) TOPOLOGY: Linear ( i i ) MOLECULE TYPE: Genomic DNA
                ( A ) DESCRIPTION: Nucleic acid sequence of polypeptide
                        fragment no. 1

( i i i ) HYPOTHETICAL: No ( v ) FRAGMENT TYPE: internal fragment ( v i ) ORIGINAL SOURCE:
                ( A ) ORGANISM: Mycoplasma pneumoniae
                ( B ) STRAIN: M129-B16

( v i i ) IMMEDIATE SOURCE:
                ( B ) CLONE: Gene cloned in lambda gt11 phage in E. coli
                        Y1090

( i x ) FEATURE:
                ( A ) NAME/KEY: Nucleic acid sequence of polypeptide fragemnt
                        no. 1
                ( B ) LOCATION: Nucleotide Numbers: 4147 to 4185
                ( D ) OTHER INFORMATION: Phenotype Conferred: cytadhering and
                        virulent; Biological Activity: cytadherence; Functional
                        Class: cytadhesin; Binding Macromolecules: receptors
                        unknown; Subcellular Location: membrane ( x i ) SEQUENCE DESCRIPTION: SEQ ID NO:2:

GGT ATT GTA CGC ACC CCA CTC GCT GAA CTG TTA GAT GGG    4185
Gly Ile Val Arg Thr Pro Leu Ala Glu Leu Leu Asp Gly
1               5                   10
```

( 2 ) INFORMATION FOR SEQ ID NO:3:

```
        ( i ) SEQUENCE CHARACTERISTICS:
                ( A ) LENGTH: 40 Amino Acids
```

(B) TYPE: Amino Acid
(D) TOPOLOGY: Linear (i i) MOLECULE TYPE: Genomic DNA
    (A) DESCRIPTION: Deduced amino acid sequence of
        polypeptide fragment no. 2

(i i i) HYPOTHETICAL: No (v) FRAGMENT TYPE: internal fragment (v i) ORIGINAL SOURCE:
    (A) ORGANISM: Mycoplasma pneumoniae
    (B) STRAIN: M129-B16

(v i i) IMMEDIATE SOURCE:
    (B) CLONE: Gene cloned in lambda gt11 phage in E. coli
        Y1090

(i x) FEATURE:
    (A) NAME/KEY: Deduced amino acid sequence of polypeptide
        fragment no. 2
    (B) LOCATION: Amino Acid Numbers: 1356 to 1395

(x i) SEQUENCE DESCRIPTION: SEQ ID NO:3:

```
Asn Thr Asn Thr Gly Asn Asp Val Val Gly Val Gly Arg Leu Ser Glu
1               5                   10                  15
Ser Asn Ala Ala Lys Met Asn Asp Asp Val Asp Gly Ile Val Arg Thr
20                  25                  30
Pro Leu Ala Glu Leu Leu Asp Gly
35                  40
```

(2) INFORMATION FOR SEQ ID NO:4:

(i) SEQUENCE CHARACTERISTICS:
    (A) LENGTH: 120 Nucleotides
    (B) TYPE: Nucleic Acid
    (C) STRANDEDNESS: Single
    (D) TOPOLOGY: Linear (i i) MOLECULE TYPE: Genomic DNA
    (A) DESCRIPTION: Nucleic acid sequence for polypeptide
        fragment no. 2

(i i i) HYPOTHETICAL: No (v) FRAGMENT TYPE: internal fragment (v i) ORIGINAL SOURCE:
    (A) ORGANISM: Mycoplasma pneumoniae
    (B) STRAIN: M129-B16

(v i i) IMMEDIATE SOURCE:
    (B) CLONE: Gene cloned in lambda gt11 phage in E. coli
        Y1090

(i x) FEATURE:
    (A) NAME/KEY: Nucleic acid sequence of polypeptide fragment
        no. 2
    (B) LOCATION: Nucleotide Numbers: 4066 to 4185

(i x) SEQUENCE DESCRIPTION: SEQ ID NO:4:

```
AAT ACT AAT ACG GGG AAT GAT GTG GTG GGG GTT GGT CGA CTT TCT GAA   4113
Asn Thr Asn Thr Gly Asn Asp Val Val Gly Val Gly Arg Leu Ser Glu
1               5                   10                  15
AGC AAC GCC GCA AAG ATG AAT GAC GAT GTT GAT GGT ATT GTA CGC ACC   4161
Ser Asn Ala Ala Lys Met Asn Asp Asp Val Asp Gly Ile Val Arg Thr
20                  25                  30
CCA CTC GCT GAA CTG TTA GAT GGG    4185
Pro Leu Ala Glu Leu Leu Asp Gly
35                  40
```

(2) INFORMATION FOR SEQ ID NO:5:

(i) SEQUENCE CHARACTERISTICS:
    (A) LENGTH: 136 Amino Acids
    (B) TYPE: Amino Acid
    (D) TOPOLOGY: Linear (ii) MOLECULE TYPE: Genomic DNA
    (A) DESCRIPTION: Deduced amino acid sequence of
        polypeptide fragment no. 3

(iii) HYPOTHETICAL: No (v) FRAGMENT TYPE: internal fragment (vi) ORIGINAL SOURCE:
    (A) ORGANISM: Mycoplasma pneumoniae
    (B) STRAIN: M129-B16

(vii) IMMEDIATE SOURCE:
    (B) CLONE: Gene cloned in lambda gt11 phage in E. coli
        Y1090

(ix) FEATURE:
    (A) NAME/KEY: Deduced amino acid sequence of polypeptide
        fragment no. 3
    (B) LOCATION: Amino Acid Numbers: 1383 to 1518

(xi) SEQUENCE DESCRIPTION: SEQ ID NO:5:

| | | | | | | | | | | | | | | | |
|---|---|---|---|---|---|---|---|---|---|---|---|---|---|---|---|
| Gly | Ile | Val | Arg | Thr | Pro | Leu | Ala | Glu | Leu | Leu | Asp | Gly | Glu | Gly | Gln |
| 1 | | | | 5 | | | | | 10 | | | | | 15 | |
| Thr | Ala | Asp | Thr | Gly | Pro | Gln | Ser | Val | Lys | Phe | Lys | Ser | Pro | Asp | Gln |
| 20 | | | | | 25 | | | | 30 | | | | | | |
| Ile | Asp | Phe | Asn | Arg | Leu | Phe | Thr | His | Pro | Val | Thr | Asp | Leu | Phe | Asp |
| 35 | | | | | 40 | | | | 45 | | | | | | |
| Pro | Val | Thr | Met | Leu | Val | Tyr | Asp | Gln | Tyr | Ile | Pro | Leu | Phe | Ile | Asp |
| 50 | | | | | 55 | | | | 60 | | | | | | |
| Ile | Pro | Ala | Ser | Val | Asn | Pro | Lys | Met | Val | Arg | Leu | Lys | Val | Leu | Ser |
| 65 | | | | | 70 | | | | 75 | | | | | | 80 |
| Phe | Asp | Thr | Asn | Glu | Gln | Ser | Leu | Gly | Leu | Arg | Leu | Glu | Phe | Phe | Lys |
| 85 | | | | | 90 | | | | 95 | | | | | | |
| Pro | Asp | Gln | Asp | Thr | Gln | Pro | Asn | Asn | Asn | Val | Gln | Val | Asn | Pro | Asn |
| 100 | | | | | 105 | | | | 110 | | | | | | |
| Asn | Gly | Asp | Phe | Leu | Pro | Leu | Leu | Thr | Ala | Ser | Ser | Gln | Gly | Pro | Gln |
| 115 | | | | | 120 | | | | 125 | | | | | | |
| Thr | Leu | Phe | Ser | Pro | Phe | Asn | Gln | | | | | | | | |
| 130 | | | | | 135 | | | | | | | | | | |

(2) INFORMATION FOR SEQ ID NO:6:

(i) SEQUENCE CHARACTERISTICS:
    (A) LENGTH: 408 Nucleotides
    (B) TYPE: Nucleic Acid
    (C) STRANDEDNESS: Single
    (D) TOPOLOGY: Linear (ii) MOLECULE TYPE: Genomic DNA
    (A) DESCRIPTION: Nucleic acid sequence of polypeptide
        fragment no. 3

(iii) HYPOTHETICAL: No (v) FRAGMENT TYPE: internal fragment (vi) ORIGINAL SOURCE:
    (A) ORGANISM: Mycoplasma pneumoniae
    (B) STRAIN: M129-B16

(vii) IMMEDIATE SOURCE:
    (B) CLONE: Gene cloned in lambda gt11 phage in E. coli
        Y1090

(ix) FEATURE:
    (A) NAME/KEY: Nucleic acid sequence of polypeptide fragment

-continued no. 3
( B ) LOCATION: Nucleotide Numbers: 4147 to 4554

( x i ) SEQUENCE DESCRIPTION: SEQ ID NO:6:

```
GGT ATT GTA CGC ACC CCA CTC GCT GAA CTG TTA GAT GGG GAA GGA CAA    4194
Gly Ile Val Arg Thr Pro Leu Ala Glu Leu Leu Asp Gly Glu Gly Gln
1               5                   10                  15

ACA GCT GAC ACT GGT CCA CAA AGC GTG AAG TTC AAG TCT CCT GAC CAA    4242
Thr Ala Asp Thr Gly Pro Gln Ser Val Lys Phe Lys Ser Pro Asp Gln
20              25                  30

ATT GAC TTC AAC CGC TTG TTT ACC CAC CCA GTC ACC GAT CTG TTT GAT    4290
Ile Asp Phe Asn Arg Leu Phe Thr His Pro Val Thr Asp Leu Phe Asp
35              40                  45

CCG GTA ACT ATG TTG GTG TAT GAC CAG TAC ATA CCG CTG TTT ATT GAT    4338
Pro Val Thr Met Leu Val Tyr Asp Gln Tyr Ile Pro Leu Phe Ile Asp
50              55                  60

ATC CCA GCA AGT GTG AAC CCT AAA ATG GTT CGT TTA AAG GTC TTG AGC    4386
Ile Pro Ala Ser Val Asn Pro Lys Met Val Arg Leu Lys Val Leu Ser
65              70                  75                  80

TTT GAC ACC AAC GAA CAG AGC TTA GGT CTC CGC TTA GAG TTC TTT AAA    4434
Phe Asp Thr Asn Glu Gln Ser Leu Gly Leu Arg Leu Glu Phe Phe Lys
85              90                  95

CCT GAT CAA GAT ACC CAA CCA AAC AAC AAC GTT CAG GTC AAT CCG AAT    4482
Pro Asp Gln Asp Thr Gln Pro Asn Asn Asn Val Gln Val Asn Pro Asn
100             105                 110

AAC GGT GAC TTC TTA CCA CTG TTA ACG GCC TCC AGT CAA GGT CCC CAA    4530
Asn Gly Asp Phe Leu Pro Leu Leu Thr Ala Ser Ser Gln Gly Pro Gln
115             120                 125

ACC TTG TTT AGT CCG TTT AAC CAG    4554
Thr Leu Phe Ser Pro Phe Asn Gln
130             135
```

( 2 ) INFORMATION FOR SEQ ID NO:7:

( i ) SEQUENCE CHARACTERISTICS:
      ( A ) LENGTH: 118 Amino Acids
      ( B ) TYPE: Amino Acid
      ( D ) TOPOLOGY: Linear ( i i ) MOLECULE TYPE: Genomic DNA
      ( A ) DESCRIPTION: Deduced amino acid sequence of
             polypeptide fragment no. 4

( i i i ) HYPOTHETICAL: No ( v ) FRAGMENT TYPE: internal fragment ( v i ) ORIGINAL SOURCE:
      ( A ) ORGANISM: Mycoplasma pneumoniae
      ( B ) STRAIN: M129-B16

( v i i ) IMMEDIATE SOURCE:
      ( B ) CLONE: Gene cloned in lambda gt11 phage in E. coli
             Y1090

( i x ) FEATURE:
      ( A ) NAME/KEY: Deduced amino acid sequence of polypeptide
             fragment no. 4
      ( B ) LOCATION: Amino Acid Numbers: 1401 to 1518

( x i ) SEQUENCE DESCRIPTION: SEQ ID NO:7:

```
Asp Thr Gly Pro Gln Ser Val Lys Phe Lys Ser Pro Asp Gln Ile Asp
1               5                   10                  15

Phe Asn Arg Leu Phe Thr His Pro Val Thr Asp Leu Phe Asp Pro Val
20              25                  30

Thr Met Leu Val Tyr Asp Gln Tyr Ile Pro Leu Phe Ile Asp Ile Pro
35              40                  45

Ala Ser Val Asn Pro Lys Met Val Arg Leu Lys Val Leu Ser Phe Asp
50              55                  60
```

```
Thr  Asn  Glu  Gln  Ser  Leu  Gly  Leu  Arg  Leu  Glu  Phe  Phe  Lys  Pro  Asp
65                       70                  75                           80

Gln  Asp  Thr  Gln  Pro  Asn  Asn  Asn  Val  Gln  Val  Asn  Pro  Asn  Asn  Gly
85                       90                  95

Asp  Phe  Leu  Pro  Leu  Leu  Thr  Ala  Ser  Ser  Gln  Gly  Pro  Gln  Thr  Leu
100                      105                 110

Phe  Ser  Pro  Phe  Asn  Gln
115
```

( 2 ) INFORMATION FOR SEQ ID NO:8:

( i ) SEQUENCE CHARACTERISTICS:
        ( A ) LENGTH: 354 Nucleotides
        ( B ) TYPE: Nucleic Acid
        ( C ) STRANDEDNESS: Single
        ( D ) TOPOLOGY: Linear ( i i ) MOLECULE TYPE: Genomic DNA
        ( A ) DESCRIPTION: Nucleic acid sequence of polypeptide
            fragment no. 4

( i i i ) HYPOTHETICAL: No ( v ) FRAGMENT TYPE: internal fragment ( v i ) ORIGINAL SOURCE:
        ( A ) ORGANISM: Mycoplasma pneumoniae
        ( B ) STRAIN: M129-B16

( v i i ) IMMEDIATE SOURCE:
        ( B ) CLONE: Gene cloned in lambda gt11 phage in E. coli
            Y1090

( i x ) FEATURE:
        ( A ) NAME/KEY: Nucleic acid sequence of polypeptide fragment
            no. 4
        ( B ) LOCATION: Nucleotide Numbers: 4201 to 4554

( x i ) SEQUENCE DESCRIPTION: SEQ ID NO:8:

```
GAC  ACT  GGT  CCA  CAA  AGC  GTG  AAG  TTC  AAG  TCT  CCT  GAC  CAA  ATT  GAC   4248
Asp  Thr  Gly  Pro  Gln  Ser  Val  Lys  Phe  Lys  Ser  Pro  Asp  Gln  Ile  Asp
1                        5                   10                          15

TTC  AAC  CGC  TTG  TTT  ACC  CAC  CCA  GTC  ACC  GAT  CTG  TTT  GAT  CCG  GTA   4296
Phe  Asn  Arg  Leu  Phe  Thr  His  Pro  Val  Thr  Asp  Leu  Phe  Asp  Pro  Val
20                       25                  30

ACT  ATG  TTG  GTG  TAT  GAC  CAG  TAC  ATA  CCG  CTG  TTT  ATT  GAT  ATC  CCA   4334
Thr  Met  Leu  Val  Tyr  Asp  Gln  Tyr  Ile  Pro  Leu  Phe  Ile  Asp  Ile  Pro
35                       40                  45

GCA  AGT  GTG  AAC  CCT  AAA  ATG  GTT  CGT  TTA  AAG  GTC  TTG  AGC  TTT  GAC   4392
Ala  Ser  Val  Asn  Pro  Lys  Met  Val  Arg  Leu  Lys  Val  Leu  Ser  Phe  Asp
50                       55                  60

ACC  AAC  GAA  CAG  AGC  TTA  GGT  CTC  CGC  TTA  GAG  TTC  TTT  AAA  CCT  GAT   4440
Thr  Asn  Glu  Gln  Ser  Leu  Gly  Leu  Arg  Leu  Glu  Phe  Phe  Lys  Pro  Asp
65                       70                  75                          80

CAA  GAT  ACC  CAA  CCA  AAC  AAC  AAC  GTT  CAG  GTC  AAT  CCG  AAT  AAC  GGT   4488
Gln  Asp  Thr  Gln  Pro  Asn  Asn  Asn  Val  Gln  Val  Asn  Pro  Asn  Asn  Gly
85                       90                  95

GAC  TTC  TTA  CCA  CTG  TTA  ACG  GCC  TCC  AGT  CAA  GGT  CCC  CAA  ACC  TTG   4536
Asp  Phe  Leu  Pro  Leu  Leu  Thr  Ala  Ser  Ser  Gln  Gly  Pro  Gln  Thr  Leu
100                      105                 110

TTT  ACT  CCG  TTT  AAC  CAG   4554
Phe  Ser  Pro  Phe  Asn  Gln
115
```

( 2 ) INFORMATION FOR SEQ ID NO:9:

( i ) SEQUENCE CHARACTERISTICS:
        ( A ) LENGTH: 1627 Amino Acids ( B ) TYPE: Amino Acid
( D ) TOPOLOGY: Linear ( i i ) MOLECULE TYPE: Genomic DNA
  ( A ) DESCRIPTION: Deduced amino acid sequence of P1 protein ( i i i ) HYPOTHETICAL: No ( v i ) ORIGINAL SOURCE:
  ( A ) ORGANISM: Mycoplasma pneumoniae
  ( B ) STRAIN: M129-B16

( v i i ) IMMEDIATE SOURCE:
  ( B ) CLONE: Gene cloned in pUC19 in E. coli HB101, ATCC Accession Number 67560

( i x ) FEATURE:
  ( A ) NAME/KEY: Amino acid sequence of P1 protein
  ( B ) LOCATION: Amino Acid Numbers: 1 to 1627

( x i ) SEQUENCE DESCRIPTION: SEQ ID NO:9:

```
Met His Gln Thr Lys Lys Thr Ala Leu Ser Lys Ser Thr Trp Ile Leu
 1           5                  10                  15
Ile Leu Thr Ala Thr Ala Ser Leu Ala Thr Gly Leu Thr Val Val Gly
20              25                  30
His Phe Thr Ser Thr Thr Thr Thr Leu Lys Arg Gln Gln Phe Ser Tyr
35              40                  45
Thr Arg Pro Asp Glu Val Ala Leu Arg His Thr Asn Ala Ile Asn Pro
50              55                  60
Arg Leu Thr Pro Trp Thr Tyr Arg Asn Thr Ser Phe Ser Ser Leu Pro
65              70                  75                  80
Leu Thr Gly Glu Asn Pro Gly Ala Trp Ala Leu Val Arg Asp Asn Ser
85              90                  95
Ala Lys Gly Ile Thr Ala Gly Ser Gly Ser Gln Gln Thr Thr Tyr Asp
100             105                 110
Pro Thr Arg Thr Glu Ala Ala Leu Thr Ala Ser Thr Thr Phe Ala Leu
115             120                 125
Arg Arg Tyr Asp Leu Ala Gly Arg Ala Leu Tyr Asp Leu Asp Phe Ser
130             135                 140
Lys Leu Asn Pro Gln Thr Pro Thr Arg Asp Gln Thr Gly Gln Ile Thr
145             150                 155                 160
Phe Asn Pro Phe Gly Gly Phe Gly Leu Ser Gly Ala Ala Pro Gln Gln
165             170                 175
Trp Asn Glu Val Lys Asn Lys Val Pro Val Glu Val Ala Gln Asp Pro
180             185                 190
Ser Asn Pro Tyr Arg Phe Ala Val Leu Leu Val Pro Arg Ser Val Val
195             200                 205
Tyr Tyr Glu Gln Leu Gln Arg Gly Leu Gly Leu Pro Gln Gln Arg Thr
210             215                 220
Glu Ser Gly Gln Asn Thr Ser Thr Thr Gly Ala Met Phe Gly Leu Lys
225             230                 235                 240
Val Lys Asn Ala Glu Ala Asp Thr Ala Lys Ser Asn Glu Lys Leu Gln
245             250                 255
Gly Ala Glu Ala Thr Gly Ser Ser Thr Thr Ser Gly Ser Gly Gln Ser
260             265                 270
Thr Gln Arg Gly Gly Ser Ser Gly Asp Thr Lys Val Lys Ala Leu Lys
275             280                 285
Ile Glu Val Lys Lys Lys Ser Asp Ser Glu Asp Asn Gly Gln Leu Gln
290             295                 300
Leu Glu Lys Asn Asp Leu Ala Asn Ala Pro Ile Lys Arg Ser Glu Glu
305             310                 315                 320
```

-continued

| | | | | | | | | | | | | | | |
|---|---|---|---|---|---|---|---|---|---|---|---|---|---|---|
| Ser 325 | Gly | Gln | Ser | Val | Gln 330 | Leu | Lys | Ala | Asp | Asp 335 | Phe | Gly | Thr | Ala | Leu |
| Ser 340 | Ser | Ser | Gly | Ser | Gly 345 | Gly | Asn | Ser | Asn | Pro 350 | Gly | Ser | Pro | Thr | Pro |
| Trp 355 | Arg | Pro | Trp | Leu | Ala 360 | Thr | Glu | Gln | Ile | His 365 | Lys | Asp | Leu | Pro | Lys |
| Trp 370 | Ser | Ala | Ser | Ile | Leu 375 | Ile | Leu | Tyr | Asp | Ala 380 | Pro | Tyr | Ala | Arg | Asn |
| Arg 385 | Thr | Ala | Ile | Asp | Arg 390 | Val | Asp | His | Leu | Asp 395 | Pro | Lys | Ala | Met | Thr 400 |
| Ala 405 | Asn | Tyr | Pro | Pro | Ser 410 | Trp | Arg | Thr | Pro | Lys 415 | Trp | Asn | His | His | Gly |
| Leu 420 | Trp | Asp | Trp | Lys | Ala 425 | Arg | Asp | Val | Leu | Leu 430 | Gln | Thr | Thr | Gly | Phe |
| Phe 435 | Asn | Pro | Arg | Arg | His 440 | Pro | Glu | Trp | Phe | Asp 445 | Gly | Gly | Gln | Thr | Val |
| Ala 450 | Asp | Asn | Gly | Lys | Thr 455 | Gly | Phe | Asp | Val | Asp 460 | Asn | Ser | Glu | Asn | Thr |
| Lys 465 | Gln | Gly | Phe | Gln | Lys 470 | Glu | Ala | Asp | Ser | Asp 475 | Lys | Ser | Ala | Pro | Ile 480 |
| Ala 485 | Leu | Pro | Phe | Glu | Ala 490 | Tyr | Phe | Ala | Asn | Ile 495 | Gly | Asn | Leu | Thr | Trp |
| Phe 500 | Gly | Gln | Ala | Leu | Leu 505 | Val | Phe | Gly | Gly | Asn 510 | Gly | His | Val | Thr | Lys |
| Ser 515 | Ala | His | Thr | Ala | Pro 520 | Leu | Ser | Ile | Gly | Val 525 | Phe | Arg | Val | Arg | Tyr |
| Asn 530 | Ala | Thr | Gly | Thr | Ser 535 | Ala | Thr | Val | Thr | Gly 540 | Trp | Pro | Tyr | Ala | Leu |
| Leu 545 | Phe | Ser | Gly | Met | Val 550 | Asn | Lys | Gln | Thr | Asp 555 | Gly | Leu | Lys | Asp | Leu 560 |
| Pro 565 | Phe | Asn | Asn | Asn | Arg 570 | Trp | Phe | Glu | Tyr | Val 575 | Pro | Arg | Met | Ala | Val |
| Ala 580 | Gly | Ala | Lys | Phe | Val 585 | Gly | Arg | Glu | Leu | Val 590 | Leu | Ala | Gly | Thr | Ile |
| Thr 595 | Met | Gly | Asp | Thr | Ala 600 | Thr | Val | Pro | Arg | Leu 605 | Leu | Tyr | Asp | Glu | Leu |
| Glu 610 | Ser | Asn | Leu | Asn | Leu 615 | Val | Ala | Gln | Gly | Gln 620 | Gly | Leu | Leu | Arg | Glu |
| Asp 625 | Leu | Gln | Leu | Phe | Thr 630 | Pro | Tyr | Gly | Trp | Ala 635 | Asn | Arg | Pro | Asp | Leu 640 |
| Pro 645 | Ile | Gly | Ala | Trp | Ser 650 | Ser | Ser | Ser | Ser | Ser 655 | Ser | His | Asn | Ala | Pro |
| Tyr 660 | Tyr | Phe | His | Asn | Asn 665 | Pro | Asp | Trp | Gln | Asp 670 | Arg | Pro | Ile | Gln | Asn |
| Val 675 | Val | Asp | Ala | Phe | Ile 680 | Lys | Pro | Trp | Glu | Asp 685 | Lys | Asn | Gly | Lys | Asp |
| Asp 690 | Ala | Lys | Tyr | Ile | Tyr 695 | Pro | Tyr | Arg | Tyr | Ser 700 | Gly | Met | Trp | Ala | Trp |
| Gln 705 | Val | Tyr | Asn | Trp | Ser 710 | Asn | Lys | Leu | Thr | Asp 715 | Gln | Pro | Leu | Ser | Ala 720 |
| Asp 725 | Phe | Val | Asn | Glu | Asn 730 | Ala | Tyr | Gln | Pro | Asn 735 | Ser | Leu | Phe | Ala | Ala |
| Ile 740 | Leu | Asn | Pro | Glu | Leu 745 | Leu | Ala | Ala | Leu | Pro 750 | Asp | Lys | Val | Lys | Tyr |
| Gly | Lys | Glu | Asn | Glu | Phe | Ala | Ala | Asn | Glu | Tyr | Glu | Arg | Phe | Asn | Gln |

|     |     |     |     |     |     |     |     |     |     |     |     |     |     |     |
|-----|-----|-----|-----|-----|-----|-----|-----|-----|-----|-----|-----|-----|-----|-----|
| 755 |     |     |     |     | 760 |     |     |     |     | 765 |     |     |     |     |
| Lys | Leu | Thr | Val | Ala | Pro | Thr | Gln | Gly | Thr | Asn | Trp | Ser | His | Phe | Ser
| 770 |     |     |     |     | 775 |     |     |     |     | 780 |     |     |     |     |
| Pro | Thr | Leu | Ser | Arg | Phe | Ser | Thr | Gly | Phe | Asn | Leu | Val | Gly | Ser | Val
| 785 |     |     |     |     | 790 |     |     |     |     | 795 |     |     |     |     | 800
| Leu | Asp | Gln | Val | Leu | Asp | Tyr | Val | Pro | Trp | Ile | Gly | Asn | Gly | Tyr | Arg
| 805 |     |     |     |     | 810 |     |     |     |     | 815 |     |     |     |     |
| Tyr | Gly | Asn | Asn | His | Arg | Gly | Val | Asp | Asp | Ile | Thr | Ala | Pro | Gln | Thr
| 820 |     |     |     |     | 825 |     |     |     |     | 830 |     |     |     |     |
| Ser | Ala | Gly | Ser | Ser | Ser | Gly | Ile | Ser | Thr | Asn | Thr | Ser | Gly | Ser | Arg
| 835 |     |     |     |     | 840 |     |     |     |     | 845 |     |     |     |     |
| Ser | Phe | Leu | Pro | Thr | Phe | Ser | Asn | Ile | Gly | Val | Gly | Leu | Lys | Ala | Asn
| 850 |     |     |     |     | 855 |     |     |     |     | 860 |     |     |     |     |
| Val | Gln | Ala | Thr | Leu | Gly | Gly | Ser | Gln | Thr | Met | Ile | Thr | Gly | Gly | Ser
| 865 |     |     |     |     | 870 |     |     |     |     | 875 |     |     |     |     | 880
| Pro | Arg | Arg | Thr | Leu | Asp | Gln | Ala | Asn | Leu | Gln | Leu | Trp | Thr | Gly | Ala
| 885 |     |     |     |     | 890 |     |     |     |     | 895 |     |     |     |     |
| Gly | Trp | Arg | Asn | Asp | Lys | Ala | Ser | Ser | Gly | Gln | Ser | Asp | Glu | Asn | His
| 900 |     |     |     |     | 905 |     |     |     |     | 910 |     |     |     |     |
| Thr | Lys | Phe | Thr | Ser | Ala | Thr | Gly | Met | Asp | Gln | Gln | Gly | Gln | Ser | Gly
| 915 |     |     |     |     | 920 |     |     |     |     | 925 |     |     |     |     |
| Thr | Ser | Ala | Gly | Asn | Pro | Asp | Ser | Leu | Lys | Gln | Asp | Asn | Ile | Ser | Lys
| 930 |     |     |     |     | 935 |     |     |     |     | 940 |     |     |     |     |
| Ser | Gly | Asp | Ser | Leu | Thr | Thr | Gln | Asp | Gly | Asn | Ala | Ile | Asp | Gln | Gln
| 945 |     |     |     |     | 950 |     |     |     |     | 955 |     |     |     |     | 960
| Glu | Ala | Thr | Asn | Tyr | Thr | Asn | Leu | Pro | Pro | Asn | Leu | Thr | Pro | Thr | Ala
| 965 |     |     |     |     | 970 |     |     |     |     | 975 |     |     |     |     |
| Asp | Trp | Pro | Asn | Ala | Leu | Ser | Phe | Thr | Asn | Lys | Asn | Asn | Ala | Gln | Arg
| 980 |     |     |     |     | 985 |     |     |     |     | 990 |     |     |     |     |
| Ala | Gln | Leu | Phe | Leu | Arg | Gly | Leu | Leu | Gly | Ser | Ile | Pro | Val | Leu | Val
| 995 |     |     |     |     | 1000|     |     |     |     | 1005|     |     |     |     |
| Asn | Arg | Ser | Gly | Ser | Asp | Ser | Asn | Lys | Phe | Gln | Ala | Thr | Asp | Gln | Lys
| 1010|     |     |     |     | 1015|     |     |     |     | 1020|     |     |     |     |
| Trp | Ser | Tyr | Thr | Asp | Leu | His | Ser | Asp | Gln | Thr | Lys | Leu | Asn | Leu | Pro
| 1025|     |     |     |     | 1030|     |     |     |     | 1035|     |     |     |     | 1040
| Ala | Tyr | Gly | Glu | Val | Asn | Gly | Leu | Leu | Asn | Pro | Ala | Leu | Val | Glu | Thr
| 1045|     |     |     |     | 1050|     |     |     |     | 1055|     |     |     |     |
| Tyr | Phe | Gly | Asn | Thr | Arg | Ala | Gly | Gly | Ser | Gly | Ser | Asn | Thr | Thr | Ser
| 1060|     |     |     |     | 1065|     |     |     |     | 1070|     |     |     |     |
| Ser | Pro | Gly | Ile | Gly | Phe | Lys | Ile | Pro | Glu | Gln | Asn | Asn | Asp | Ser | Lys
| 1075|     |     |     |     | 1080|     |     |     |     | 1085|     |     |     |     |
| Ala | Thr | Leu | Ile | Thr | Pro | Gly | Leu | Ala | Trp | Thr | Pro | Gln | Asp | Val | Gly
| 1090|     |     |     |     | 1095|     |     |     |     | 1100|     |     |     |     |
| Asn | Leu | Val | Val | Ser | Gly | Thr | Thr | Val | Ser | Phe | Gln | Leu | Gly | Gly | Trp
| 1105|     |     |     |     | 1110|     |     |     |     | 1115|     |     |     |     | 1120
| Leu | Val | Thr | Phe | Thr | Asp | Phe | Val | Lys | Pro | Arg | Ala | Gly | Tyr | Leu | Gly
| 1125|     |     |     |     | 1130|     |     |     |     | 1135|     |     |     |     |
| Leu | Gln | Leu | Thr | Gly | Leu | Asp | Ala | Ser | Asp | Ala | Thr | Gln | Arg | Ala | Leu
| 1140|     |     |     |     | 1145|     |     |     |     | 1150|     |     |     |     |
| Ile | Trp | Ala | Pro | Arg | Pro | Trp | Ala | Ala | Phe | Arg | Gly | Ser | Trp | Val | Asn
| 1155|     |     |     |     | 1160|     |     |     |     | 1165|     |     |     |     |
| Arg | Leu | Gly | Arg | Val | Glu | Ser | Val | Trp | Asp | Leu | Lys | Gly | Val | Trp | Ala
| 1170|     |     |     |     | 1175|     |     |     |     | 1180|     |     |     |     |
| Asp | Gln | Ala | Gln | Ser | Asp | Ser | Gln | Gly | Ser | Thr | Thr | Thr | Ala | Thr | Arg
| 1185|     |     |     |     | 1190|     |     |     |     | 1195|     |     |     |     | 1200

```
Asn Ala Leu Pro Glu His Pro Asn Ala Leu Ala Phe Gln Val Ser Val
1205            1210            1215

Val Glu Ala Ser Ala Tyr Lys Pro Asn Thr Ser Ser Gly Gln Thr Gln
1220            1225            1230

Ser Thr Asn Ser Ser Pro Tyr Leu His Leu Val Lys Pro Lys Lys Val
1235            1240            1245

Thr Gln Ser Asp Lys Leu Asp Asp Asp Leu Lys Asn Leu Leu Asp Pro
1250            1255            1260

Asn Gln Val Arg Thr Lys Leu Arg Gln Ser Phe Gly Thr Asp His Ser
1265            1270            1275                1280

Thr Gln Pro Gln Pro Gln Ser Leu Lys Thr Thr Thr Pro Val Phe Gly
1285            1290            1295

Thr Ser Ser Gly Asn Leu Ser Ser Val Leu Ser Gly Gly Gly Ala Gly
1300            1305            1310

Gly Gly Ser Ser Gly Ser Gly Gln Ser Gly Val Asp Leu Ser Pro Val
1315            1320            1325

Glu Lys Val Ser Gly Trp Leu Val Gly Gln Leu Pro Ser Thr Ser Asp
1330            1335            1340

Gly Asn Thr Ser Ser Thr Asn Asn Leu Ala Pro Asn Thr Asn Thr Gly
1345            1350            1355                1360

Asn Asp Val Val Gly Val Gly Arg Leu Ser Glu Ser Asn Ala Ala Lys
1365            1370            1375

Met Asn Asp Asp Val Asp Gly Ile Val Arg Thr Pro Leu Ala Glu Leu
1380            1385            1390

Leu Asp Gly Glu Gly Gln Thr Ala Asp Thr Gly Pro Gln Ser Val Lys
1395            1400            1405

Phe Lys Ser Pro Asp Gln Ile Asp Phe Asn Arg Leu Phe Thr His Pro
1410            1415            1420

Val Thr Asp Leu Phe Asp Pro Val Thr Met Leu Val Tyr Asp Gln Tyr
1425            1430            1435                1440

Ile Pro Leu Phe Ile Asp Ile Pro Ala Ser Val Asn Pro Lys Met Val
1445            1450            1455

Arg Leu Lys Val Leu Ser Phe Asp Thr Asn Glu Gln Ser Leu Gly Leu
1460            1465            1470

Arg Leu Glu Phe Phe Lys Pro Asp Gln Asp Thr Gln Pro Asn Asn Asn
1475            1480            1485

Val Gln Val Asn Pro Asn Asn Gly Asp Phe Leu Pro Leu Leu Thr Ala
1490            1495            1500

Ser Ser Gln Gly Pro Gln Thr Leu Phe Ser Pro Phe Asn Gln Trp Pro
1505            1510            1515                1520

Asp Tyr Val Leu Pro Leu Ala Ile Thr Val Pro Ile Val Val Ile Val
1525            1530            1535

Leu Ser Val Thr Leu Gly Leu Ala Ile Gly Ile Pro Met His Lys Asn
1540            1545            1550

Lys Gln Ala Leu Lys Ala Gly Phe Ala Leu Ser Asn Gln Lys Val Asp
1555            1560            1565

Val Leu Thr Lys Ala Val Gly Ser Val Phe Lys Glu Ile Ile Asn Arg
1570            1575            1580

Thr Gly Ile Ser Gln Ala Pro Lys Arg Leu Lys Gln Thr Ser Ala Ala
1585            1590            1595                1600

Lys Pro Gly Ala Pro Arg Pro Pro Val Pro Pro Lys Pro Gly Ala Pro
1605            1610            1615

Lys Pro Pro Val Gln Pro Pro Lys Lys Pro Ala
1620            1625
```

(2) INFORMATION FOR SEQ ID NO:10:

(i) SEQUENCE CHARACTERISTICS:
        (A) LENGTH: 4884 Nucleotides
        (B) TYPE: Nucleic Acid
        (C) STRANDEDNESS: Single
        (D) TOPOLOGY: Linear (ii) MOLECULE TYPE: Genomic DNA
        (A) DESCRIPTION: Nucleic Acid Sequence of P1 Protein (iii) HYPOTHETICAL: No (vi) ORIGINAL SOURCE:
        (A) ORGANISM: Mycoplasma pneumoniae
        (B) STRAIN: M129-B16

(vii) IMMEDIATE SOURCE:
        (B) CLONE: Gene cloned in pUC19 in E. coli HB101, ATCC
            Accession Number 67560

(ix) FEATURE:
        (A) NAME/KEY: Nucleic Acid Sequence of P1 Protein
        (B) LOCATION: Nucleotide Numbers: 1 to 4884

(xi) SEQUENCE DESCRIPTION: SEQ ID NO:10:

```
ATG CAC CAA ACC AAA AAA ACT GCC TTG TCC AAG TCC ACT TGG ATT CTC        48
Met His Gln Thr Lys Lys Thr Ala Leu Ser Lys Ser Thr Trp Ile Leu
1               5                   10                  15

ATC CTC ACC GCC ACC GCC TCC CTC GCG ACG GGA CTC ACC GTA GTG GGA        96
Ile Leu Thr Ala Thr Ala Ser Leu Ala Thr Gly Leu Thr Val Val Gly
20              25                  30

CAC TTC ACA AGT ACC ACC ACG ACG CTC AAG CGC CAG CAA TTT AGC TAC       144
His Phe Thr Ser Thr Thr Thr Thr Leu Lys Arg Gln Gln Phe Ser Tyr
35              40                  45

ACC CGC CCT GAC GAG GTC GCG CTG CGC CAC ACC AAT GCC ATC AAC CCG       192
Thr Arg Pro Asp Glu Val Ala Leu Arg His Thr Asn Ala Ile Asn Pro
50              55                  60

CGC TTA ACC CCG TGA ACG TAT CGT AAC ACG AGC TTT TCC TCC CTC CCC       240
Arg Leu Thr Pro Trp Thr Tyr Arg Asn Thr Ser Phe Ser Ser Leu Pro
65              70                  75                  80

CTC ACG GGT GAA AAT CCC GGG GCG TGG GCC TTA GTG CGC GAC AAC AGC       288
Leu Thr Gly Glu Asn Pro Gly Ala Trp Ala Leu Val Arg Asp Asn Ser
85              90                  95

GCT AAG GGC ATC ACT GCC GGC AGT GGC AGT CAA CAA ACC ACG TAT GAT       336
Ala Lys Gly Ile Thr Ala Gly Ser Gly Ser Gln Gln Thr Thr Tyr Asp
100             105                 110

CCC ACC CGA ACC GAA GCG GCT TTG ACC GCA TCA ACC ACC TTT GCG TTA       384
Pro Thr Arg Thr Glu Ala Ala Leu Thr Ala Ser Thr Thr Phe Ala Leu
115             120                 125

CGC CGG TAT GAC CTC GCC GGG CGC GCC TTA TAC GAC CTC GAT TTT TCG       432
Arg Arg Tyr Asp Leu Ala Gly Arg Ala Leu Tyr Asp Leu Asp Phe Ser
130             135                 140

AAG TTA AAC CCG CAA ACG CCC ACG CGC GAC CAA ACC GGG CAG ATC ACC       480
Lys Leu Asn Pro Gln Thr Pro Thr Arg Asp Gln Thr Gly Gln Ile Thr
145             150                 155                 160

TTT AAC CCC TTT GGC GGC TTT GGT TTG AGT GGG GCT GCA CCC CAA CAG       528
Phe Asn Pro Phe Gly Gly Phe Gly Leu Ser Gly Ala Ala Pro Gln Gln
165             170                 175

TGA AAC GAG GTC AAA AAC AAG GTC CCC GTC GAG GTG GCG CAA GAC CCC       576
Trp Asn Glu Val Lys Asn Lys Val Pro Val Glu Val Ala Gln Asp Pro
180             185                 190

TCC AAT CCC TAC CGG TTT GCC GTT TTA CTC GTG CCG CGC AGC GTG GTG       624
Ser Asn Pro Tyr Arg Phe Ala Val Leu Leu Val Pro Arg Ser Val Val
195             200                 205

TAC TAT GAG CAG TTG CAA AGG GGG TTG GGC TTA CCA CAG CAG CGA ACC       672
Tyr Tyr Glu Gln Leu Gln Arg Gly Leu Gly Leu Pro Gln Gln Arg Thr
```

-continued

| 210 | | | | | 215 | | | | | 220 | | | | | |
|---|---|---|---|---|---|---|---|---|---|---|---|---|---|---|---|
| GAG | AGT | GGT | CAA | AAT | ACT | TCC | ACC | ACC | GGG | GCA | ATG | TTT | GGC | TTG | AAG | 720
| Glu | Ser | Gly | Gln | Asn | Thr | Ser | Thr | Thr | Gly | Ala | Met | Phe | Gly | Leu | Lys |
| 225 | | | | | 230 | | | | | 235 | | | | | 240 |
| GTG | AAG | AAC | GCC | GAG | GCG | GAC | ACC | GCG | AAG | AGC | AAT | GAA | AAA | CTC | CAG | 768
| Val | Lys | Asn | Ala | Glu | Ala | Asp | Thr | Ala | Lys | Ser | Asn | Glu | Lys | Leu | Gln |
| 245 | | | | | 250 | | | | | 255 | | | | | |
| GGC | GCT | GAG | GCC | ACT | GGT | TCT | TCA | ACC | ACA | TCT | GGA | TCT | GGC | CAA | TCC | 816
| Gly | Ala | Glu | Ala | Thr | Gly | Ser | Ser | Thr | Thr | Ser | Gly | Ser | Gly | Gln | Ser |
| 260 | | | | | 265 | | | | | 270 | | | | | |
| ACC | CAA | CGT | GGG | GGT | TCG | TCA | GGG | GAC | ACC | AAA | GTC | AAG | GCT | TTA | AAA | 864
| Thr | Gln | Arg | Gly | Gly | Ser | Ser | Gly | Asp | Thr | Lys | Val | Lys | Ala | Leu | Lys |
| 275 | | | | | 280 | | | | | 285 | | | | | |
| ATA | GAG | GTG | AAA | AAG | AAA | TCG | GAC | TCG | GAG | GAC | AAT | GGT | CAG | CTG | CAG | 912
| Ile | Glu | Val | Lys | Lys | Lys | Ser | Asp | Ser | Glu | Asp | Asn | Gly | Gln | Leu | Gln |
| 290 | | | | | 295 | | | | | 300 | | | | | |
| TTA | GAA | AAA | AAT | GAT | CTC | GCC | AAC | GCT | CCC | ATT | AAG | CGG | AGC | GAG | GAG | 960
| Leu | Glu | Lys | Asn | Asp | Leu | Ala | Asn | Ala | Pro | Ile | Lys | Arg | Ser | Glu | Glu |
| 305 | | | | | 310 | | | | | 315 | | | | | 320 |
| TCG | GGT | CAG | TCC | GTC | CAA | CTC | AAG | GCG | GAC | GAT | TTT | GGT | ACT | GCC | CTT | 1008
| Ser | Gly | Gln | Ser | Val | Gln | Leu | Lys | Ala | Asp | Asp | Phe | Gly | Thr | Ala | Leu |
| 325 | | | | | 330 | | | | | 335 | | | | | |
| TCC | AGT | TCG | GGA | TCA | GGC | GGC | AAC | TCC | AAT | CCC | GGT | TCC | CCC | ACC | CCC | 1056
| Ser | Ser | Ser | Gly | Ser | Gly | Gly | Asn | Ser | Asn | Pro | Gly | Ser | Pro | Thr | Pro |
| 340 | | | | | 345 | | | | | 350 | | | | | |
| TGA | AGG | CCG | TGG | CTT | GCG | ACT | GAG | CAA | ATT | CAC | AAG | GAC | CTC | CCC | AAA | 1104
| Trp | Arg | Pro | Trp | Leu | Ala | Thr | Glu | Gln | Ile | His | Lys | Asp | Leu | Pro | Lys |
| 355 | | | | | 360 | | | | | 365 | | | | | |
| TGA | TCC | GCC | TCG | ATC | CTG | ATT | CTG | TAC | GAT | GCG | CCT | TAT | GCG | CGC | AAC | 1152
| Trp | Ser | Ala | Ser | Ile | Leu | Ile | Leu | Tyr | Asp | Ala | Pro | Tyr | Ala | Arg | Asn |
| 370 | | | | | 375 | | | | | 380 | | | | | |
| CGT | ACC | GCC | ATT | GAC | CGC | GTT | GAT | CAC | TTG | GAT | CCC | AAG | GCC | ATG | ACC | 1200
| Arg | Thr | Ala | Ile | Asp | Arg | Val | Asp | His | Leu | Asp | Pro | Lys | Ala | Met | Thr |
| 385 | | | | | 390 | | | | | 395 | | | | | 400 |
| GCG | AAC | TAT | CCG | CCC | AGT | TGA | AGA | ACG | CCC | AAG | TGA | AAC | CAC | CAC | GGT | 1248
| Ala | Asn | Tyr | Pro | Pro | Ser | Trp | Arg | Thr | Pro | Lys | Trp | Asn | His | His | Gly |
| 405 | | | | | 410 | | | | | 415 | | | | | |
| TTG | TGG | GAC | TGA | AAG | GCG | CGC | GAT | GTT | TTG | CTC | CAA | ACC | ACC | GGG | TTC | 1296
| Leu | Trp | Asp | Trp | Lys | Ala | Arg | Asp | Val | Leu | Leu | Gln | Thr | Thr | Gly | Phe |
| 420 | | | | | 425 | | | | | 430 | | | | | |
| TTC | AAC | CCG | CGC | CGC | CAC | CCC | GAG | TGG | TTT | GAT | GGC | GGG | CAG | ACG | GTC | 1344
| Phe | Asn | Pro | Arg | Arg | His | Pro | Glu | Trp | Phe | Asp | Gly | Gly | Gln | Thr | Val |
| 435 | | | | | 440 | | | | | 445 | | | | | |
| GCG | GAT | AAC | GAA | AAG | ACC | GGG | TTT | GAT | GTG | GAT | AAC | TCT | GAA | AAC | ACC | 1392
| Ala | Asp | Asn | Gly | Lys | Thr | Gly | Phe | Asp | Val | Asp | Asn | Ser | Glu | Asn | Thr |
| 450 | | | | | 455 | | | | | 460 | | | | | |
| AAG | CAG | GGC | TTT | CAA | AAG | GAA | GCT | GAC | TCC | GAC | AAG | TCG | GCC | CCG | ATC | 1440
| Lys | Gln | Gly | Phe | Gln | Lys | Glu | Ala | Asp | Ser | Asp | Lys | Ser | Ala | Pro | Ile |
| 465 | | | | | 470 | | | | | 475 | | | | | 480 |
| GCC | CTC | CCG | TTT | GAA | GCG | TAC | TTC | GCC | AAC | ATT | GGC | AAC | CTC | ACC | TGG | 1488
| Ala | Leu | Pro | Phe | Glu | Ala | Tyr | Phe | Ala | Asn | Ile | Gly | Asn | Leu | Thr | Trp |
| 485 | | | | | 490 | | | | | 495 | | | | | |
| TTC | GGG | CAA | GCG | CTT | TTG | GTG | TTT | GGT | GGC | AAT | GGC | CAT | GTT | ACC | AAG | 1536
| Phe | Gly | Gln | Ala | Leu | Leu | Val | Phe | Gly | Gly | Asn | Gly | His | Val | Thr | Lys |
| 500 | | | | | 505 | | | | | 510 | | | | | |
| TCG | GCC | CAC | ACC | GCG | CCT | TTG | AGT | ATA | GGT | GTC | TTT | AGG | GTG | CGC | TAT | 1584
| Ser | Ala | His | Thr | Ala | Pro | Leu | Ser | Ile | Gly | Val | Phe | Arg | Val | Arg | Tyr |
| 515 | | | | | 520 | | | | | 525 | | | | | |
| AAT | GCA | ACT | GGT | ACC | AGT | GCT | ACT | GTA | ACT | GGT | TGA | CCA | TAT | GCC | TTA | 1632
| Asn | Ala | Thr | Gly | Thr | Ser | Ala | Thr | Val | Thr | Gly | Trp | Pro | Tyr | Ala | Leu |
| 530 | | | | | 535 | | | | | 540 | | | | | |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| CTG | TTC | TCA | GGC | ATG | GTC | AAC | AAA | CAA | ACT | GAC | GGG | TTA | AAG | GAT | CTA | 1680 |
| Leu | Phe | Ser | Gly | Met | Val | Asn | Lys | Gln | Thr | Asp | Gly | Leu | Lys | Asp | Leu |      |
| 545 |     |     |     |     | 550 |     |     |     |     | 555 |     |     |     |     | 560 |      |
| CCC | TTT | AAC | AAT | AAC | CGC | TGG | TTT | GAA | TAT | GTA | CCA | CGG | ATG | GCA | GTT | 1728 |
| Pro | Phe | Asn | Asn | Asn | Arg | Trp | Phe | Glu | Tyr | Val | Pro | Arg | Met | Ala | Val |      |
| 565 |     |     |     | 570 |     |     |     |     | 575 |     |     |     |     |     |     |      |
| GCT | GGC | GCT | AAG | TTC | GTT | GGT | AGG | GAA | CTC | GTT | TTA | GCG | GGT | ACC | ATT | 1776 |
| Ala | Gly | Ala | Lys | Phe | Val | Gly | Arg | Glu | Leu | Val | Leu | Ala | Gly | Thr | Ile |      |
| 580 |     |     |     |     | 585 |     |     |     |     | 590 |     |     |     |     |     |      |
| ACC | ATG | GGT | GAT | ACC | GCT | ACC | GTA | CCT | CGC | TTA | CTG | TAC | GAT | GAA | CTT | 1824 |
| Thr | Met | Gly | Asp | Thr | Ala | Thr | Val | Pro | Arg | Leu | Leu | Tyr | Asp | Glu | Leu |      |
| 595 |     |     |     |     | 600 |     |     |     |     | 605 |     |     |     |     |     |      |
| GAA | AGC | AAC | CTG | AAC | TTA | GTA | GCG | CAA | GGC | CAA | GGT | CTT | TTA | CGC | GAA | 1872 |
| Glu | Ser | Asn | Leu | Asn | Leu | Val | Ala | Gln | Gly | Gln | Gly | Leu | Leu | Arg | Glu |      |
| 610 |     |     |     |     | 615 |     |     |     |     | 620 |     |     |     |     |     |      |
| GAC | TTG | CAA | CTC | TTC | ACA | CCC | TAC | GGA | TGA | GCC | AAT | CGT | CCG | GAT | TTA | 1920 |
| Asp | Leu | Gln | Leu | Phe | Thr | Pro | Tyr | Gly | Trp | Ala | Asn | Arg | Pro | Asp | Leu |      |
| 625 |     |     |     |     | 630 |     |     |     |     | 635 |     |     |     |     | 640 |      |
| CCA | ATC | GGG | GCT | TGA | AGT | AGT | AGT | AGT | AGT | AGT | AGT | CAC | AAC | GCA | CCC | 1968 |
| Pro | Ile | Gly | Ala | Trp | Ser | Ser | Ser | Ser | Ser | Ser | Ser | His | Asn | Ala | Pro |      |
| 645 |     |     |     |     | 650 |     |     |     |     | 655 |     |     |     |     |     |      |
| TAC | TAC | TTC | CAC | AAT | AAC | CCC | GAT | TGA | CAA | GAC | CGT | CCA | ATC | CAA | AAT | 2016 |
| Tyr | Tyr | Phe | His | Asn | Asn | Pro | Asp | Trp | Gln | Asp | Arg | Pro | Ile | Gln | Asn |      |
| 660 |     |     |     |     | 665 |     |     |     |     | 670 |     |     |     |     |     |      |
| GTG | GTT | GAT | GCC | TTT | ATT | AAG | CCC | TGA | GAG | GAC | AAG | AAC | GGT | AAG | GAT | 2064 |
| Val | Val | Asp | Ala | Phe | Ile | Lys | Pro | Trp | Glu | Asp | Lys | Asn | Gly | Lys | Asp |      |
| 675 |     |     |     |     | 680 |     |     |     |     | 685 |     |     |     |     |     |      |
| GAT | GCC | AAA | TAC | ATC | TAC | CCT | TAC | CGT | TAC | AGT | GGC | ATG | TGA | GCT | TGA | 2112 |
| Asp | Ala | Lys | Tyr | Ile | Tyr | Pro | Tyr | Arg | Tyr | Ser | Gly | Met | Trp | Ala | Trp |      |
| 690 |     |     |     |     | 695 |     |     |     |     | 700 |     |     |     |     |     |      |
| CAG | GTA | TAC | AAC | TGG | TCC | AAT | AAG | CTC | ACT | GAC | CAA | CCA | TTA | AGT | GCT | 2160 |
| Gln | Val | Tyr | Asn | Trp | Ser | Asn | Lys | Leu | Thr | Asp | Gln | Pro | Leu | Ser | Ala |      |
| 705 |     |     |     |     | 710 |     |     |     |     | 715 |     |     |     |     | 720 |      |
| GAC | TTT | GTC | AAT | GAG | AAT | GCT | TAC | CAA | CCA | AAC | TCC | TTG | TTT | GCT | GCT | 2208 |
| Asp | Phe | Val | Asn | Glu | Asn | Ala | Tyr | Gln | Pro | Asn | Ser | Leu | Phe | Ala | Ala |      |
| 725 |     |     |     |     | 730 |     |     |     |     | 735 |     |     |     |     |     |      |
| ATT | CTC | AAT | CCG | GAA | TTG | TTA | GCA | GCT | CTT | CCC | GAC | AAG | GTT | AAA | TAC | 2256 |
| Ile | Leu | Asn | Pro | Glu | Leu | Leu | Ala | Ala | Leu | Pro | Asp | Lys | Val | Lys | Tyr |      |
| 740 |     |     |     |     | 745 |     |     |     |     | 750 |     |     |     |     |     |      |
| GGT | AAG | GAA | AAC | GAG | TTT | GCT | GCT | AAC | GAG | TAC | GAG | CGC | TTT | AAC | CAG | 2304 |
| Gly | Lys | Glu | Asn | Glu | Phe | Ala | Ala | Asn | Glu | Tyr | Glu | Arg | Phe | Asn | Gln |      |
| 755 |     |     |     |     | 760 |     |     |     |     | 765 |     |     |     |     |     |      |
| AAG | TTA | ACG | GTA | GCT | CCT | ACC | CAA | GGA | ACA | AAC | TGA | TCC | CAC | TTC | TCC | 2352 |
| Lys | Leu | Thr | Val | Ala | Pro | Thr | Gln | Gly | Thr | Asn | Trp | Ser | His | Phe | Ser |      |
| 770 |     |     |     |     | 775 |     |     |     |     | 780 |     |     |     |     |     |      |
| CCC | ACG | CTT | TCC | CGT | TTC | TCC | ACC | GGG | TTC | AAC | CTT | GTG | GGG | TCG | GTG | 2400 |
| Pro | Thr | Leu | Ser | Arg | Phe | Ser | Thr | Gly | Phe | Asn | Leu | Val | Gly | Ser | Val |      |
| 785 |     |     |     |     | 790 |     |     |     |     | 795 |     |     |     |     | 800 |      |
| CTC | GAC | CAG | GTG | TTG | GAT | TAT | GTG | CCC | TGG | ATT | GGG | AAT | GGG | TAC | AGG | 2448 |
| Leu | Asp | Gln | Val | Leu | Asp | Tyr | Val | Pro | Trp | Ile | Gly | Asn | Gly | Tyr | Arg |      |
| 805 |     |     |     |     | 810 |     |     |     |     | 815 |     |     |     |     |     |      |
| TAT | GGC | AAT | AAC | CAC | CGG | GGC | GTG | GAT | GAT | ATA | ACC | GCG | CCT | CAA | ACC | 2496 |
| Tyr | Gly | Asn | Asn | His | Arg | Gly | Val | Asp | Asp | Ile | Thr | Ala | Pro | Gln | Thr |      |
| 820 |     |     |     |     | 825 |     |     |     |     | 830 |     |     |     |     |     |      |
| AGC | GCG | GGG | TCG | TCC | AGC | GGA | ATT | AGT | ACG | AAC | ACA | AGT | GGT | TCG | CGT | 2544 |
| Ser | Ala | Gly | Ser | Ser | Ser | Gly | Ile | Ser | Thr | Asn | Thr | Ser | Gly | Ser | Arg |      |
| 835 |     |     |     |     | 840 |     |     |     |     | 845 |     |     |     |     |     |      |
| TCC | TTT | CTC | CCG | ACG | TTT | TCC | AAC | ATC | GGC | GTC | GGC | CTC | AAA | GCG | AAT | 2592 |
| Ser | Phe | Leu | Pro | Thr | Phe | Ser | Asn | Ile | Gly | Val | Gly | Leu | Lys | Ala | Asn |      |
| 850 |     |     |     |     | 855 |     |     |     |     | 860 |     |     |     |     |     |      |
| GTC | CAA | GCC | ACC | CTC | GGG | GGC | AGT | CAG | ACG | ATG | ATT | ACA | GGC | GGT | TCG | 2640 |
| Val | Gln | Ala | Thr | Leu | Gly | Gly | Ser | Gln | Thr | Met | Ile | Thr | Gly | Gly | Ser |      |

| | | | | |
|---|---|---|---|---|
| 865 | | 870 | 875 | 880 |

```
CCT CGA AGA ACC CTC GAC CAA GCC AAC CTC CAG CTC TGA ACG GGG GCG   2688
Pro Arg Arg Thr Leu Asp Gln Ala Asn Leu Gln Leu Trp Thr Gly Ala
885                 890                 895

GGG TGA AGG AAT GAT AAG GCT TCA AGT GGA CAA AGT GAC GAA AAC CAC   2736
Gly Trp Arg Asn Asp Lys Ala Ser Ser Gly Gln Ser Asp Glu Asn His
900                 905                 910

ACC AAG TTC ACG AGC GCT ACG GGG ATG GAC CAG CAG GGA CAA TCA GGT   2784
Thr Lys Phe Thr Ser Ala Thr Gly Met Asp Gln Gln Gly Gln Ser Gly
915                 920                 925

ACC TCC GCG GGG AAT CCC GAC TCG TTA AAG CAG GAT AAT ATT AGT AAG   2832
Thr Ser Ala Gly Asn Pro Asp Ser Leu Lys Gln Asp Asn Ile Ser Lys
930                 935                 940

AGT GGG GAT AGT TTA ACC ACG CAG GAC GGC AAT GCG ATC GAT CAA CAA   2880
Ser Gly Asp Ser Leu Thr Thr Gln Asp Gly Asn Ala Ile Asp Gln Gln
945                 950                 955                 960

GAG GCC ACC AAC TAC ACC AAC CTC CCC CCC AAC CTC ACC CCC ACC GCT   2928
Glu Ala Thr Asn Tyr Thr Asn Leu Pro Pro Asn Leu Thr Pro Thr Ala
965                 970                 975

GAT TGA CCG AAC GCG CTG TCA TTC ACC AAC AAG AAC AAC GCG CAG CGC   2976
Asp Trp Pro Asn Ala Leu Ser Phe Thr Asn Lys Asn Asn Ala Gln Arg
980                 985                 990

GCC CAG CTC TTC CTC CGC GGC TTG TTG GGC AGC ATC CCG GTG TTG GTG   3024
Ala Gln Leu Phe Leu Arg Gly Leu Leu Gly Ser Ile Pro Val Leu Val
995                 1000                1005

AAT CGA AGT GGG TCC GAT TCC AAC AAA TTC CAA GCC ACC GAC CAA AAA   3072
Asn Arg Ser Gly Ser Asp Ser Asn Lys Phe Gln Ala Thr Asp Gln Lys
1010                1015                1020

TGG TCC TAC ACC GAC TTA CAT TCG GAC CAA ACC AAA CTG AAC CTC CCC   3120
Trp Ser Tyr Thr Asp Leu His Ser Asp Gln Thr Lys Leu Asn Leu Pro
1025                1030                1035                1040

GCT TAC GGT GAG GTG AAT GGG TTG TTG AAT CCG GCG TTG GTG GAA ACC   3168
Ala Tyr Gly Glu Val Asn Gly Leu Leu Asn Pro Ala Leu Val Glu Thr
1045                1050                1055

TAT TTT GGG AAC ACG CGA GCG GGT GGT TCG GGG TCC AAC ACG ACC AGT   3216
Tyr Phe Gly Asn Thr Arg Ala Gly Gly Ser Gly Ser Asn Thr Thr Ser
1060                1065                1070

TCA CCC GGT ATC GGT TTT AAA ATT CCC GAA CAA AAT AAT GAT TCC AAA   3264
Ser Pro Gly Ile Gly Phe Lys Ile Pro Glu Gln Asn Asn Asp Ser Lys
1075                1080                1085

GCC ACC CTG ATC ACC CCC GGG TTG GCT TGA ACG CCC CAG GAC GTC GGT   3312
Ala Thr Leu Ile Thr Pro Gly Leu Ala Trp Thr Pro Gln Asp Val Gly
1090                1095                1100

AAC CTC GTT GTC AGT GGC ACC ACG GTG AGC TTC CAG CTC GGC GGG TGG   3360
Asn Leu Val Val Ser Gly Thr Thr Val Ser Phe Gln Leu Gly Gly Trp
1105                1110                1115                1120

CTG GTC ACC TTC ACG GAC TTT GTC AAA CCC CGC GCG GGT TAC CTC GGT   3408
Leu Val Thr Phe Thr Asp Phe Val Lys Pro Arg Ala Gly Tyr Leu Gly
1125                1130                1135

CTC CAG TTA ACG GGC TTG GAT GCA AGT GAT GCG ACG CAG CGC GCC CTC   3456
Leu Gln Leu Thr Gly Leu Asp Ala Ser Asp Ala Thr Gln Arg Ala Leu
1140                1145                1150

ATT TGG GCC CCC CGG CCC TGA GCG GCC TTT CGT GGC AGT TGG GTC AAC   3504
Ile Trp Ala Pro Arg Pro Trp Ala Ala Phe Arg Gly Ser Trp Val Asn
1155                1160                1165

CGG TTG GGC CGC GTG GAG AGT GTG TGG GAT TTG AAG GGG GTG TGG GCG   3552
Arg Leu Gly Arg Val Glu Ser Val Trp Asp Leu Lys Gly Val Trp Ala
1170                1175                1180

GAT CAA GCT CAG TCC GAC TCG CAA GGA TCT ACC ACC ACC GCA ACA AGG   3600
Asp Gln Ala Gln Ser Asp Ser Gln Gly Ser Thr Thr Thr Ala Thr Arg
1185                1190                1195                1200
```

| | | | | | | | | | | | | | | | | |
|---|---|---|---|---|---|---|---|---|---|---|---|---|---|---|---|---|
| AAC | GCC | TTA | CCG | GAG | CAC | CCG | AAT | GCT | TTG | GCC | TTT | CAG | GTG | AGT | GTG | 3648 |
| Asn | Ala | Leu | Pro | Glu | His | Pro | Asn | Ala | Leu | Ala | Phe | Gln | Val | Ser | Val | |
| 1205 | | | | 1210 | | | | | 1215 | | | | | | | |
| GTG | GAA | GCG | AGT | GCT | TAC | AAG | CCA | AAC | ACG | AGC | TCC | GGC | CAA | ACC | CAA | 3696 |
| Val | Glu | Ala | Ser | Ala | Tyr | Lys | Pro | Asn | Thr | Ser | Ser | Gly | Gln | Thr | Gln | |
| 1220 | | | | | 1225 | | | | 1230 | | | | | | | |
| TCC | ACT | AAC | AGT | TCC | CCC | TAC | CTG | CAC | TTG | GTG | AAG | CCT | AAG | AAA | GTT | 3744 |
| Ser | Thr | Asn | Ser | Ser | Pro | Tyr | Leu | His | Leu | Val | Lys | Pro | Lys | Lys | Val | |
| 1235 | | | | | 1240 | | | | | 1245 | | | | | | |
| ACC | CAA | TCC | GAC | AAG | TTA | GAC | GAC | GAT | CTT | AAA | AAC | CTG | TTG | GAC | CCC | 3792 |
| Thr | Gln | Ser | Asp | Lys | Leu | Asp | Asp | Asp | Leu | Lys | Asn | Leu | Leu | Asp | Pro | |
| 1250 | | | | | 1255 | | | | | 1260 | | | | | | |
| AAC | CAG | GTT | CGC | ACC | AAG | CTG | CGC | CAA | AGC | TTT | GGT | ACA | GAC | CAT | TCC | 3840 |
| Asn | Gln | Val | Arg | Thr | Lys | Leu | Arg | Gln | Ser | Phe | Gly | Thr | Asp | His | Ser | |
| 1265 | | | | | 1270 | | | | | 1275 | | | | | 1280 | |
| ACC | CAG | CCC | CAG | CCC | CAA | TCG | CTC | AAA | ACA | ACG | ACA | CCG | GTA | TTT | GGG | 3888 |
| Thr | Gln | Pro | Gln | Pro | Gln | Ser | Leu | Lys | Thr | Thr | Thr | Pro | Val | Phe | Gly | |
| 1285 | | | | | 1290 | | | | | 1295 | | | | | | |
| ACG | AGT | AGT | GGT | AAC | CTC | AGT | AGT | GTG | CTT | AGT | GGT | GGG | GGT | GCT | GGA | 3936 |
| Thr | Ser | Ser | Gly | Asn | Leu | Ser | Ser | Val | Leu | Ser | Gly | Gly | Gly | Ala | Gly | |
| 1300 | | | | | 1305 | | | | | 1310 | | | | | | |
| GGG | GGT | TCT | TCA | GGC | TCA | GGT | CAA | TCT | GGC | GTG | GAT | CTC | TCC | CCC | GTT | 3984 |
| Gly | Gly | Ser | Ser | Gly | Ser | Gly | Gln | Ser | Gly | Val | Asp | Leu | Ser | Pro | Val | |
| 1315 | | | | | 1320 | | | | | 1325 | | | | | | |
| GAA | AAA | GTG | AGT | GGG | TGG | CTT | GTG | GGG | CAG | TTA | CCA | AGC | ACG | AGT | GAC | 4032 |
| Glu | Lys | Val | Ser | Gly | Trp | Leu | Val | Gly | Gln | Leu | Pro | Ser | Thr | Ser | Asp | |
| 1330 | | | | | 1335 | | | | | 1340 | | | | | | |
| GGA | AAC | ACC | TCC | TCC | ACC | AAC | AAC | CTC | GCG | CCT | AAT | ACT | AAT | ACG | GGG | 4080 |
| Gly | Asn | Thr | Ser | Ser | Thr | Asn | Asn | Leu | Ala | Pro | Asn | Thr | Asn | Thr | Gly | |
| 1345 | | | | | 1350 | | | | | 1355 | | | | | | 1360 |
| AAT | GAT | GTG | GTG | GGG | GTT | GGT | CGA | CTT | TCT | GAA | AGC | AAC | GCC | GCA | AAG | 4128 |
| Asn | Asp | Val | Val | Gly | Val | Gly | Arg | Leu | Ser | Glu | Ser | Asn | Ala | Ala | Lys | |
| 1365 | | | | | 1370 | | | | | 1375 | | | | | | |
| ATG | AAT | GAC | GAT | GTT | GAT | GGT | ATT | GTA | CGC | ACC | CCA | CTC | GCT | GAA | CTG | 4176 |
| Met | Asn | Asp | Asp | Val | Asp | Gly | Ile | Val | Arg | Thr | Pro | Leu | Ala | Glu | Leu | |
| 1380 | | | | | 1385 | | | | | 1390 | | | | | | |
| TTA | GAT | GGG | GAA | GGA | CAA | ACA | GCT | GAC | ACT | GGT | CCA | CAA | AGC | GTG | AAG | 4224 |
| Leu | Asp | Gly | Glu | Gly | Gln | Thr | Ala | Asp | Thr | Gly | Pro | Gln | Ser | Val | Lys | |
| 1395 | | | | | 1400 | | | | | 1405 | | | | | | |
| TTC | AAG | TCT | CCT | GAC | CAA | ATT | GAC | TTC | AAC | CGC | TTG | TTT | ACC | CAC | CCA | 4272 |
| Phe | Lys | Ser | Pro | Asp | Gln | Ile | Asp | Phe | Asn | Arg | Leu | Phe | Thr | His | Pro | |
| 1410 | | | | | 1415 | | | | | 1420 | | | | | | |
| GTC | ACC | GAT | CTG | TTT | GAT | CCG | GTA | ACT | ATG | TTG | GTG | TAT | GAC | CAG | TAC | 4320 |
| Val | Thr | Asp | Leu | Phe | Asp | Pro | Val | Thr | Met | Leu | Val | Tyr | Asp | Gln | Tyr | |
| 1425 | | | | | 1430 | | | | | 1435 | | | | | 1440 | |
| ATA | CCG | CTG | TTT | ATT | GAT | ATC | CCA | GCA | AGT | GTG | AAC | CCT | AAA | ATG | GTT | 4368 |
| Ile | Pro | Leu | Phe | Ile | Asp | Ile | Pro | Ala | Ser | Val | Asn | Pro | Lys | Met | Val | |
| 1445 | | | | | 1450 | | | | | 1455 | | | | | | |
| CGT | TTA | AAG | GTC | TTG | AGC | TTT | GAC | ACC | AAC | GAA | CAG | AGC | TTA | GGT | CTC | 4416 |
| Arg | Leu | Lys | Val | Leu | Ser | Phe | Asp | Thr | Asn | Glu | Gln | Ser | Leu | Gly | Leu | |
| 1460 | | | | | 1465 | | | | | 1470 | | | | | | |
| CGC | TTA | GAG | TTC | TTT | AAA | CCT | GAT | CAA | GAT | ACC | CAA | CCA | AAC | AAC | AAC | 4464 |
| Arg | Leu | Glu | Phe | Phe | Lys | Pro | Asp | Gln | Asp | Thr | Gln | Pro | Asn | Asn | Asn | |
| 1475 | | | | | 1480 | | | | | 1485 | | | | | | |
| GTT | CAG | GTC | AAT | CCG | AAT | AAC | GGT | GAC | TTC | TTA | CCA | CTG | TTA | ACG | GCC | 4512 |
| Val | Gln | Val | Asn | Pro | Asn | Asn | Gly | Asp | Phe | Leu | Pro | Leu | Leu | Thr | Ala | |
| 1490 | | | | | 1495 | | | | | 1500 | | | | | | |
| TCC | AGT | CAA | GGT | CCC | CAA | ACC | TTG | TTT | AGT | CCG | TTT | AAC | CAG | TGA | CCT | 4560 |
| Ser | Ser | Gln | Gly | Pro | Gln | Thr | Leu | Phe | Ser | Pro | Phe | Asn | Gln | Trp | Pro | |
| 1505 | | | | | 1510 | | | | | 1515 | | | | | 1520 | |
| GAT | TAC | GTG | TTG | CCG | TTA | GCG | ATC | ACT | GTA | CCT | ATT | GTT | GTG | ATT | GTG | 4608 |
| Asp | Tyr | Val | Leu | Pro | Leu | Ala | Ile | Thr | Val | Pro | Ile | Val | Val | Ile | Val | |

| | | | | | | | | | | | | | | | | |
|---|---|---|---|---|---|---|---|---|---|---|---|---|---|---|---|---|
| 1525 | | | | | 1530 | | | | | 1535 | | | | | | |
| CTC | AGT | GTT | ACC | TTA | GGA | CTT | GCC | ATT | GGA | ATC | CCA | ATG | CAC | AAG | AAC | 4656 |
| Leu | Ser | Val | Thr | Leu | Gly | Leu | Ala | Ile | Gly | Ile | Pro | Met | His | Lys | Asn | |
| 1540 | | | | | 1545 | | | | | 1550 | | | | | | |
| AAA | CAG | GCC | TTG | AAG | GCT | GGG | TTT | GCG | CTA | TCA | AAC | CAA | AAG | GTT | GAT | 4704 |
| Lys | Gln | Ala | Leu | Lys | Ala | Gly | Phe | Ala | Leu | Ser | Asn | Gln | Lys | Val | Asp | |
| 1555 | | | | | 1560 | | | | | 1565 | | | | | | |
| GTG | TTG | ACC | AAA | GCG | GTT | GGT | AGT | GTC | TTT | AAG | GAA | ATC | ATT | AAC | CGC | 4752 |
| Val | Leu | Thr | Lys | Ala | Val | Gly | Ser | Val | Phe | Lys | Glu | Ile | Ile | Asn | Arg | |
| 1570 | | | | | 1575 | | | | | 1580 | | | | | | |
| ACA | GGT | ATC | AGT | CAA | GCG | CCA | AAA | CGC | TTG | AAA | CAA | ACC | AGT | GCG | GCT | 4800 |
| Thr | Gly | Ile | Ser | Gln | Ala | Pro | Lys | Arg | Leu | Lys | Gln | Thr | Ser | Ala | Ala | |
| 1585 | | | | | 1590 | | | | | 1595 | | | | | 1600 | |
| AAA | CCA | GGA | GCA | CCC | CGC | CCA | CCA | GTA | CCA | CCA | AAG | CCA | GGG | GCT | CCT | 4848 |
| Lys | Pro | Gly | Ala | Pro | Arg | Pro | Pro | Val | Pro | Pro | Lys | Pro | Gly | Ala | Pro | |
| 1605 | | | | | 1610 | | | | | 1615 | | | | | | |
| AAG | CCA | CCA | GTG | CAA | CCA | CCT | AAA | AAA | CCC | GCT | TAG | 4884 | | | | |
| Lys | Pro | Pro | Val | Gln | Pro | Pro | Lys | Lys | Pro | Ala | End | | | | | |
| 1620 | | | | | 1625 | | | | | | | | | | | |

What is claimed is:

1. A fragment of *Mycoplasma pneumoniae* P1 protein consisting essentially of SEQ ID No:1.
2. A fragment of *Mycoplasma pneumoniae* P1 proetin consisting essentially of SEQ ID No:3.
3. A fragment of *Mycoplasma pneumoniae* P1 protein consisting essentially of SEQ ID No:5.
4. A fragment of *Mycoplasma pneumoniae* P1 protein consisting essentially of SEQ ID No:7.
5. A cytadhesin polypeptide fragment corresponding to the polypeptide encoded by lambda gt11 phage P1-7, P1-9 or P1-10, ATCC accession # 40386, 40385, or 40384, respectively.

* * * * *